US007618776B2

(12) United States Patent
Lizardi

(10) Patent No.: US 7,618,776 B2
(45) Date of Patent: *Nov. 17, 2009

(54) ROLLING CIRCLE REPLICATION REPORTER SYSTEMS

(75) Inventor: Paul M. Lizardi, Cuernavaca (MX)

(73) Assignee: Yale University, New Haven, CT (US)

(*) Notice: Subject to any disclaimer, the term of this patent is extended or adjusted under 35 U.S.C. 154(b) by 269 days.

This patent is subject to a terminal disclaimer.

(21) Appl. No.: 10/896,513

(22) Filed: Jul. 22, 2004

(65) Prior Publication Data

US 2004/0265897 A1 Dec. 30, 2004

Related U.S. Application Data

(63) Continuation of application No. 10/038,718, filed on Jan. 2, 2002, now Pat. No. 6,794,474, which is a continuation of application No. 09/644,723, filed on Aug. 23, 2000, now Pat. No. 6,344,329, which is a continuation of application No. 09/132,553, filed on Aug. 11, 1998, now Pat. No. 6,210,884, which is a continuation of application No. 08/563,912, filed on Nov. 21, 1995, now Pat. No. 5,854,033.

(51) Int. Cl.
*C12Q 1/68* (2006.01)
*C12P 19/34* (2006.01)

(52) U.S. Cl. .................... 435/6; 435/91.1; 435/91.2; 435/91.5

(58) Field of Classification Search ............... None
See application file for complete search history.

(56) References Cited

U.S. PATENT DOCUMENTS

| 2,264,423 | A | 12/1941 | Wingenroth |
|---|---|---|---|
| 3,687,808 | A | 8/1972 | Merigan et al. |
| 3,921,105 | A | 11/1975 | Brgetz |
| 3,983,421 | A | 9/1976 | Yogore |
| 4,469,863 | A | 9/1984 | Ts'o |
| 4,476,301 | A | 10/1984 | Imbach et al. |
| 4,748,111 | A | 5/1988 | Dattagupta et al. |
| 4,845,205 | A | 7/1989 | Huynh Dinh et al. |
| 4,883,750 | A | 11/1989 | Whiteley et al. |
| 4,965,188 | A | 10/1990 | Bertram et al. |
| 4,981,957 | A | 1/1991 | Lebleu et al. |
| 4,984,957 | A | 1/1991 | Noguchi et al. |
| 4,994,373 | A | 2/1991 | Stavrianopoulos et al. |
| 5,001,050 | A | 3/1991 | Blanco et al. |
| 5,023,243 | A | 6/1991 | Tullis |
| 5,034,506 | A | 7/1991 | Summerton et al. |
| 5,043,272 | A | 8/1991 | Hartley |
| 5,118,800 | A | 6/1992 | Smith et al. |
| 5,130,238 | A | 7/1992 | Malek et al. |
| 5,130,302 | A | 7/1992 | Spielvogel et al. |
| 5,134,066 | A | 7/1992 | Rogers et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,185,444 | A | 2/1993 | Summerton et al. |

(Continued)

FOREIGN PATENT DOCUMENTS

| AU | 649066 | 5/1994 |
|---|---|---|
| AU | 714486 | 4/2000 |
| EP | 0 070 685 | 7/1982 |
| EP | 0 128 332 | 12/1984 |
| EP | 0 356 021 | 2/1990 |
| EP | 0 439 182 | 7/1991 |
| EP | 0 466 520 | 1/1992 |
| EP | 0 505 012 | 9/1992 |
| EP | 0 667 393 | 8/1995 |
| EP | 0 678 582 | 10/1995 |

(Continued)

OTHER PUBLICATIONS

Ausubel et al. *Current Protocols in Molecular Biology*, John Wiley & Sons, 1:1.6.1-1.6.6 (1988).

(Continued)

*Primary Examiner*—Carla Myers
(74) *Attorney, Agent, or Firm*—Ballard Spahr LLP

(57) ABSTRACT

Disclosed are compositions and a method for of amplifying nucleic acid sequences useful for detecting the presence of molecules of interest. The method is useful for detecting specific nucleic acids in a sample with high specificity and sensitivity. The method also has an inherently low level of background signal. A preferred form of the method consists of a DNA ligation operation, an amplification operation, and a detection operation. The DNA ligation operation circularizes a specially designed nucleic acid probe molecule. This operation is dependent on hybridization of the probe to a target sequence and forms circular probe molecules in proportion to the amount of target sequence present in a sample. The amplification operation is rolling circle replication of the circularized probe. A single round of amplification using rolling circle replication results in a large amplification of the circularized probe sequences. Following rolling circle replication, the amplified probe sequences are detected and quantified using any of the conventional detection systems for nucleic acids such as detection of fluorescent labels, enzyme-linked detection systems, antibody-mediated label detection, and detection of radioactive labels. Because, the amplified product is directly proportional to the amount of target sequence present in a sample, quantitative measurements reliably represent the amount of a target sequence in a sample. Major advantages of this method are that the ligation step can be manipulated to obtain allelic discrimination, the DNA replication step is isothermal, and signals are strictly quantitative because the amplification reaction is linear and is catalyzed by a highly processive enzyme. In multiplex assays, the primer oligonucleotide used for the DNA polymerase reaction can be the same for all probes. Also described are modes of the method in which additional amplification is obtained using a cascade of strand displacement reactions.

28 Claims, 12 Drawing Sheets

U.S. PATENT DOCUMENTS

| | | |
|---|---|---|
| 5,188,897 A | 2/1993 | Suhadolnik et al. |
| 5,198,543 A | 3/1993 | Blanco et al. |
| 5,214,134 A | 5/1993 | Weis et al. |
| 5,216,141 A | 6/1993 | Benner |
| 5,235,033 A | 8/1993 | Summerton et al. |
| 5,242,794 A | 9/1993 | Whiteley et al. |
| 5,264,423 A | 11/1993 | Cohen et al. |
| 5,264,562 A | 11/1993 | Matteucci |
| 5,264,564 A | 11/1993 | Matteucci |
| 5,264,567 A | 11/1993 | Numata et al. |
| 5,273,638 A | 12/1993 | Konrad et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,328,824 A | 7/1994 | Ward et al. |
| 5,354,668 A | 10/1994 | Auerbach |
| 5,359,044 A | 10/1994 | Cook et al. |
| 5,367,066 A | 11/1994 | Urdea et al. |
| 5,367,069 A | 11/1994 | Beck et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,409,818 A | 4/1995 | Davey et al. |
| 5,412,087 A | 5/1995 | McGall et al. |
| 5,427,930 A | 6/1995 | Birkenmeyer et al. |
| 5,429,807 A | 7/1995 | Matson et al. |
| 5,432,272 A | 7/1995 | Benner |
| 5,434,257 A | 7/1995 | Matteucci et al. |
| 5,443,986 A | 8/1995 | Haughland et al. |
| 5,446,137 A | 8/1995 | Maag et al. |
| 5,451,067 A | 9/1995 | Pieper |
| 5,451,203 A | 9/1995 | Lamb |
| 5,453,496 A | 9/1995 | Caruthers et al. |
| 5,455,166 A | 10/1995 | Walker |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,427 A | 12/1995 | Fujima |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,510,270 A | 4/1996 | Fodor et al. |
| 5,514,785 A | 5/1996 | Van Ness et al. |
| 5,516,134 A | 5/1996 | Crawford et al. |
| 5,516,663 A | 5/1996 | Backman et al. |
| 5,519,126 A | 5/1996 | Hecht |
| 5,519,134 A | 5/1996 | Acevedo et al. |
| 5,521,065 A | 5/1996 | Whitley et al. |
| 5,523,204 A | 6/1996 | Singer et al. |
| 5,525,711 A | 6/1996 | Hawkins et al. |
| 5,536,821 A | 7/1996 | Agrawal et al. |
| 5,538,871 A | 7/1996 | Nuovo et al. |
| 5,539,082 A | 7/1996 | Nielsen et al. |
| 5,541,306 A | 7/1996 | Agrawal et al. |
| 5,541,307 A | 7/1996 | Cook et al. |
| 5,547,843 A | 8/1996 | Studier et al. |
| 5,550,111 A | 8/1996 | Suhadolnik et al. |
| 5,552,540 A | 9/1996 | Haralambidis |
| 5,556,772 A | 9/1996 | Sorge et al. |
| 5,561,225 A | 10/1996 | Maddry et al. |
| 5,563,037 A | 10/1996 | Sutherland et al. |
| 5,563,253 A | 10/1996 | Agrawal et al. |
| 5,563,912 A | 10/1996 | Yasunaga et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,609 A | 1/1997 | Auerbach |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,599,921 A | 2/1997 | Sorge et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,389 A | 3/1997 | Auerbach |
| 5,614,390 A | 3/1997 | McCaslin et al. |
| 5,614,617 A | 3/1997 | Cook et al. |
| 5,618,704 A | 4/1997 | Sanghui et al. |
| 5,623,070 A | 4/1997 | Cook et al. |
| 5,625,050 A | 4/1997 | Beaton et al. |
| 5,627,053 A | 5/1997 | Usman et al. |
| 5,629,158 A | 5/1997 | Uhlen |
| 5,629,179 A | 5/1997 | Mierendorf et al. |
| 5,633,360 A | 5/1997 | Bischofberger et al. |
| 5,639,873 A | 6/1997 | Barascut et al. |
| 5,646,265 A | 7/1997 | McGee |
| 5,648,245 A | 7/1997 | Fire et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,710,028 A | 1/1998 | Eyal et al. |
| 5,714,320 A | 2/1998 | Kool |
| 5,714,331 A | 2/1998 | Buchardt et al. |
| 5,719,262 A | 2/1998 | Buchardt et al. |
| 5,728,526 A | 3/1998 | George et al. |
| 5,733,733 A | 3/1998 | Auerbach |
| 5,766,891 A | 6/1998 | Shuman |
| 5,795,714 A | 8/1998 | Cantor et al. |
| 5,821,084 A | 10/1998 | Olmsted et al. |
| 5,854,033 A | 12/1998 | Lizardi |
| 5,854,053 A | 12/1998 | Donovan et al. |
| 5,866,329 A | 2/1999 | Demetriou et al. |
| 5,866,336 A | 2/1999 | Nazarenko et al. |
| 5,871,921 A | 2/1999 | Landgren et al. |
| 5,874,260 A | 2/1999 | Cleuziat et al. |
| 5,876,924 A | 3/1999 | Zhang et al. |
| 5,909,132 A | 6/1999 | Trofimenkoff et al. |
| 5,925,517 A | 7/1999 | Tyagi et al. |
| 5,942,391 A | 8/1999 | Zhang et al. |
| 5,985,639 A | 11/1999 | Christianson et al. |
| 6,008,373 A | 12/1999 | Waggoner et al. |
| 6,017,703 A | 1/2000 | Kinders et al. |
| 6,033,881 A | 3/2000 | Himmler et al. |
| 6,037,130 A | 3/2000 | Tyagi et al. |
| 6,054,274 A | 4/2000 | Sampson et al. |
| 6,057,105 A | 5/2000 | Hoon et al. |
| 6,077,668 A | 6/2000 | Kool |
| 6,077,674 A | 6/2000 | Schleifer et al. |
| 6,096,880 A | 8/2000 | Kool et al. |
| 6,117,635 A | 9/2000 | Nazarenko et al. |
| 6,124,120 A | 9/2000 | Lizardi |
| 6,132,728 A | 10/2000 | Beachy et al. |
| 6,143,495 A * | 11/2000 | Lizardi et al. ............... 435/6 |
| 6,183,960 B1 | 2/2001 | Lizardi |
| 6,203,984 B1 | 3/2001 | Hu et al. |
| 6,210,884 B1 * | 4/2001 | Lizardi ............... 435/6 |
| 6,214,587 B1 | 4/2001 | Dattagupta et al. |
| 6,221,603 B1 | 4/2001 | Mahtani et al. |

| | | |
|---|---|---|
| 6,235,502 B1 | 5/2001 | Weissman et al. |
| 6,248,535 B1 | 6/2001 | Danenberg et al. |
| 6,255,082 B1 | 7/2001 | Lizardi et al. |
| 6,274,320 B1 | 8/2001 | Rothberg et al. |
| 6,277,607 B1 | 8/2001 | Tyagi et al. |
| 6,280,949 B1 | 8/2001 | Lizardi |
| 6,287,768 B1 | 9/2001 | Chenchik et al. |
| 6,287,776 B1 | 9/2001 | Hefti |
| 6,287,824 B1 | 9/2001 | Lizardi |
| 6,288,220 B1 | 9/2001 | Kambara et al. |
| 6,291,187 B1 | 9/2001 | Kingsmore et al. |
| 6,291,193 B1 | 9/2001 | Khodadoust |
| 6,291,669 B1 | 9/2001 | Kwiatkowski et al. |
| 6,294,664 B1 | 9/2001 | Ravikumar et al. |
| 6,297,006 B1 | 10/2001 | Drmanac et al. |
| 6,312,902 B1 | 11/2001 | Shultz et al. |
| 6,316,229 B1 | 11/2001 | Lizardi et al. |
| 6,323,009 B1 | 11/2001 | Lasken et al. |
| 6,329,150 B1 | 12/2001 | Lizardi et al. |
| 6,344,329 B1 | 2/2002 | Lizardi |
| 6,355,431 B1 | 3/2002 | Chee et al. |
| 6,365,729 B1 | 4/2002 | Tyagi et al. |
| 6,368,801 B1 | 4/2002 | Faruqi |
| 6,403,319 B1 | 6/2002 | Lizardi et al. |
| 6,440,707 B1 | 8/2002 | Kwok et al. |
| 6,458,544 B1 | 10/2002 | Miller |
| 6,472,185 B2 | 10/2002 | McCasky Feazel et al. |
| 6,475,736 B1 | 11/2002 | Stanton |
| 6,479,242 B1 | 11/2002 | Guo et al. |
| 6,479,244 B1 | 11/2002 | Belouchi et al. |
| 6,498,023 B1 | 12/2002 | Abarzua |
| 6,531,283 B1 | 3/2003 | Kingsmore et al. |
| 6,573,051 B2 | 6/2003 | Alsmadi et al. |
| 6,617,137 B2 | 9/2003 | Dean et al. |
| 6,632,609 B2 | 10/2003 | Lizardi |
| 6,635,425 B2 | 10/2003 | Bandaru et al. |
| 6,670,126 B2 | 12/2003 | Kingsmore et al. |
| 6,686,157 B2 | 2/2004 | Ward et al. |
| 6,703,228 B1 | 3/2004 | Landers et al. |
| 6,703,885 B1 | 3/2004 | Fan et al. |
| 6,713,257 B2 | 3/2004 | Shoemaker et al. |
| 6,777,183 B2 | 8/2004 | Abarzua |
| 6,797,474 B2 * | 9/2004 | Lizardi ............ 435/6 |
| 6,811,986 B2 | 11/2004 | Bandaru et al. |
| 6,830,884 B1 | 12/2004 | Hafner et al. |
| 6,861,222 B2 | 3/2005 | Ward et al. |
| 6,921,642 B2 | 7/2005 | Kingsmore et al. |
| 6,977,153 B2 | 12/2005 | Kumar et al. |
| 7,041,480 B2 | 5/2006 | Abarzua |
| 2001/0041340 A1 | 11/2001 | Kingsmore et al. |
| 2002/0009716 A1 | 1/2002 | Abarzua |
| 2002/0119465 A1 | 8/2002 | Zhao et al. |
| 2002/0120409 A1 | 8/2002 | Cao et al. |
| 2002/0192649 A1 | 12/2002 | Lizardi |
| 2002/0192658 A1 | 12/2002 | Ward et al. |
| 2002/0197694 A1 | 12/2002 | Shao |
| 2003/0008313 A1 | 1/2003 | Whitshire |
| 2003/0022167 A1 | 1/2003 | Alsmadi et al. |
| 2003/0032024 A1 | 2/2003 | Lizardi |
| 2003/0044794 A1 | 3/2003 | Bandaru et al. |
| 2003/0143613 A1 | 7/2003 | Kingsmore et al. |
| 2003/0152932 A1 | 8/2003 | Kumar et al. |
| 2003/0165948 A1 | 9/2003 | Alsmadi |
| 2003/0175788 A1 | 9/2003 | Alsmadi |
| 2003/0207267 A1 | 11/2003 | Lasken et al. |
| 2003/0207323 A1 | 11/2003 | Bandaru et al. |
| 2003/0235849 A1 | 12/2003 | Lizardi |
| 2004/0091857 A1 | 5/2004 | Nallur et al. |
| 2004/0121338 A1 | 6/2004 | Alsmadi et al. |
| 2004/0126770 A1 | 7/2004 | Kumar et al. |
| 2004/0191784 A1 | 9/2004 | Abarzua et al. |
| 2004/0248103 A1 | 12/2004 | Feaver et al. |
| 2005/0079523 A1 | 4/2005 | Hafner et al. |
| 2006/0166227 A1 | 7/2006 | Kingsmore et al. |
| 2006/0188893 A1 | 8/2006 | Kumar et al. |

FOREIGN PATENT DOCUMENTS

| | | |
|---|---|---|
| EP | 0 745 690 A2 | 12/1996 |
| EP | 0 756 009 A2 | 1/1997 |
| GB | 2332516 | 6/1999 |
| JP | 04304900 | * 10/1992 |
| WO | WO 91/08307 | 6/1991 |
| WO | WO 92/01813 | 2/1992 |
| WO | WO 94/16108 | 7/1994 |
| WO | WO 94/24312 | 10/1994 |
| WO | WO 95/03430 | 2/1995 |
| WO | WO 95/03432 | 2/1995 |
| WO | WO 95/22623 | 2/1995 |
| WO | WO 95/25180 | 9/1995 |
| WO | WO 95/35390 | 12/1995 |
| WO | WO 96/33207 | 10/1996 |
| WO | WO 97/17076 | 5/1997 |
| WO | WO 97/17471 | 5/1997 |
| WO | WO 97/19193 | 5/1997 |
| WO | WO 97/20948 | 6/1997 |
| WO | WO97/42346 | 11/1997 |
| WO | WO 98/04746 | 2/1998 |
| WO | WO 99/18241 | 4/1999 |
| WO | WO 99/31276 | 6/1999 |
| WO | WO 00/04193 | 1/2000 |
| WO | WO 00/15779 | 3/2000 |
| WO | WO 00/36141 | 6/2000 |
| WO | WO 00/71562 A1 | 11/2000 |
| WO | WO 01/40516 | 6/2001 |
| WO | WO 01/61037 | 8/2001 |
| WO | WO 01/64952 | 9/2001 |
| WO | WO 01/77390 | 10/2001 |
| WO | WO 01/79420 | 10/2001 |
| WO | WO 01/88190 | 11/2001 |
| WO | WO 01/97616 | 12/2001 |
| WO | WO 02/00934 | 1/2002 |
| WO | WO 02/02792 | 1/2002 |
| WO | WO 02/053780 | 7/2002 |
| WO | WO 02/077256 | 10/2002 |
| WO | WO 02/103058 | 12/2002 |
| WO | WO 03/008538 | 1/2003 |
| WO | WO 03/066908 | 8/2003 |
| WO | WO 2004/061119 | 7/2004 |

OTHER PUBLICATIONS

Barbato et al. Solid Phase Syntheses of Cyclic Oligodeoxyribonucleotides. *Tetrahedron Letters*. 28(46):5727-2728 (1987).

Bryant et al. Phosphorothioate substrates for T4 RNA ligase. *Biochemistry*. 21(23):5877-5885 (1982).

Capobianco et al. One pot solution synthesis of cyclic oligodeoxyribonucleotides. *Nucleic Acids Research*; 18(9):2661-2669 (1990).

Cheung et al. Whole genome amplification using a degenerate oligonucleotide primer allows hundreds of genotypes to be performed on less than one nanogram of genomic DNA. *Proc Natl Acad Sci USA*. 93:14676-14679 (1996).

Christian et al. Detection of DNA point mutations and mRNA expression levels by rolling circle amplification in individual cells. *Proc Natl Acad Sci USA*. 98(25):14238-14243. Epub Nov. 27, 2001 (Dec. 4, 2001).

Cummins et al. Biochemical and physicochemical properties of phosphorodithioate DNA. *Biochemistry*. 35(26):8734-8741 (1996).

de Vroom et al. Syntheses of cyclic oligonucleotides by a modified phosphotriester approach. *Nucleic Acids Research*. 16(10):4607-4620 (1988).

Diegelman et al. Generation of circular RNAs and trans-cleaving catalytic RNAs by rolling transcription of circular DNA oligonucleotides encoding hairpin ribozymes. *Nucleic Acids Res*. 26(13):3235-3241 (1998).

Doherty et al. Structural and mechanistic conservation in DNA ligases. Survey and Summary. *Nucleic Acids Res.* 28(21):4051-4058 (2000).

Dolinnaya et al. Oligonucleotide circularization by template-directed chemical ligation. *Nucleic Acids Res.* 21(23):5403-5407 (1993).

Eckstein et al. Phosphorothioates in molecular biology. *Trends in Bioch Sci.* 14:97-100 (1989).

Erie et al. Melting Behavior of a Covalently Closed, Single-Stranded, Circular DNA. *Biochemistry.* 28:268-273. (1989).

Faruqi et al. High-throughput genotyping of single nucleotide polymorphisms with rolling circle amplification. *BMC Genomics* 2(4) (2001).

Gryaznov et al. Template controlled coupling and recombination of oligonucleotide blocks containing thiophosphoryl groups. *Nucleic Acids Res.* 21(6):1403-1408 (1993).

Haff et al. Single-nucleotide polymorphism identification assays using a thermostable DNA polymerase and delayed extraction MALDI-TOF mass spectrometry. *Genome Res.* 7(4):378-388 (1997).

Ishikawa et al. Sequence-based typing of HLA-A2 alleles using a primer with an extra base mismatch. *Hum Immunol.* 42(4):315-318 (1995).

James et al. Surprising fidelity of template-directed chemical ligation of oligonucleotides. *Chemistry & Biology.* 4:595-605 (1997).

Kanaya et al. Template-Directed Polymerization of Oligoadenylates Using Cyanogen Bromide. *Biochemistry.* 25:7423-7430 (1986).

Kinoshita et al. Strand Ligation in a double-stranded DNA by T4 RNA Ligase. *Chemistry Letters.* 797-798 (1996).

Kricka. Ultrasensitive immunoassay techniques. *Clin Biochem.* 26(5):325-331 (1993).

Lyons et al. Immunosuppressant FK506 promotes neurite outgrowth in cultures of PC12 cells and sensory ganglia. *Proc Natl Acad Sci U S A.* 91(8):3191-3195 (1994).

Marshall et al. A biopolymer by any other name would bind as well: a comparison of the ligand-binding pockets of nucleic acids and proteins. *Structure.* 5(6):729-734. (1997).

Navarro et al. A general strategy for cloning viroids and other small circular RNAs that uses nminimal amounts of template and does not require prior knowledge of its sequence. *J Virol Meth.* 56:59-66 (1996).

Nilsson et al. Real-time monitoring of rolling-circle amplification using a modified molecular beacon design. *Nucleic Acids Res.* 30(14):e66 (2002).

Prakash et al. Molecular Recognition by Circular Oligonucleotides. Strong Binding of Single-Stranded DNA and RNA. *J Chem Soc, Chem Commun.* 1161-1163 (1991).

Reese et al. The H-phosphonate approach to the solution phase synthesis of linear and cyclic oligoribonucleotides. *Nucleic Acids Research.* 27(4):963-971 (1999).

Rossi et al. Functional characterization of the T4DNA ligase: a new insight into the mechanism of action. *Nucleic Acids Res.* 25(11):2106-2113 (1997).

Rubin et al. Convergent DNA synthesis: a non-enzymatic diverization approach to circular oligodeoxynucleotides. *Nucleic Acids Res.* 23(17):3547-3553 (1995).

Schenk et al. The accessibility of thiophosphorylated groups in DNA fragments to the enzymatic activity of ligases and restriction endonuclease Bbs 1. *Biochem Mol Biol Int.* 36(5):1037-1043 (1995) Abstract.

Skerra. Phosphorothioate primers improve the amplification of DNA sequences by DNA polymerases with proofreading activity. *Nucleic Acids Res.* 20(14):3551-3554 (1992).

Stratagene Catalog, p. 39 (1988).

Stratagene Catalog, p. 76 (1992).

Strong et al. Marked improvement of PAC and BAC cloning is achieved using electroelution of pulsed-field gel-separated partial digests of genomic DNA. *Nucleic Acids Res.* 25(19):3959-3961 (1997).

Unrau et al. Non-cloning amplification of specific DNA fragments from whole genomic DNA digests using DNA 'indexers'. *Gene.* . 145(2):163-169 (1994).

Welford et al. Detection of differentially expressed genes in primary tumor tissues using representational differences analysis coupled to microarray hybridization. *Nucleic Acids Res.* 26(12):3059-3065 (1998).

Wemmer et al. Preparation and melting of single strand circular DNA loops. *Nucleic Acids Res.* 13(23):8611-8621 (1985).

White et al. Concatemer chain reaction: a Taq DNA polymerase-mediated mechanism for generating long tandemly repetitive DNA sequences. *Anal Biochem.* 199(2):184-190 (1991).

Wilson et al. Enzyme complex amplification—a signal amplification method for use in enzyme immunoassays. *Anal Biochem.* 209(1):183-187 (1993).

Xu et al. Nonenzymatic autoligation in direct three-color detection of RNA and DNA point mutations. *Nature Biotechnology.* 19:148-152 (2001).

Yang et al. Combining SSH and cDNA microarrays for rapid identification of differentially expressed genes. *Nucleic Acids Res.* 27(6):1517-1523 (1999).

AAAI Board of Directors. Measurement of specific and nonspecific $IgG_4$ levels as diagnositc and prognostic tests for clinical allergy. *J Allergy Clin Immunol.* 95:652-654 (1995).

Anderson et al. A comparison of selected mRNA and protein abundances in human liver. *Electrophoresis.* 18:533-537 (1997).

Beaucage et al. Deoxynucleoside phosphoramidites—a new class of key intermediates for deoxypolynucleotide synthesis. *Tetrahedron Lett.* 22(20):1859-1862(1981).

Bonnet et al. Thermodynamic basis of the enhanced specificity of structured DNA probes. *Proc Natl Acad Sci USA.* 96(11):6171-6176 (1999).

Brush. Dye hard: protein gel staining products. *The Scientist.* 12:16-22 (1998).

Chang. The pharmacological basis of anti-IgE therapy. *Nat Biotech.* 18:157-162 (2000).

Colantuoni et al., Gene expression profiling in postmortem Rett Syndrome brain: differential gene expression and patient classification. *Neurobiol. Dis.* 8(5):847-865 (2001).

Colantuoni et al., High throughput analysis of gene expression in the human brain. *J. Neurosci. Res.* 59(1):1-10 (2000).

Craxton et al. Linear Amplification Sequencing, a Powerful Method for Sequencing DNA. *Meth. Compan. Meth. Enzymol.* 3(1):20-26 (Aug. 1991).

Crooke et al. Pharmacokinetic properties of several novel oligonucleotide analogs in mice. *J Pharmacol Exp Ther.* 277(2):923-937 (1996).

Dean et al. Rapid Amplification of Plasmid and Phage DNA Using Phi29 DNA Polymerase and Multiply-Primed Rolling Circle Amplification. *Genome Res.* 11:1095-1099 (2001).

Ekins. Ligand assays: from electrophoresis to miniaturized microarrays. *Clin Chem.* 44(9):2015-2030 (1998).

Englisch et al. Chemically modified oligonucleotides as probes and inhibitors. *Angewandte Chemie, Intl Ed.* 30(6):613-629 (1991).

Fields et al. How many genes in the human genome? *Nat Genet.* 7:345-346 (1994).

Fleischmann et al. Whole-genome random sequencing and assembly of haemophilus influenza Rd. *Science.* 269:496-512 (1995).

Gait. Oligonucleotides. *Antisense Research and Applications.* (Crooke et al, eds., CRC Press) Chapter 16; pp. 289-301 (1993).

Guatelli et al. Isothermal, in vitro amplification of nucleic acids by a multienzyme reaction molded after retroviral replication. Proc. Natl. Acad. Sci. USA 87:1874-1878 (1990).

Gygi et al. Correlation between protein and mRNA abundance in yeast. *Mol Cell Biol.* 19(3):1720-1730 (1999).

Hall et al. Nucleotides. Part XLI. Mixed anhydrides as intermediates in the synthesis of dinucleoside phosphates. *J Chem Soc.* 3291-3296 (1957).

Hall et al. Sensitive detection of DNA polymorphisms by the serial invasive signal amplification reaction. *Proc. Natl. Acad. Sci. USA* 97(15):8272-8277 (Jul. 2000).

Heinonen et al. Simple triple-label detection of seven cystic fibrosis mutations by time-resolved fluorometry. *Clin Chem.* 43(7):1142-1150 (1997).

Henegariu et al. Custom flourescent-nucleotide synthesis as an alternative method for nucleic acid labeling. *Nat Biotech.* 18:345-348 (2000).

Hermanson et al., eds. *Immobilized Affinity Ligands.* (Academic Press, NY, 1992).

Hoeltke et al. Multiple nucleic acid labeling and rainbow detection. *Anal Biochem.* 207:24-31 (1992).

Holland et al., Detection of Specific Polymerase Chain Reaction Product by Utilizing the 5'→3' Exonuclease Activity of *Thermus aquaticus* DNA Polymerase. *Proc. Natl. Acad. Sci. USA* 88:7276-7280 (Aug. 1991).

Humphery-Smith et al. Proteome analysis: genomics via the output rather than the input code. *J Protein Chem.* 16(5):537-544 (1997).

Iyer et al. 3-H-1,2-benzodithiole-3-one 1, 1-dioxide as an improved sulfurizing reagent in the solid-phase synthesis of oligodeoxyribonudeosdie phosphorothioates. *J Am Chem Soc.* 112:1253-1254 (1990).

Jiang et al. An efficient method for generation and subcloning of tandemly repeated DNA sequences with defined length, orientation and spacing. *Nucl. Acids Res.* 24(16):3278-3279 (1996).

Johnstone and Thorpe, *Immunochemistry in Practice*, Blackwell Scientific Publications, Oxford, England, pp. 30-85 (1987).

Jonsson et al. Sequence of the DNA ligase-encoding gene from *Thermus scotoductus* and conserved motifs in DNA ligases. *Gene.* 151:177-180 (1995).

Kabanov et al. A new class of antivirals: antisense oligonucleotides combined with a hydrophobic substituent effectively inhibit influenze virus reproduction and synthesis of virus-specific proteins in MDCK cells. *FEBS Lett.* 259(2):327-330 (1990).

Kessler. The digoxigenin:anti-dioxgenin (DIG) technology—a survey on the concept and realization of a novel bioanalytical indicator system. *Mol Cell Probes.* 5:161-205 (1991).

Kimpton et al. Automated DNA profiling employing multiplex amplification of short tandem repeat loci. *PCR Methods and Applications.* 3(1):13-22 (1993).

Kool. Circular oligonucleotides: new concepts in oligonucleotide design. *Annual Rev Biomol Strict.* 25:1-28 (1996).

Kwoh et al. Transcription-based amplification system and detection of amplified human immunodeficiency virus type 1 with a bead-based sandwich hybridization format. *Proc. Natl. Acad. Sci. USA* 86:1173-1177 (1989).

Letsinger et al. Cholesteryl-conjugated oligonucleotides: synthesis, properties, and activity as inhibitors of replication of human immunodeficiency virus in cell culture. *Proc Natl Acad Sci USA.* 86:6553-6556 (1989).

Letsinger et al. Synthesis of thymidine oligonucleotides by phosphite triester intermediates. *J Am Chem Soc.* 98(12):3655-3661 (Jun. 9, 1976).

Letsinger et al. Use of a stilbenedicarboxamide bridge in stabilizing, monitoring, andn photochemically altering folded conformations of oligonucleotides. *J Am Chem Soc.* 117(28):7323-7328 (1995).

Lichter et al. High-resolution mapping of human chromosome 11 by in situ hybridization with cosmid clones. *Science.* 247:64-69 (1990).

Little, Strand Displacement Amplification and Homogeneous Real-Time Detection Incorporated in a Second-Generation DNA Probe System, BDProbeTecET. *Clin. Chem.* 45:777-784 (1999).

Lizardi et al. Cascade rolling circle amplification, a homogeneous fluorescence detection system for DNA diagnostics. Clinical Chemistry 43(11):2219-2220 (1997).

Manoharan et al. Chemical modifications to improve uptake and bioavailability of antisense oligonucleotides. *Ann NY Acad Sci.* 660:306-309 (1992).

Manoharan et al. Cholic acid-oligonucleotide conjugates for antisense applications. *Bioorg Med Chem Let.* 4(8):1053-1060 (1994).

Manoharan et al. Introduction of a lipophilic thioether tether in the minor groove of nucleic acids for antisense applications. *Bioorg Med Chem Let.* 3(12):2765-2770 (1993).

Manoharan et al. Lipidic nucleic acids. *Tetra Lett.* 36(21):3651-3654 (1995).

Manoharan et al. Oligonucleotide conjugates: alteration of the pharmacokinetic properties of antisense agents. *Nucleosides & Nucleotides.* 14:969-973 (1995).

Matteucci et al. Synthesis of deoxyoligonucleotides on a polymer support. *J Am Chem Soc.* 103:3185-3191 (1981).

Mendoza et al. "High-Throughput Microarray-Based Enzyme-Linked Immunosorbent Assay (ELISA)" *BioTechniques.* vol. 27(4):778-788 (1999).

Nallur et al., Signal amplification by rolling circle amplification on DNA microarrays. *Nucl. Acids Res.* 29:E118 (2001).

Nazerenko et al. A closed tube format for amplification and detection of DNA based on energy transfer. *Nucl. Acids Res.* 25:2516-2521 (Jun. 1997).

Nichols et al. A universal nucleoside for use at ambiguous sites in DNA primers. *Nature.* 369(6480):492-493 (1994).

Nielsen. Sequence-selective recognition of DNA by strand displacement with a thymine-substituted polyamide. *Science.* 254:1497-1500 (1991).

Oberhauser et al. Effective incorporation of 2'-o-methyl-oligoribonucleotides into liposomes and enhanced cell association through modification with thiocholesterol. *Nucl Acids Res.* 20(3):533-538 (1992).

Oda et al. Accurate quantitation of protein expression and site-specific phosphorylation. *Proc Natl Acad Sci USA.* 96:6591-6596 (1999).

Parker et al. Targeted gene walking polymerase chain reaction. *Nucl Acids Res.* 19:3055-3060 (1991).

Patton et al. Components of the protein synthesis and folding machinery are induced in vascular smooth muscle cells by hypertrophic and hyperplastic agents. *J Biol Chem.* 270(36):21404-21410 (1995).

Patton. Making blind robots see: the synergy between flourescent dyes and imaging devices in automated proteomics. *Biotechniques.* 28:944-957 (2000).

Patton. Proteome analysis II. Protein subcellular redistribution: linking physiology to genomics via the proteome and separation techniques involved. *J Chromatogr.* 722:203-223 (1999).

Pless et al. Solid support synthesis of oligothymidylates using phosphorochloridates and 1-alkylmidazoles. *Nucl Acids Res.* 2(6):773-786 (1975).

Porstmann et al. Quantitation of 5-bromo-2-deoxyuridine incorporation into DNA: an enzyme immunoassay for the assessment of the lymphoid cell proliferative response. *J Immunol Meth.* 82:169-179 (1985).

Prober et al. A system for rapid DNA sequencing with fluorescent chain-terminating dideoxynucleotides, *Science.* 238:336-341 (1987).

*Protein immobilization: fundamentals and applications*, Richard F. Taylor, ed. (M. Dekker, New York, 1991).

Ramsing et al. Helix-coil transition of parallel-stranded DNA. Thermodynamics of hairpin and linear duplex oligonucleotides. *Biochem.* 28:9528-9535 (1989).

Saiki et al. Enzymatic Amplifications of β-Globin Genomic Sequences and Restiction Site Analysis for Diagnosis of Sickle Cell Anemia. *Science* 230:1350-1354 (1985).

Saiki et al. Primer-Directed Enzymatic Amplification of DNA with a Thermostable DNA Polymerase. *Science* 239:487-491 (Jan. 29, 1988).

Saison-Behmoaras et al. Short modified antisense oligonucleotides directed against Ha-*ras* point mutation induce selective cleavage of the mRNA and inhibit T24 cells proliferation. *EMBO J.* 10(5)1111-1118 (1991).

Sanghvi. Heterocyclic base modifications in nucleic acids and their applications in antisense oligonucleotides. *Antisense Research and Applications.* (Crooke et al, eds., CRC Press) Chapter 15; pp. 273-288 (1993).

Sano et al. Detection of heavy methylation in human repetitive DNA subsets by a monoclonal antibody against 5-methylcytosine. *Biochim Biophys Acta.* 951:157-165 (1988).

Schena et al. "DNA Microarrays: A Practical Approach" (Oxford University Press, New York, 1999) 1-16.

Schweitzer and Kingsmore. Combining nucleic acid amplification and detection. *Curr. Opin. Biotech.* 12(1):21-27 (Feb. 2001).

Shea et al. Synthesis, hybridization properties and antiviral activity of lipid-oligodeoxynucleotide conjugates. *Nucl Acids Res.* 18(13)3777-3783 (1990).

Shumaker et al. Mutation detection by solid phase primer extension. *Human Mutation.* 7(4):346-354 (1996).

Silzel et al. "Mass-sensing, Multianalyte Microarray Immunoassay with Imaging Detection" Clin. Chem. 44: 2036-2043 (1998).

Simpson. The natural somatic mutation frequency and human carcinogenesis. *Adv Cancer Res.* 71:209-240 (1997).

Speicher et al. Karyotyping human chromosomes by combinatorial multi-fluor FISH. *Nature Genetics.* 12(4):368-375 (1996).

Stimpson et al. Real-time detection of DNA hybridization and metling on oligonudeotide arrays by using optical wave guides. *Proc Natl Acad Sci USA.* 92(14):6379-6383 (1995).

Strauss et al. Quantitative measurement of calretinin and β-actin mRNA in rat brain micropunches without prior isolation of RNA. *Mol Brain Res.* 20:229-239 (1993).

Studier et al. Use of T7 RNA polymerase to direct expression of cloned genes. *Methods in Enzymology.* 185:60-89 (1990).

Stump et al., Tthe use of modified primers to eliminate cycle sequencing artifacts. *Nucl. Acids Res.* 27:4642-4648 (1999).

Svinarchuk et al. Inhibition of HIV proliferation in MT-4 cells by antisense oligonucleotide conjugated to lipophilic groups. *Biochimie.* 75:49-54 (1993).

Syvanen et al. Fast quantification of nucleic acid hybrids by affinity-based hybrid collection. *Nucleic Acids Research.* 14(12):5037-5048 (1986).

Tabor et al. Selective inactivation of the exonuclease activity of bacteriohage.T7 DNA polymerase by in Vitro Mutagenesis. *J Biol Chem.* 264(11):6447-6458 (1989).

Tabor et al. Selective oxidation of the exonuclease domain of bacteriophage T7 DNA polymerase. *J Biol Chem.* 262:15330-15333 (1987).

Thelwell et al. Mode of action and application of Scorpion primers to mutation detection. *Nucl. Acids Res.* 28(19):3752-3761 (2000).

Thomas et al. Cascade rolling circle amplification, a homogenous fluorescence detection system for DNA diagnostics. *Clin Chem.* 43:2219, Abs. 38 (1997).

Thorbjarnardottir et al. Cloning and sequence analysis of the DNA Iligase-encoding gene of *Rhodothermus marinus*, and overproduction, purification and characterization of two thermophilic DNA ligases. *Gene* 161:1-6 (1995).

Tsurumi et al. Functional interaction between Epstein-Barr virus DNA polymerase catalytic subunit and its accessory subunit in vitro. *Journal of Virology.* 67(12):7648-7653 (1993).

Tyagi et al. Extremely sensitive, background-free gene detection using binary probes and Qβ replicase. Proc. Natl. Acda. Sci. USA 93:5395-5400 (1996).

Uemori et al., Cloning of the DNA polymerase gene of *Bacillus caldotenax* and characterization of the gene product. *J. Biochem.* 113(3):401-410 (Mar. 1993).

Velculescu et al. Serial analysis of gene expression. *Science.* 270:484-487 (1995).

Villemain et al. The N-terminal B-domain of T4 gene 32 protein modulates the lifetime of cooperatively bound Gp32-ss nucleic acid complexes. *Biochemistry.* 35:14395-14404 (1996).

Voisey et al. Interrogation of multimeric DNA amplification products by competitive primer extension using bst DNA polymerase (large fragment). *Biotechniques.* 31(5):1122-1129 (2001).

Vogelstein et al. Supercoiled loops and eucaryotic DNA replication. *Cell.* 22:79-85 (1980).

Waggoner. Covalent labeling of proteins and nucleic acids with fluorophores. *Meth Enzymology.* 246:362-373 (1995).

Walker et al. Detection of mycobacterium tuberculosis DNA with thermophilic strand displacement amplification and fluorescence polarization. *Clin Chem.* 42(10):1604-1608 (1996).

Walker et al. Isothermal in vitro amplification of DNA by a restriction enzyme/DNA polymerase system. *Proc Natl Acad Sci USA.* 89:392-396 (1992).

Walker et al. Strand displacement amplification—an isothermal, in vitro DNA amplification technique. *Nucleic Acids Research.* 20(7):1691-1696 (1992).

Walter et al. Strand displacement amplification as an in vitro model for rolling-circle replication: deletion formation and evolution during serial transfer. *Proc Natl Acad Sci USA.* 91:7937-7941 (1994).

Wang et al. Circular RNA oligonucleotides. Synthesis, nucleic acid binding properties, and a comparison with circular DNAs. Nucl. Acids Res. 22(12):2326-2333 (1994).

Wang et al. Large-scale identification, mapping, and genotyping of single-nucleotide polymorphisms in the human genome. *Science.* 280:1077-1082 (1998).

Wansink et al. Fluorescent labeling of nascent RNA reveals transcription by RNA polymerase II in domains scattered throughout the nucleus. *Journal of Cell Biology.* 122(2):283-293 (1993).

Wiedmann et al. Ligase chain reaction (LCR)—overview and applications. *PCR Methods and Applications.* (Cold Spring Harbor Laboratory Press, Cold Spring Harbor, NY, 1994) [pp. S51-S64].

Winn-Deen et al. Non-radioactive detection of mycobacterium tuberculosis LCR products in a microtitre plate format. *Molecular and Cellular Probes.* (England) 7(3):179-186 (1993).

Wirth et al. Staining methods in gel electrophoresis, including the use of multiple detection methods. *J Chromatogr.* 698:123-143 (1995).

Young et al. Quantitative analysis of solution hybridization. *Nucleic Acid Hybridisation: A Practical Approach.* (IRL Press, 1985) pp. 47-71.

Yu et al. Cyanine dye dUTP analogs for enzymatic labeling of DNA probes. *Nucleic Acids Research.* 22(15):3226-3232 (1994).

Zehavi et al. Light-Sensitive Glycosides. I. 6-nitroveratryl β-D-glucopyranoside and 2-nitrobenzyl β-D-glucopyranoside. *J Organic Chem.* 37(14):2281-2285 (1972).

Zehavi et al. Light sensitive glycosides. II. 2-Nitrobenzyl 6-Deoxy-a-L-mannopyranoside and 2-Nitrobenzyl 6-Deoxy-β-L-galactopyranoside. *J Organic Chem.* 37(14):2285-2285 (1972).

Zhang et al. Amplification of target-specific, ligation-dependent circular probe. *Gene* 211:277-285 (1990).

Zhang et al. Whole genome amplification from a single cell: Implications for genetic analysis. *Proc. Natl. Acad. Sci. USA* 89:5847-5851 (Jul. 1992).

Zhu et al., Global Analysis of Protein Activities Using Proteome Chips. *Science* 293(5537):2101-2105 (2001).

Zhu et al. Purification and characterization of PRD1 DNA polymerase. *Biochimica Biophysica Acta.* 1219(2):267-276 (1994).

Zijderveld et al., Helix-destabilizing properties of the adenovirus DNA-binding protein. *Journal of Virology.* 68(2):1158-1164 (1994).

Abravaya, et al., "Detection Of Point Mutations With A Modified Ligase Chain Reaction (Gap-Lcr)", *Nucleic Acids Res.* 23(4): 675-682 (1995).

Aliotta, et al., "Thermostable Bst Dna Polymerase Lacks A 3'-5' Proofreading Exonuclease Activity," *Genet, Anal* 12:185-195 (1996).

Alves & Carr, "Dot Blot Detection Of Point Mutatiosn With Adjacently Hybridising Synthetic Oligonuccleotide Probes", *Nucleic Acids Res,* 16(17): 8723 (1988.

Arnold, Et El., "Assay Formats Involving Acridinium-Ester-Labeled-Dna Probes", *Clin. Chem.* 35(8): 1588-1594 (1989).

Baner et al. Signal Amplification Of Padlock Probes By Rolling Circle Replication, *Nucleic Acids Research*, Oxford University Press, Surrey, 26(22):5073-5078 (1998), Xp002112357.

Baner et al. Signal Amplification of Padlock Probes by Rolling Circle Replication, *Nucleic Acids Research*, Oxford University Press, Surrey, 26(22):5073-5078 (1998), XP002112357.

Barany, "Genetic Disease Detection And Dna Amplification Using Cloned Thermostable ligase", *Proc. Natl Acad Sci. Usa* 88:189-193 (1991).

Bertina, et al., "Mutation In Blood Coagulation Factor V Associated With Resistance ~O Activated Protein C", *Nature* 369:64-67 (1994).

Birkenmeyer & Mushahwar, "Dna Probe Amplification Methods", *Journal Of Virological Methods* 35:117-126 1991).

Blanco & Salas, "Characterization And Purification Of A Phage Ø29-Encoded Dna Polymerase Required For Initiation Of Replication", *Proc, Nat/. Acad Scl Usa* 81:5325-5329 (1984).

Blanco, Et Ai., "Highly Efficient Dna Synthesis By The Phage E29 Dna Polymerase", *Journal Of Biological Chemistry* 264(15): 8935-8940 (1989).

Blanco, et al., "Terminal Protein-Primed Dna Amplification", *Proc. Natl. Acad Sci Usa* 91:12198-12202 (1994).

Boehmer & Lehman, "Herpes Simplex Virus Type 1 Icp8: Helix-Destabilizing Properties", *Journal Of Virology* 67(2): 711-715 (1993).

Broude, Et El., "Enhanced Dna Sequencing By Hybridization", *Proc, Natl. Acad Sci. Usa* 91: 3072-3076'(1 '~94).

Burgess & Jacutin, "A New Photolabile Protecting Group For Nucleotides" '*Am. Chem Soc. Abstracts*, vol. 221 Abstract 281 (1996).

Butler & Chamberlin, "Bacteriophage Spb-Specific Rna Polymerase", *Journal Of Biological Chemistry* 257: 5772-5778 (1982).

Chatterjee, Et El., "Cloning And Overexpression Of The Gone Encoding Bacteriophage T5 Dna 'Polymerase", *Gene* 97; 13-19 (1991).

Chetverina, et al., "Cloning Of Rna Molecules In Vitro," *Nucleic Acids Research* 21:2349-2353 (1993).

Daubendiek, et al., "Generation Of Catalytic Rnas By Rolling Transcription Of Synthetic Dna Nanocircles," *Nature Biotechnology* 15:273-277 (19971.

Daubendiek, Et El., "Rolling-Circle Rna Synthesis; Circular Oligonucleotides As Efficient Substrates For 17 Rna Polymerase." *J, Am, Chem Soc.* 117:7818-7819 (1995).

Davanloo, et al., "Cloning And Expression Of The Gone For Bacteriophage T7 Rna Polymerase", *Prec. Nail. Acad, Sci. Usa* 81:2035-2039 (1984).

Dynal, Technical Handbook, "Biomagnetic Techniques In Molecular Biology" (Dynal A.S., 1995).

Ernst, Et El.,"Cyanine Dye Labeling Reagents For Sulfhydryl Groups" *Cytometry* 10:3-10 (1989).

Fire & Xu, "Rolling Replication Of Short Dna Circle", '*Proc. Natl Acad Scl Usa* 92:4641-4645 (1995).

Gasparro, et al,, "Site-Specific Targeting Of Psoralen Photoadducts With A Triple Helix-Forming Oligonucleotide: Characterization Of Psoralen Monoadduct And Crosslink Formation" *Nucleic Acids Research* 22(14): 2845-2852 (1994).

Gerdes, Et El., "Dynamic Changes In The Higher-Level Chromatin Organization Of *Specific Sequences* Revealed By In Situ Hybridization In Nuclear Halos," *J. Cell Biol.* 126:289-304 (1994).

Gunji, et al. "Correlation Between The Serum Level Of Hepatitis C Virus Rna And Disease Activities In Acute And Chronic Hepatitis C", *Int J. Cancer* 52(5): 726-730 (1992).

Guo, et al., "Enhanced Discrimination Of Single Nucleotide Polymorphisms By Artificial Mismatch Hybridization," *Nature Biotechnolcgy* 15:331-335 (1997).

Guo, Et El., "Direct Fluorescence Analysis Of Genetic Polymorphisms By Hybridization With Oligonucleotide Arrays On Glass Supports", *Nucleic Acids Res.* 22(24): 5456-5465 (1994).

Gupta, Et El., "Ninth International Conference On Aids/Fourth Std World Congress", Jun. 6-11, 1993, Berlin, Germany.

Gusev et al. Rolling Circle Amplfiication: A New Approach to Increase Sensitivity for Immunohistochemistry and Flow Cytometry, *American Journal of Pathology*, 159(1): 63-69 (Jul. 2001).

Gusev et al. Rolling Circle Amplfiication: A New Approach To Increase Sensitivity For Immunohistochemistry And Flow Cytometry, *American Journal Of Pathology*, 159(1): 63-69 (Jul. 2001).

Hacia, et al., "Detection Of Heterozygous Mutations In Brca1 Using High Density Oligonucleotide Arrays And Two-Color Fluorescence Analysis," *Nature Genetics* 14:441-447.

Hagiwarai et al., "Quantitation Of Hepatitis C Virus Rna In Serum Of Asymptornatic Blood Donors And Patients With Type C Chronic Liver Disease", *Hepatology* 17(4): 545-550 (1993).

Hanvey. et al., "Antisense And Antigone Properties Of Peptide Nucleic Acids", *Science* 258:1481-1485 (1 992).

Hata, et al., "Structure Of The Human Ornithine Transcarbamylase Gone", *J,' Biochem.* 103:302-308 (1988).

Hendrickson, et al., "High Sensitivity Multianalyte Immunoassay Using Covalent Dna-Labeled Antibodies And Polymerase Chain Reaction", *Nucleic Acids Res.* 23(3): 522-529 (1995).

Holloway, et al., "An Exonuclease-Amplification Coupled Capture Technique Improves Detection Of Pcr Product", *Nucleic Acids Research* 21 : 3905-3906 (1993).

Hoy & Schimke, "*Bromodeoyuridine/Dna* Analysis Of Replication In Cho Cells After Exposure To Uv Light", *Mutation :Research* 290:217-230 (1993).

Hsuih, et al., "Quantitative Detection Of Hcv Rna Using Novel Ligation-Dependent Polymerase Chain Reaction", *American Association For The Study Of Liver Diseases*; (Chicago, Il, Nov. 3-7, 1995) [Poster Abstract].

Itakura, Et El., "Synthesis And Use Of Synthetic Oligonucteotides",' *Annual Review Of Biochemistry* 53:323-356 (1984).

Jacobsen, E' El., "The N-Terminal Amino-Acid Sequences O'~ Dna Polymerase T From *Escherichia coil* And Of The Large And The Small Fragments Obtained By A Limited Proteolysis", *Eur. J, Biochem.* 45:623-627(1974).

Johnstone & Thorpe, *Immunochemistry In Practice* (Blackwell Scientific Publications, Oxford, England, 1987) pp. 209-216 And 241-242.

Jung, Et El., "Bacteriophage Prdl Dna Polymerase: Evolution Of Dna Polymerases", *Proc. Natl. Acad. Sci.* Usa 84:8287 (1987).

Kaboord & Benkovic, "Accessory Proteins Function As Matchmakers In The Assembly Of The T4 Dna Polymerase Holoenzyme", *Current Biology* 5:149-157 (1995).

Kalin, Et El., "Evaluation Of The Ligase Chain Reaction (Lcr) For The Detection Of Point Mutations", *Mutation Research* 283(2): 119-1 23 (1992).

Kaplan, Et El., "Rapid Photolytic Release Of Adenosine 5'-Triphosphate From A Protected Analogue: Utilization By The Na:K Pump Of Human Red Blood Cell Ghosts" *Biochem.* 17:1929-1935 {1978).

Keel, "Circular Olig0nucleotides', New Concepts In O(Igonucleotide Design," *Annual Rev. Blomol. Struct.* 25:1-28 (1996).

Kellogg, Et El., "Taqstart Antibodyt~: "Hot Start" Pcr Facilitated By A Neutralizing Monoclonal Antibody Directed Against *Taq* Dna Polymerase", *Blotechnlques* 16(6): 1134-1137 (1994).

Kerkhof, "A Comparison Of Substrates For Quantifying The Signal From A Nonradiolabeled Dna Probe", *Analytical Biochemistry* 205:359-364 (1992).

Khrapko, et al., "Hybridization Of Dna With Oligonucieotides Immobilized Ia Gel: A Convenient Method For Detecting Single Base Substitutions", *Molecular Biology (Mosk) (Ussr)* 25:718-730 (1991 ).

King, Etal., "Bridging The Gap" *Journal Of Biological Chemistry* 269(18): 13061-13064 (1994.

Kong, et al., "Characterization Of A Dna Polymerase From The Hyperthermophile Archaea *Thermococcus Etora/Is*",*Journal Of Bjb/Ogical Chemistry* 268:1965-1975 (1993).

Kunk.El, Et El., "Rapid And Efficient Site-Specific Mutagenesis Without Phengtypic Selection" *Methods In Enzymology* 154:367-382 (1987).

Lamture, Et El., "Direct Detection Of Nucleic Acid Hybridization On The Surface Of A Charge Coupled Device" *Nucleic Acids Research* 22(11): 2121-2125 (1994).

Landegren, "Molecular Mechanics Of Nucleic Acid Sequence Amplification," *Trends Genetics* 9:199-202 (1993).

Landegren, et al., "A Ligase-Mediated Gene Detection Technique", *Science* 241:1077-1080 (1988).

Langer, Et El., "Enzymatic Synthesis Of Biotin-Labeled Polynucleotides: Novel Nucleic Acid Affinity Probes", *Proc.. Natl. 4cad. Sci. USA* 78(11): 6633-6637 (1981).

Lawyer, Etal., "High-Level Expression, Purification, And Enzymatic Characterization Of Full-Length *Thermus Aquaticus* Dna Polymerase And A Truncated Form Deficient In 5' To 3' Exonuclease Activity", *Pcr Methods Applications* 2(4): 275-287 (1993).

Lefrere, Etal., "Towards A New Predictor Of Aids Progression Through The Quantitation Of Htv-1 Dna Copies By Pcr In Hiv-Infected Individuals", *Bn'tish Journal Of Haematology* 82(2): 467-471 (1992).

Lesnick & Freier, "Relative Thermodynamic Stability Of Dna, Rna, And Dna:Rna Hybrid Duplexes: Relationship With Base Composition And Structure", *Biochemistry* 34: !O807-! 08! 5 (1995}.

Liu, et al., "Rolling Circle Dna Synthesis: Small Circular Oligonucleotides As Efficient Templates For Dna Polymerases," *J, Am. Chem. Soc.* 118:1587-1594 (1996).

Lizardi et al. Mutation Detection and Single-Molecule Counting Using Isothermal Rolling-Circle Amplification, *Nature Genetics*, 19:225-232 (1998).

Lizardi et al. Mutation Detection And Single-Molecule Counting Using Isothermal Rolling-Circle Amplification, *Nature Genetics*, 19:225-232 (1998).

Loakes et al. "5-Nitroindole as a universal base analogue" Nucleic Acids Res. 1994, 22(20):45039-4043.

Lockhart, Et El., "Expression Monitoring By Hybridization To High-Density Oligonucleotide Arrays," *Nature Biotechnology* 14:1 675-1680 (1996).

Lu, et al., "High Concentration Of Peripheral Blood Mononuclear Cells Harboring Infectious Virus Correlates With Rapid Progression Of Human Immunodeficiency Virus Type 1 -Related Diseases", *Jid* 168(5): 11 65-8116 (1993).

Lukyanov, et al., "Molecule By Molecule Pcr Amplification Of Complex Dna Mixtures For Direct Sequencing: An Approach To In Vitro Cloning," *Nucleic Acids Research* 20:1691-1696 (1996).

Luo, Et El., "Improving The Fidelity Of *Thermus Thermophilus* Dna Ligase," *Nucl Acids Res*, 24'.3071-3078 (1 996}.

Marshall, et al., Detection Of Hcv Rna By The Asymmetric Gap Ligase Chain Reaction!, *Pcr Methods And Applications* 4:80-84 (1994).

Maskos, et al., "Oligonucleotide Hybridizations On Glass Supports; A Novel Linker For Oligonucleotides Synthesized In Situ," *Nucleic Acids Research* 20:1 679-1684 (1992).

Matsumoto, Et El., Primary Structure Of Bacteriophage M2 Dna Polymerase: Conserved Segments Within Protein-Riming Dna Polymerases And Dna Polymerase I Of *Escherichia coli, Gene* 84(2): 247-255 (1989).

Mccray, Et At., "A New Approach To Time-Resolved Studies Of Atp-Requiring Biological' Systems: Laser Flash Photolysis Of Caged Atp" *Proc. Natl. Acad. Sci. Usa* 77:7237-7241 (1980).

Mcgraw, et al. "Sequence-Dependant Oligonucleotide-Target Duplex Stabilities: Rules From Empirical Studies With A Set Of Twenty-Mers" *Biotechniques* 8:674-(~78 (1990).

Melton, Et El., "Efficient In Vitro Synthesis Of Biologically Active Rna And Rna Hybridization Probes From Plasmids Containing A Bacteriophage Sp6 Promoter", *Nucleic Acids Research* 12(1 8): 7035-7056 (1984).

Metzker, Et El., "Termination Of Dna Synthesis By Novel 3'-Modified-Deoxyribonucleoside 5'~Triphosphates" *Nucleicacids Research* 22:4259-4267 (1994).

Mujumdar, Et El., "Cyanine Dye Labeling Reagents Containing Isothiocyanate Groups" *Cytometry* 1 0;11-1 9 (1989).

Mullenix et al. Allergen-specific IgE Detection on Microarrays Using Rolling Circle Amplification: Correlation with in Vitro Assays for Serum IgE, *Clinical Chemistry*, 47(10):1926-1929 (2001).

Narang, Et El., "Chemical Synthesis Of Deoxyoligonucleotides By The Modified Triester Method", *Methods Enzymology* 65; 610-620 (1980).

Newton, et al., "Analysis Of Any Point Mutation In Dna'. The Amplification Refractory Mutation Refractory Mutation System (Arms)," *Nucl. Acids Res.* 17:2503-2516 (1989).

Nielsen, et al,, "Peptide Nucleic Acid {Pna). A Dna Mimic With A Peptide Backbone", *Bioconjugate Chemistry*, 5: 3-7 (1994).

Nielsen, Et El., "Peptide Nucleic Acids (Pnas): Potential Anti-Sense And Anti-Gone Agents", *Anti-Cancer Drug Design*, 8:53-63 (1993).

Nikiforov, At El., "Genetic Bit Analysis: A Solid Phase Method For Typing Single Nucleotide Poivmorphisms", *Nucleic Acids Research* 22(20): 4-167-4175 (1994).

Nikiforov, et al., "The Use Of Phosphorothioate Primers And Exonuclease Hydrolysis For The Preparation Of Single-Stranded Pcr Products And Their Detection By Solid-Phase Hybridization", *Pcr Methods And Applications* 3:285-291 (1994).

Nilsson, et al., Padlock Probes: Circularizing Oligonucteotides For Localized Dna Detection . . . , *Science* 265: 2085-2088 (1994).

Nilsson, et al., "U. Padlock Probes Reveal Single-Nucleotide Differences, Parent Of Origin And In Site Distribution Of Centromeric Sequences In Human Chromosomes 13 And 21," *Nature Genet.* 16:252-255 (1997).

Nuovo, et al. In Situ Amplification Using Universal Energy Transfer-labeled Primers, *The Journal of Histochemistry & Cytochemistry*, The Histochemical Society, Inc.; New York, New York 43(3):273-279 (1999), XP008002684.

Orum, Et El., "Single Base Pair Mutation Analysis By Pna Directed Pcr Clamping", *Nucle/C Acids Research* 21(23): 5332-5336 (1993).

Panasnko, Et El., A Simple, Three-Step Procedure For The Large Scale Purification Of Dna Ligase From A Hybrid Lysogen Construction In Vitro, *Journal Biological Cher~Istry* 253; 4-590-4592 (1978).

Pease, Et El., "Eight-Generated Oligonucleotide Arrays For Rapid Dna Sequence Analysis", *Proc, Natl. Acad, Scl Usa* 91(11): 5022-5026 (1994).

Piatak, Et El., "High Levels Of Hiv-1 in Plasma During All Stages Of Infection Determined By Competitive Pcr", *Science* 259(5102): 1749-1754 (1993).

Pillai, Et El., "Photoremovable Protecting Groups In Organic Synthesis" *Synthesis* 1-26 (1980).

Pokrovskaya & Gurevich, "In Vitro Transcription: Preparative Rna Yields In Analytical Scale Reactions", *Analytical Biochemistry* 220:420-423 (1994).

Prakash, Et El., "Structural Effects In The Recognition Of Dna By Circular Oligonucleotides," *J. Amer. Chem. Soc.* 114;3523-3527 (1992).

Richards, Et El., "Conditional Mutator Phenotypes In Hms2h2-Deficient Tumor Cell Lines," *Science* 277:1523-1526 (1997).

Ried, Et El, "Simultaneous Visualization Of Seven Different Dna Probes By In Situ Hybridization Using Combinatorial Fluorescence And Digital Imaging Microscopy", *Proc. Natl. Acad. Sci. Usa* 89(4)'. 1388-1392 (1982).

Rigler & Romano, "Differences In The Mechanism Of Stimulation Of T7 Dna Polymerase By Two Binding Modes Of *Escherichia coli/Single-Stranded* Dna-Binding Protein", *Journal Of Biological Chemistry*, 270(15): 8910-8919 (1995).

Rychlik, Et El, "Optimization Of The Annealing Temperature For Dna Amplification In Vitro", *Nucleic Acids Research* 18(21): 6409-6412 (1990).

Rys & PersIng, "Preventing False Positives: Quantitative Evaluation ~F Three Protocols For Inactivation Of Polymerase Chain Reaction Amplification Products", *Journal Of Clinical Microbiology* 31 {9): 2356-2360 (1993).

Saksela, et al., "Human Immunodeficiency Virus Type 1 Mrna Expression In Peripheral Blood Cells Predicts Disease Progression Independently Of The Numbers Of Cd4$^+$ Lymphocytes", *Proc. Natl. Acad. Sci. Usa* 91(3): 1104-11 08 (1994).

Sambrook, et al., "Molecular Cloning: A Laboratory Manual, Second Edition" (Cold Spring Harbor Laboratory Press, Cold Spring Harbor, N,Y., 1989 (Chapters 5, 6)).

Saris, et al., "Blotting Of Rna Into Rna Exchange Paper Allowing Subsequence Characterization By In Situ Translation In Addition To Blot Hybridization," *Nucleic Acids Res.* 10:4831-4843 (1982).

Schena, Et Ai., "Quantitative Monitoring Of Gone Expression Patterns With A Complementary Dna Microarray" *Science* 270:467-470 (1995).

Schena, Etal., "Parallel Human Genome Analysis: Microarray-Based Expression Monitoring Of 1000 Genes," *Proc.Natl, Acad, Sci. Usa* 91:10614-10619 (1994).

Schenborn & Meirendorf, "A Novel Transcription Property Of Sp6 And 17 Rna Polymerases: Dependence On Template Structure", *Nucleic Acids Research* 13(17): 6223-6236 (1985).

Schwarz, "Improved Yields Of Long Pcr Products Using Gone 32 Protein," *Nucl Acids Res.* 18:1079 (1990).

Schweitzer et al. Immunoassays with Rolling Circle DNA Amplification: A Versatile Platform for Ultrasensitive Antigen Detection, *PNAS*, 97(18):10113-10119 (Aug. 29, 2000).

Schweitzer et al. Multiplexed Protein Profiling on Microarrays by Rolling-Circle Amplification, *Nature Biotechnology*, 20:359-365 (Apr. 2002).

Schweitzer et al. Multiplexed Protein Profiling On Microarrays By Rolling-Circle Amplification, *Nature Biotechnology*, 20:359-365 (Apr. 2002).

Siegel, et al., "A Novel Dna Helicase From Calf Thymus", *Journal Of Biological Chemistry* 267(19): 13629-13635 [1992).

Skaliter & Lehman, "Rolling Circle Dna Replication In Vitro By A Complex Of Herpes Simplex Virus Type 1-Encoded Enzymes", *Proc, Natl. Acad. Scl Usa* 91(22): 10665-10669 (1994).

Tyagi et al. Molecular Beacons: Probes that Fluoresce upon Hybridization, *Nature Biotechnology*, 14:303-308 (Mar. 1996), XP000196024.

U.S. Appl. No. 09/803,713, filed Mar. 9, 2001, Alsmadi et al., Issue Notification, May 14, 2003.

U.S. Appl. No. 09/803,713, filed Mar. 9, 2001, Alsmadi et al., Notice of Allowance, Feb. 4, 2003.

U.S. Appl. No. 09/803,713, filed Mar. 9, 2001, Alsmadi et al., Supplemental Response, Jan. 23, 2003.

U.S. Appl. No. 09/803,713, filed Mar. 9, 2001, Alsmadi et al., Response after Non-Final Action, Nov. 5, 2002.

U.S. Appl. No. 09/803,713, filed Mar. 9, 2001, Alsmadi et al., Non-Final Rejection, Jun. 5, 2002.

U.S. Appl. No. 09/803,713, filed Mar. 9, 2001, Alsmadi et al., Response to Election / Restriction Filed, Mar. 29, 2002.

U.S. Appl. No. 09/803,713, filed Mar. 9, 2001, Alsmadi et al., Restriction Requirement, Feb. 21, 2002.

U.S. Appl. No. 10/325,490, filed Dec. 19, 2002, Alsmadi et al., Abandonment for Failure to Respond to Office Action, Mar. 8, 2007.

U.S. Appl. No. 10/325,490, filed Dec. 19, 2002, Alsmadi et al., Non-Final Rejection, Aug. 9, 2006.

U.S. Appl. No. 10/325,490, filed Dec. 19, 2002, Alsmadi et al., Response after Non-Final Action, May 25, 2006.

U.S. Appl. No. 10/325,490, filed Dec. 19, 2002, Alsmadi et al., Non-Final Rejection, Jan. 24, 2006.

U.S. Appl. No. 10/325,490, filed Dec. 19, 2002, Alsmadi et al., Response to Election / Restriction Filed, Oct. 21, 2005.

U.S. Appl. No. 10/325,490, filed Dec. 19, 2002, Alsmadi et al., Restriction Requirement, Sep. 16, 2005.

U.S. Appl. No. 10/404,944, filed Mar. 31, 2003, Alsmadi et al., Abandonment for Failure to Respond to Office Action, Nov. 27, 2006.

U.S. Appl. No. 10/404,944, filed Mar. 31, 2003, Alsmadi et al., Non-Final Rejection, May 9, 2006.

U.S. Appl. No. 10/404,944, filed Mar. 31, 2003, Alsmadi et al., Response after Non-Final Action, Mar. 6, 2006.

U.S. Appl. No. 10/404,944, filed Mar. 31, 2003, Alsmadi et al., Non-Final Rejection, Dec. 5, 2005.

U.S. Appl. No. 09/547,757, filed Apr. 12, 2000, Faruqi, Issue Notification, Mar. 21, 2002.

U.S. Appl. No. 09/547,757, filed Apr. 12, 2000, Faruqi, Notice of Allowance, Aug, 31, 2001.

U.S. Appl. No. 09/597,836, filed Jun. 20, 2000, Kingsmore et al., Issue Notification, Feb. 20, 2003.

U.S. Appl. No. 09/597,836, filed Jun. 20, 2000, Kingsmore et al., Notice of Allowance, Nov. 17, 2002.

U.S. Appl. No. 09/597,836, filed Jun. 20, 2000, Kingsmore et al., RCE with Response to Office Action, Sep. 18, 2002.

U.S. Appl. No. 09/597,836, filed Jun. 20, 2000, Kingsmore et al., Final Rejection, Mar. 19, 2002.

U.S. Appl. No. 09/597,836, filed Jun. 20, 2000, Kingsmore et al., Response after Non-Final Action, Feb. 6, 2002.

U.S. Appl. No. 09/597,836, filed Jun. 20, 2000, Kingsmore et al., Non-Final Rejection, Nov. 5, 2001.

U.S. Appl. No. 09/597,836, filed Jun. 20, 2000, Kingsmore et al., Response after Non-Final Action, Sep. 20, 2001.

U.S. Appl. No. 09/597,836, filed Jun. 20, 2000, Kingsmore et al., Non-Final Rejection, Mar. 20, 2001.

U.S. Appl. No. 09/597,836, filed Jun. 20, 2000, Kingsmore et al., Preliminary Amendment, Oct. 26, 2000.

U.S. Appl. No. 10/341,287, filed Jan. 13, 2003, Kingsmore et al., Post Issue Communication—Certificate of Correction, Sep. 7, 2005.

U.S. Appl. No. 10/341,287, filed Jan. 13, 2003, Kingsmore et al., Request for Certificate of Correction, Aug. 25, 2005.

U.S. Appl. No. 10/341,287, filed Jan. 13, 2003, Kingsmore et al., Issue Notification, Jul. 6, 2005.

U.S. Appl. No. 10/341,287, filed Jan. 13, 2003, Kingsmore et al., Notice of Allowance, Mar. 15, 2005.

U.S. Appl. No. 10/341,287, filed Jan. 13, 2003, Kingsmore et al., Response after Non-Final Action, Jan. 4, 2005.

U.S. Appl. No. 10/341,287, filed Jan. 13, 2003, Kingsmore et al., Terminal Disclaimer Filed, Jan. 4, 2005.

U.S. Appl. No. 10/341,287, filed Jan. 13, 2003, Kingsmore et al., Non-Final Rejection, Oct. 22, 2004.

U.S. Appl. No. 11/187,537, filed Jul. 22, 2005, Kingsmore et al., Requirement for Restriction / Election, Oct. 1, 2008/

U.S. Appl. No. 11/187,537, filed Jul. 22, 2005, Kingsmore et al., Miscellaneous Communication to Applicant Notice of Defective Declaration, Oct. 4, 2007.

U.S. Appl. No. 11/187,537, filed Jul. 22, 2005, Kingsmore et al., Petition Decision—Granted, Mar. 2, 2006.

U.S. Appl. No. 11/187,537, filed Jul. 22, 2005, Kingsmore et al., Petition Entered, Dec. 23, 2005.

U.S. Appl. No. 09/897,259, filed Jul. 2, 2001, Ward et al., Issue Notification, Jan. 15, 2004.

U.S. Appl. No. 09/897,259, filed Jul. 2, 2001, Ward et al., Examiner's Amendment, Dec. 8, 2003.

U.S. Appl. No. 09/897,259, filed Jul. 2, 2001, Ward et al., Notice of Allowance, Jul. 1, 2003.

U.S. Appl. No. 09/897,259, filed Jul. 2, 2001, Ward et al., Response after Non-Final Action, Apr. 18, 2003.

U.S. Appl. No. 09/897,259, filed Jul. 2, 2001, Ward et al., Non-Final Rejection, Jan. 17, 2003.

U.S. Appl. No. 09/897,259, filed Jul. 2, 2001, Ward et al., Response to Election / Restriction Filed, Nov. 4, 2002.

U.S. Appl. No. 09/897,259, filed Jul. 2, 2001, Ward et al., Restriction Requirement, Sep. 30, 2002.

U.S. Appl. No. 09/910,383, filed Jul. 20, 2001, Nallur et al., Abandonment for Failure to Respond to Office Action, Nov. 14, 2007.

U.S. Appl. No. 09/910,383, filed Jul. 20, 2001, Nallur et al., Advisory Action (PTOL-303), May 1, 2007.

U.S. Appl. No. 09/910,383, filed Jul. 20, 2001, Nallur et al., Amendment/Argument after Notice of Appeal, Apr. 18, 2007.

U.S. Appl. No. 09/910,383, filed Jul. 20, 2001, Nallur et al., Notice of Apeal Filed, Apr. 18, 2007.

U.S. Appl. No. 09/910,383, filed Jul. 20, 2001, Nallur et al., Examiner Interview Summary (PTOL-413), Apr. 9, 2007.

U.S. Appl. No. 09/910,383, filed Jul. 20, 2001, Nallur et al., Final Rejection (PTOL-326), Dec. 13, 2006.

U.S. Appl. No. 09/910,383, filed Jul. 20, 2001, Nallur et al., Response after Non-Final Action, Oct. 2, 2006.

U.S. Appl. No. 09/910,383, filed Jul. 20, 2001, Nallur et al., Non-Final Rejection, Jun. 15, 2006.

U.S. Appl. No. 09/910,383, filed Jul. 20, 2001, Nallur et al., Withdrawal of Informal Amendment Notice, Apr. 7, 2006.

U.S. Appl. No. 09/910,383, filed Jul. 20, 2001, Nallur et al., Response after Non-Final Action, Mar. 22, 2006.

U.S. Appl. No. 09/910,383, filed Jul. 20, 2001, Nallur et al., Notice of Informal or Non-Responsive RCE Amendment, Mar. 27, 2006.

U.S. Appl. No. 09/910,383, filed Jul. 20, 2001, Nallur et al., Advisory Action (PTOL-303), Dec. 13, 2005.

U.S. Appl. No. 09/910,383, filed Jul. 20, 2001, Nallur et al., Amendment after Final Rejection, Nov. 23, 2005.

U.S. Appl. No. 09/910,383, filed Jul. 20, 2001, Nallur et al., Examiner Interview Summary Record (PTOL-413), Oct. 12, 2005.

U.S. Appl. No. 09/910,383, filed Jul. 20, 2001, Nallur et al., Advisory Action (PTOL-303), Sep. 14, 2005.

U.S. Appl. No. 09/910,383, filed Jul. 20, 2001, Nallur et al., Amendment after Final Rejection, Aug. 26, 2005.

U.S. Appl. No. 09/910,383, filed Jul. 20, 2001, Nallur et al., Final Rejection (PTOL-326), May 23, 2005.

U.S. Appl. No. 09/910,383, filed Jul. 20, 2001, Nallur et al., Response after Non-Final Action, Mar. 14, 2005.

U.S. Appl. No. 09/910,383, filed Jul. 20, 2001, Nallur et al., Non-Final Rejection, Jan. 27, 2005.

U.S. Appl. No. 09/910,383, filed Jul. 20, 2001, Nallur et al., Response after Non-Final Action, Nov. 22, 2004.

U.S. Appl. No. 09/910,383, filed Jul. 20, 2001, Nallur et al., Non-Final Rejection, Jun. 23, 2004.

U.S. Appl. No. 09/977,868, filed Oct. 15, 2001, Dean et al., Issue Notification, Nov. 30, 2005.

U.S. Appl. No. 09/977,868, filed Oct. 15, 2001, Dean et al., Notice of Allowance, Feb. 22, 2005.

U.S. Appl. No. 09/977,868, filed Oct. 15, 2001, Dean et al., Examiner's Amendment, Feb. 22, 2005.

U.S. Appl. No. 09/977,868, filed Oct. 15, 2001, Dean et al., Response after Non-Final Action, Jan. 4, 2005.

U.S. Appl. No. 09/977,868, filed Oct. 15, 2001, Dean et al., Non-Final Rejection, Sep. 9, 2004.

U.S. Appl. No. 09/977,868, filed Oct. 15, 2001, Dean et al., Preliminary Amendment, Apr. 11, 2002.

U.S. Appl. No. 09/982,212, filed Oct. 18, 2001, Dean et al., Issue Notification, Aug. 21, 2003.

U.S. Appl. No. 09/982,212, filed Oct. 18, 2001, Dean et al., Notice of Allowance, May 20, 2003.

U.S. Appl. No. 09/982,212, filed Oct. 18, 2001, Dean et al., Response after Non-Final Action, May 7, 2003.

U.S. Appl. No. 09/982,212, filed Oct. 18, 2001, Dean et al., Non-Final Rejection, Apr. 18, 2003.

U.S. Appl. No. 09/982,212, filed Oct. 18, 2001, Dean et al., Preliminary Amendment, Jan. 24, 2002.

U.S. Appl. No. 09/982,212, filed Oct. 18, 2001, Dean et al., Preliminary Amendment, Oct. 8, 2001.

U.S. Appl. No. 10/272,465, filed Oct. 15, 2002, Dean et al., Decision on Petition to Revive, May 22, 2006.

U.S. Appl. No. 10/272,465, filed Oct. 15, 2002, Dean et al., Petition to Revive Application, Mar. 16, 2006.

U.S. Appl. No. 10/272,465, filed Oct. 15, 2002, Dean et al., Issue Notification, Jun. 21, 2006.

U.S. Appl. No. 10/272,465, filed Oct. 15, 2002, Dean et al., Notice of Allowance, Dec. 13, 2005.

U.S. Appl. No. 10/272,465, filed Oct. 15, 2002, Dean et al., Examiner's Amendment, Dec. 13, 2005.

U.S. Appl. No. 10/272,465, filed Oct. 15, 2002, Dean et al., Terminal Disclaimer Filed, Sep. 6, 2005.

U.S. Appl. No. 10/272,465, filed Oct. 15, 2002, Dean et al., Response after Non-Final Action, Sep. 6, 2005.

U.S. Appl. No. 10/272,465, filed Oct. 15, 2002, Dean et al., Non-Final Rejection, Aug. 5, 2005.

U.S. Appl. No. 10/429,229, filed May 2, 2003, Bornarth et al., Issue Notification, Oct. 31, 2007.

U.S. Appl. No. 10/429,229, filed May 2, 2003, Bornarth et al., Issue Fee Payment Received, Sep. 17, 2007.

U.S. Appl. No. 10/429,229, filed May 2, 2003, Bornarth et al., Supplemental Notice of Allowance, Jul. 31, 2007.

U.S. Appl. No. 10/429,229, filed May 2, 2003, Bornarth et al., Notice of Allowance, Jun. 18, 2007.

U.S. Appl. No. 10/429,229, filed May 2, 2003, Bornarth et al., Examiner Interview Summary (PTOL-413), Jun. 18, 2007.

U.S. Appl. No. 10/429,229, filed May 2, 2003, Bornarth et al., Examiner's Amendment, Jun. 18, 2007.

U.S. Appl. No. 10/429,229, filed May 2, 2003, Bornarth et al., Amendment after Final Rejection, Jun. 5, 2007.

U.S. Appl. No. 10/429,229, filed May 2, 2003, Bornarth et al., Final Rejection (PTOL-326), Feb. 28, 2007.

U.S. Appl. No. 10/429,229, filed May 2, 2003, Bornarth et al., Response after Non-Final Action & Terminal Disclaimer, Dec. 18, 2006.

U.S. Appl. No. 10/429,229, filed May 2, 2003, Bornarth et al., Non-Final Rejection, Jun. 20, 2006.

U.S. Appl. No. 10/429,229, filed May 2, 2003, Bornarth et al., Response to Election / Restriction Filed, Apr. 21, 2006.

U.S. Appl. No. 10/429,229, filed May 2, 2003, Bornarth et al., Restriction Requirement, Feb. 16, 2006.

U.S. Appl. No. 11/871,707, filed Oct. 12, 2007, Bornarth et al., Non-Final Rejection, Jan. 28, 2009.

U.S. Appl. No. 11/871,707, filed Oct. 12, 2007, Bornarth et al., Notice of Publication, Jun. 5, 2008.

U.S. Appl. No. 11/871,707, filed Oct. 12, 2007, Bornarth et al., Preliminary Amendment, Jan. 31, 2008.

U.S. Appl. No. 08/754,681, filed Nov. 21, 1996, Lizardi et al., Issue Notification, Oct. 20, 2000.

U.S. Appl. No. 08/754,681, filed Nov. 21, 1996, Lizardi et al., Issue Fee Payment Verified, Jun. 23, 2000.

U.S. Appl. No. 08/754,681, filed Nov. 21, 1996, Lizardi et al., Notice of Allowance, Mar. 28, 2000.

U.S. Appl. No. 08/754,681, filed Nov. 21, 1996, Lizardi et al., Notice of Appeal Filed, Feb. 7, 2000.

U.S. Appl. No. 08/754,681, filed Nov. 21, 1996, Lizardi et al., Amendment after Final Rejection & Terminal Disclaimer Filed, Dec. 30, 1999.

U.S. Appl. No. 08/754,681, filed Nov. 21, 1996, Lizardi et al., Final Rejection (PTOL-326), Aug. 4, 1999.

U.S. Appl. No. 08/754,681, filed Nov. 21, 1996, Lizardi et al., Supplemental Response, Apr. 16, 1999.

U.S. Appl. No. 08/754,681, filed Nov. 21, 1996, Lizardi et al., Response after Non-Final Action, Apr. 6, 1999.

U.S. Appl. No. 08/754,681, filed Nov. 21, 1996, Lizardi et al., Non-Final Rejection, Oct. 1, 1998.

U.S. Appl. No. 08/754,681, filed Nov. 21, 1996, Lizardi et al., Response after Non-Final Action, Jul. 9, 1998.

U.S. Appl. No. 08/754,681, filed Nov. 21, 1996, Lizardi et al., Non-Final Rejection, Jan. 6, 1998.

U.S. Appl. No. 08/754,681, filed Nov. 21, 1996, Lizardi et al., Response after Non-Final Action, Oct. 24, 1997.

U.S. Appl. No. 09/602,428, filed Jun. 23, 2000, Lizardi et al., Issue Notification, Nov. 21, 2001.

U.S. Appl. No. 09/602,428, filed Jun. 23, 2000, Lizardi et al., Notice of Allowance, Jun. 28, 2001.

U.S. Appl. No. 09/602,428, filed Jun. 23, 2000, Lizardi et al., Terminal Disclaimer Filed, Apr. 12, 2001.

U.S. Appl. No. 09/602,428, filed Jun. 23, 2000, Lizardi et al., Response after Non-Final Action, Apr. 12, 2001.

U.S. Appl. No. 09/602,428, filed Jun. 23, 2000, Lizardi et al., Non-Final Rejection, Nov. 22, 2000.

U.S. Appl. No. 09/602,428, filed Jun. 23, 2000, Lizardi et al., Preliminary Amendment, Jun. 23, 2000.

U.S. Appl. No. 09/841,513, filed Apr. 24, 2001, Lizardi, Issue Notification, Sep. 25, 2003.

U.S. Appl. No. 09/841,513, filed Apr. 24, 2001, Lizardi, Terminal Disclaimer Filed, May 7, 2003.

U.S. Appl. No. 09/841,513, filed Apr. 24, 2001, Lizardi, Notice of Allowance, Jan. 16, 2003.

U.S. Appl. No. 09/841,513, filed Apr. 24, 2001, Lizardi, Terminal Disclaimer Filed, Oct. 24, 2002.

U.S. Appl. No. 09/841,513, filed Apr. 24, 2001, Lizardi, Response after Non-Final Action, Oct. 24, 2002.

U.S. Appl. No. 09/841,513, filed Apr. 24, 2001, Lizardi, Non-Final Rejection, Apr. 30, 2002.

U.S. Appl. No. 09/841,513, filed Apr. 24, 2001, Lizardi, Preliminary Amendment, Apr. 24, 2001.

U.S. Appl. No. 10/413,041, filed Apr. 10, 2003, Lizardi et al., Abandonment for Failure to Respond to Office Action, Apr. 5, 2006.

U.S. Appl. No. 10/413,041, filed Apr. 10, 2003, Lizardi et al., Restriction Requirement, Sep. 22, 2005.

U.S. Appl. No. 10/072,666, filed Feb 8, 2002, Kumar et al., Notice of Allowance, Jan. 27, 2009.

U.S. Appl. No. 10/072,666, filed Feb 8, 2002, Kumar et al., Request for Continuted Examination, Nov. 24, 2008.

U.S. Appl. No. 10/072,666, filed Feb 8, 2002, Kumar et al., Notice of Allowance, Sep. 26, 2008.

U.S. Appl. No. 10/072,666, filed Feb 8, 2002, Kumar et al., Examiner Amendment Communication, Sep. 22, 2008.

U.S. Appl. No. 10/072,666, filed Feb 8, 2002, Kumar et al., Terminal Disclaimer Filed, Sep. 10, 2008.

U.S. Appl. No. 10/072,666, filed Feb 8, 2002, Kumar et al., Amendment after Final Rejection, Sep. 10, 2008.

U.S. Appl. No. 10/072,666, filed Feb 8, 2002, Kumar et al., Final Rejection, Jul. 15, 2008.

U.S. Appl. No. 10/072,666, filed Feb 8, 2002, Kumar et al., Response to Non-Final Action, Apr. 30, 2008.

U.S. Appl. No. 10/072,666, filed Feb 8, 2002, Kumar et al., Non-Final Rejection, Feb. 1, 2008.

U.S. Appl. No. 10/072,666, filed Feb 8, 2002, Kumar et al., Response after Non-Final Action, Nov. 15, 2007.

U.S. Appl. No. 10/072,666, filed Feb 8, 2002, Kumar et al., Non-Final Rejection, Jul. 9, 2007.

U.S. Appl. No. 10/072,666, filed Feb 8, 2002, Kumar et al., Response after Non-Final Action, Apr. 24, 2007.

U.S. Appl. No. 10/072,666, filed Feb 8, 2002, Kumar et al., Non-Final Rejection, Jan. 24, 2007.

U.S. Appl. No. 10/072,666, filed Feb 8, 2002, Kumar et al., Request for Continued Examination (RCE) & Response t/o Office Action, Nov. 30, 2006.
U.S. Appl. No. 10/072,666, filed Feb 8, 2002, Kumar et al., Advisory Action (PTOL-303), Nov. 8, 2006.
U.S. Appl. No. 10/072,666, filed Feb 8, 2002, Kumar et al., Amendment after Final Rejection, Oct. 20, 2006.
U.S. Appl. No. 10/072,666, filed Feb 8, 2002, Kumar et al., Final Rejection (PTOL-326), Jul. 31, 2006.
U.S. Appl. No. 10/072,666, filed Feb 8, 2002, Kumar et al., Response after Non-Final Action, May 15, 2006.
U.S. Appl. No. 10/072,666, filed Feb 8, 2002, Kumar et al., Non-Final Rejection, Jan. 27, 2006.
U.S. Appl. No. 10/072,666, filed Feb 8, 2002, Kumar et al., Examiner Interview Summary Record (PTOL-413), Aug. 11, 2005.
U.S. Appl. No. 10/072,666, filed Feb 8, 2002, Kumar et al., Request for Continued Examination (RCE) & Response to Office Action, Nov. 11, 2005.
U.S. Appl. No. 10/072,666, filed Feb 8, 2002, Kumar et al., Final Rejection (PTOL-326), Jul. 11, 2005.
U.S. Appl. No. 10/072,666, filed Feb 8, 2002, Kumar et al., Response after Non-Final Action, Apr. 27, 2005.
U.S. Appl. No. 10/072,666, filed Feb 8, 2002, Kumar et al., Notice of Restarted Response Period, Feb. 10, 2005.
U.S. Appl. No. 10/072,666, filed Feb 8, 2002, Kumar et al., Non-Final Rejection, Dec. 2, 2004.
U.S. Appl. No. 10/072,666, filed Feb 8, 2002, Kumar et al., Response after Non-Final Action, Aug. 4, 2004.
U.S. Appl. No. 10/072,666, filed Feb 8, 2002, Kumar et al., Non-Final Rejection, Apr. 19, 2004.
U.S. Appl. No. 10/072,666, filed Feb 8, 2002, Kumar et al., Response after Non-Final Action, Nov. 10, 2003.
U.S. Appl. No. 10/072,666, filed Feb 8, 2002, Kumar et al., Non-Final Rejection, May 8, 2003.
U.S. Appl. No. 09/460,078, filed Dec. 14, 1999, Hafner et al., Issue Notification, Nov. 25, 2004.
U.S. Appl. No. 09/460,078, filed Dec. 14, 1999, Hafner et al., Notice of Allowance, Jul. 14, 2004.
U.S. Appl. No. 09/460,078, filed Dec. 14, 1999, Hafner et al., Amendment after Final Rejection, Jun. 17, 2004.
U.S. Appl. No. 09/460,078, filed Dec. 14, 1999, Hafner et al., Examiner Interview Summary (PTOL-413), May 25, 2004.
U.S. Appl. No. 09/460,078, filed Dec. 14, 1999, Hafner et al., Final Rejection (PTOL-326), Feb. 13, 2004.
U.S. Appl. No. 09/460,078, filed Dec. 14, 1999, Hafner et al., Response after Non-Final Action, Nov. 24, 2003.
U.S. Appl. No. 09/460,078, filed Dec. 14, 1999, Hafner et al., Non-Final Rejection, May 19, 2003.
U.S. Appl. No. 09/460,078, filed Dec. 14, 1999, Hafner et al., Response after Non-Final Action, Jan. 14, 2003.
U.S. Appl. No. 09/460,078, filed Dec. 14, 1999, Hafner et al., Non-Final Rejection, Sep. 4, 2002.
U.S. Appl. No. 09/460,078, filed Dec. 14, 1999, Hafner et al., Request for Continued Examination (RCE), Jun. 17, 2002.
U.S. Appl. No. 09/460,078, filed Dec. 14, 1999, Hafner et al., Notice of Appeal Filed, Jan. 25, 2002.
U.S. Appl. No. 09/460,078, filed Dec. 14, 1999, Hafner et al., Final Rejection (PTOL-326), Jul. 17, 2001.
U.S. Appl. No. 09/460,078, filed Dec. 14, 1999, Hafner et al., Response after Non-Final Action, May 23, 2001.
U.S. Appl. No. 09/460,078, filed Dec. 14, 1999, Hafner et al., Non-Final Rejection, Nov. 20, 2000.
U.S. Appl. No. 09/460,078, filed Dec. 14, 1999, Hafner et al., Response to Election / Restriction Filed, Oct. 3, 2000.
U.S. Appl. No. 09/460,078, filed Dec. 14, 1999, Hafner et al., Notice of Restarted Response Period, Jun. 30, 2000.
U.S. Appl. No. 09/460,078, filed Dec. 14, 1999, Hafner et al., Restriction Requirement, May 23, 2000.
U.S. Appl. No. 10/917,580, filed Aug. 13, 2004, Hafner et al., Issue Notification, Mar. 26, 2008.
U.S. Appl. No. 10/917,580, filed Aug. 13, 2004, Hafner et al., Notice of Allowance, Nov. 30, 2007.
U.S. Appl. No. 10/917,580, filed Aug. 13, 2004, Hafner et al., Examiner's Amendment Communication, Nov. 30, 2007.
U.S. Appl. No. 10/917,580, filed Aug. 13, 2004, Hafner et al., Terminal Disclaimer Filed, Oct. 1, 2007.
U.S. Appl. No. 10/917,580, filed Aug. 13, 2004, Hafner et al., Response after Non-Final Action, Oct. 1, 2007.
U.S. Appl. No. 10/917,580, filed Aug. 13, 2004, Hafner et al., Non-Final Rejection, Jun. 25, 2007.
U.S. Appl. No. 10/917,580, filed Aug. 13, 2004, Hafner et al., Response to Election / Restriction Filed, May 10, 2007.
U.S. Appl. No. 10/917,580, filed Aug. 13, 2004, Hafner et al., Restriction Requirement, Jan. 11, 2007.
U.S. Appl. No. 10/917,580, filed Aug. 13, 2004, Hafner et al., Preliminary Amendment, Nov. 19, 2004.
U.S. Appl. No. 10/325,665, filed Dec. 19, 2002, Alsmadi et al., Abandonment for failure to respond to office action, Nov. 10, 2008.
U.S. Appl. No. 10/325,665, filed Dec. 19, 2002, Alsmadi et al., Non-Final Rejection, Apr. 17, 2008.
U.S. Appl. No. 10/325,665, filed Dec. 19, 2002, Alsmadi et al., Examiner Interview Summary, Apr. 17, 2008.
U.S. Appl. No. 10/325,665, filed Dec. 19, 2002, Alsmadi et al., Non-Final Rejection, Oct. 25, 2007.
U.S. Appl. No. 10/325,665, filed Dec. 19, 2002, Alsmadi et al., Amendment/Argument after Notice of Appeal, Sep. 25, 2007.
U.S. Appl. No. 10/325,665, filed Dec. 19, 2002, Alsmadi et al., Final Rejection (PTOL-326), Mar. 26, 2007.
U.S. Appl. No. 10/325,665, filed Dec. 19, 2002, Alsmadi et al., Response after Non-Final Action, Dec. 22, 2006.
U.S. Appl. No. 10/325,665, filed Dec. 19, 2002, Alsmadi et al., Non-Final Rejection, Aug. 3, 2006.
U.S. Appl. No. 10/325,665, filed Dec. 19, 2002, Alsmadi et al., Response after Non-Final Action & Terminal Disclaimer, Apr. 18, 2006.
U.S. Appl. No. 10/325,665, filed Dec. 19, 2002, Alsmadi et al., Non-Final Rejection, Dec. 30, 2005.
U.S. Appl. No. 10/325,665, filed Dec. 19, 2002, Alsmadi et al., Response to Election / Restriction Filed, Sep. 21, 2005.
U.S. Appl. No. 10/325,665, filed Dec. 19, 2002, Alsmadi et al., Restriction Requirement, Apr. 21, 2005.
U.S. Appl. No. 10/335,573, filed Dec. 31, 2002, Kumar et al., Issue Notification, Nov. 30, 2005.
U.S. Appl. No. 10/335,573, filed Dec. 31, 2002, Kumar et al., Notice of Allowance, Mar. 29, 2005.
U.S. Appl. No. 10/335,573, filed Dec. 31, 2002, Kumar et al., Response after Non-Final Action, Dec. 1, 2004.
U.S. Appl. No. 10/335,573, filed Dec. 31, 2002, Kumar et al., Non-Final Rejection, Jul. 29, 2004.
U.S. Appl. No. 11/201,339, filed Aug. 10, 2005, Kumar et al., Abandonment for Failure to Respond to Office Action, May 12, 2008.
U.S. Appl. No. 11/201,339, filed Aug. 10, 2005, Kumar et al., Restriction Requirement, Sep. 25, 2007.
U.S. Appl. No. 10/327,602, filed Dec. 20, 2002, Lasken, Non-Final Rejection, Jan. 5, 2009.
U.S. Appl. No. 10/327,602, filed Dec. 20, 2002, Lasken, Request for Continued Examination (RCE), Dec. 11, 2008.
U.S. Appl. No. 10/327,602, filed Dec. 20, 2002, Lasken, Advisory Action (PTOL-303), Nov. 24, 2008.
U.S. Appl. No. 10/327,602, filed Dec. 20, 2002, Lasken, Amendment after Final Rejection, Nov. 10, 2008.
U.S. Appl. No. 10/327,602, filed Dec. 20, 2002, Lasken, Final Rejection, Aug. 12, 2008.
U.S. Appl. No. 10/327,602, filed Dec. 20, 2002, Lasken, Response after Final Rejection, May 15, 2008.
U.S. Appl. No. 10/327,602, filed Dec. 20, 2002, Lasken, Non-Final Rejection, Jan. 17, 2008.
U.S. Appl. No. 10/327,602, filed Dec. 20, 2002, Lasken, Request for Continued Examination, Oct. 25, 2007.
U.S. Appl. No. 10/327,602, filed Dec. 20, 2002, Lasken, Examiner Interview Summary, Oct. 16, 2007.
U.S. Appl. No. 10/327,602, filed Dec. 20, 2002, Lasken, Amendment after Final, Oct. 1, 2007.
U.S. Appl. No. 10/327,602, filed Dec. 20, 2002, Lasken, Final Rejection, May 23, 2007.

U.S. Appl. No. 10/327,602, filed Dec. 20, 2002, Lasken, Response after Non-Final Rejection, Mar. 15, 2007.
U.S. Appl. No. 10/327,602, filed Dec. 20, 2002, Lasken, Non-Final Rejection, Nov. 14, 2006.
U.S. Appl. No. 10/327,602, filed Dec. 20, 2002, Lasken, Response after Non-Final Rejection, Aug. 28, 2006.
U.S. Appl. No. 10/327,602, filed Dec. 20, 2002, Lasken, Restriction Requirement, Jun. 26, 2006.
U.S. Appl. No. 10/405,822, filed Mar. 31, 2003, Abarzua et al., Advisory Action (PTOL-303), Feb. 27, 2009.
U.S. Appl. No. 10/405,822, filed Mar. 31, 2003, Abarzua et al., Amendment after Final Rejection, Feb. 11, 2009.
U.S. Appl. No. 10/405,822, filed Mar. 31, 2003, Abarzua et al., Examiner Interview Summary Record (PTOL-413), Dec. 11, 2008.
U.S. Appl. No. 10/405,822, filed Mar. 31, 2003, Abarzua et al., Final Rejection, Sep. 11, 2008.
U.S. Appl. No. 10/405,822, filed Mar. 31, 2003, Abarzua et al., Request for Continued Examination, Dec. 28, 2007.
U.S. Appl. No. 10/405,822, filed Mar. 31, 2003, Abarzua et al., Mail Advisory Action (PTOL-303), Nov. 9, 2007.
U.S. Appl. No. 10/405,822, filed Mar. 31, 2003, Abarzua et al., Amendment/Argument after Notice of Appeal, Oct. 30, 2007.
U.S. Appl. No. 10/405,822, filed Mar. 31, 2003, Abarzua et al., Notice of Appeal Filed, Oct. 30, 2007.
U.S. Appl. No. 10/405,822, filed Mar. 31, 2003, Abarzua et al., Mail Final Rejection (PTOL-326), Apr. 30, 2007.
U.S. Appl. No. 10/405,822, filed Mar. 31, 2003, Abarzua et al., Response after Non-Final Action, Jan. 25, 2007.
U.S. Appl. No. 10/405,822, filed Mar. 31, 2003, Abarzua et al., Mail Non-Final Rejection, Aug. 2, 2006.
U.S. Appl. No. 10/405,822, filed Mar. 31, 2003, Abarzua et al., Response to Ejection / Restriction Filed, Jun. 6, 2006.
U.S. Appl. No. 10/405,822, filed Mar. 31, 2003, Abarzua et al., Mail Restriction Requirement, Dec. 13, 2005.
U.S. Appl. No. 10/454,946, filed Jun. 4, 2003, Feaver et al., Non-Final Rejection, Nov. 24, 2008.
U.S. Appl. No. 10/454,946, filed Jun. 4, 2003, Feaver et al., Request for Continued Examination, Aug. 29, 2008.
U.S. Appl. No. 10/454,946, filed Jun. 4, 2003, Feaver et al., Advisory Action (PTOL-303), Mar. 25, 2008.
U.S. Appl. No. 10/454,946, filed Jun. 4, 2003, Feaver et al., Amendment after Final, Mar. 25, 2008.
U.S. Appl. No. 10/454,946, filed Jun. 4, 2003, Feaver et al., Notice of Appeal Filed, Mar. 17, 2008.
U.S. Appl. No. 10/454,946, filed Jun. 4, 2003, Feaver et al., Amendment after Final, Feb. 8, 2008.
U.S. Appl. No. 10/454,946, filed Jun. 4, 2003, Feaver et al., Examiner Interview Summary Record (PTOL-413), Jan. 29, 2008.
U.S. Appl. No. 10/454,946, filed Jun. 4, 2003, Feaver et al., Final Rejection (PTOL-326), Sep. 18, 2007.
U.S. Appl. No. 10/454,946, filed Jun. 4, 2003, Feaver et al., Response after Non-Final Action, Jul. 5, 2007.
U.S. Appl. No. 10/454,946, filed Jun. 4, 2003, Feaver et al., Non-Final Rejection, Feb. 29, 2007.
U.S. Appl. No. 10/454,946, filed Jun. 4, 2003, Feaver et al., Reponse after Non-Final Action, Nov. 20, 2006.
U.S. Appl. No. 10/454,946, filed Jun. 4, 2003, Feaver et al., Non-Final Rejection, Jul. 26, 2006.
U.S. Appl. No. 10/454,946, filed Jun. 4, 2003, Feaver et al., Response to Election / Restriction Filed, May 4, 2006.
U.S. Appl. No. 10/454,946, filed Jun. 4, 2003, Feaver et al., Restriction Requirement, Feb. 6, 2006.
U.S. Appl. No. 10/456,056, filed Jun. 6, 2003, Kumar et al., Amendment/Req. Reconsideration-After Non-Final Reject, Oct. 23, 2008.
U.S. Appl. No. 10/456,056, filed Jun. 6, 2003, Kumar et al., Non-Final Rejection, Aug. 8, 2008.
U.S. Appl. No. 10/456,056, filed Jun. 6, 2003, Kumar et al., Request for Continued Examination (RCE), Apr. 7, 2008.
U.S. Appl. No. 10/456,056, filed Jun. 6, 2003, Kumar et al., Amendment/Argument after Notice of Appeal, Mar. 7, 2008.
U.S. Appl. No. 10/456,056, filed Jun. 6, 2003, Kumar et al., Notice of Appeal, Sep. 6, 2007.
U.S. Appl. No. 10/456,056, filed Jun. 6, 2003, Kumar et al., Examiner Interview Summary Record (PTOL-413), Apr. 17, 2007.
U.S. Appl. No. 10/456,056, filed Jun. 6, 2003, Kumar et al., Final Rejection, Mar. 6, 2007.
U.S. Appl. No. 10/456,056, filed Jun. 6, 2003, Kumar et al., Amendment/Req. Reconsideration-After Non-Final Rejection, Dec. 11, 2006.
U.S. Appl. No. 10/456,056, filed Jun. 6, 2003, Kumar et al., Non-Final Rejection, Aug. 2, 2006.
U.S. Appl. No. 10/456,056, filed Jun. 6, 2003, Kumar et al., Response to Election / Restriction Filed, May 15, 2006.
U.S. Appl. No. 10/456,056, filed Jun. 6, 2003, Kumar et al., Requirement for Restriction / Election, Feb. 23, 2006.
U.S. Appl. No. 09/920,571, filed Jul. 31, 2001, Lasken et al., Final Rejection, Sep. 12, 2008.
U.S. Appl. No. 09/920,571, filed Jul. 31, 2001, Lasken et al., Response after Non-Final Action, Jul. 2, 2008.
U.S. Appl. No. 09/920,571, filed Jul. 31, 2001, Lasken et al., Non-Final Rejection, Mar. 11, 2008.
U.S. Appl. No. 09/920,571, filed Jul. 31, 2001, Lasken et al., Response after Non-Final Action, Dec. 27, 2007.
U.S. Appl. No. 09/920,571, filed Jul. 31, 2001, Lasken et al., Non-Final Rejection, Jun. 28, 2007.
U.S. Appl. No. 09/920,571, filed Jul. 31, 2001, Lasken et al., Response to Election/Restriction Filed, May 7, 2007.
U.S. Appl. No. 09/920,571, filed Jul. 31, 2001, Lasken et al., Mail Restriction Requirement, Mar. 6, 2007.
U.S. Appl. No. 09/920,571, filed Jul. 31, 2001, Lasken et al., Request for Continued Examination (RCE) & Response to Office Action, Dec. 11, 2006.
U.S. Appl. No. 09/920,571, filed Jul. 31, 2001, Lasken et al., Mail Final Rejection (PTOL-326), Jun. 12, 2006.
U.S. Appl. No. 09/920,571, filed Jul. 31, 2001, Lasken et al., Response after Non-Final Rejection, Mar. 29, 2006.
U.S. Appl. No. 09/920,571, filed Jul. 31, 2001, Lasken et al., Mail Non-Final Rejection, Nov. 1, 2005.
U.S. Appl. No. 09/920,571, filed Jul. 31, 2001, Lasken et al., Request for Continued Examination (RCE) & Response to Office Action, Aug. 19, 2005.
U.S. Appl. No. 09/920,571, filed Jul. 31, 2001, Lasken et al., Mail Advisory Action (PTOL-303), Jun. 20, 2005.
U.S. Appl. No. 09/920,571, filed Jul. 31, 2001, Lasken et al., Amendment/Argument after Notice of Appeal, Jun. 2, 2005.
U.S. Appl. No. 09/920,571, filed Jul. 31, 2001, Lasken et al., Notice of Appeal Filed, Jun. 2, 2005.
U.S. Appl. No. 09/920,571, filed Jul. 31, 2001, Lasken et al., Mail final Rejection (PTOL-326), Feb. 14, 2005.
U.S. Appl. No. 09/920,571, filed Jul. 31, 2001, Lasken et al., Response after Non-Final Action, Nov. 24, 2004.
U.S. Appl. No. 09/920,571, filed Jul. 31, 2001, Lasken et al., Mail Non-Final Rejection, Aug. 25, 2004.
U.S. Appl. No. 09/920,571, filed Jul. 31, 2001, Lasken et al., Request for Continued Examination (RCE), Jul. 12, 2004.
U.S. Appl. No. 09/920,571, filed Jul. 31, 2001, Lasken et al., Mail Advisory Action (PROL-303), Jun. 23, 2004.
U.S. Appl. No. 09/920,571, filed Jul. 31, 2001, Lasken et al., Amendment/Argument after Notice of Appeal, Jun. 1, 2004.
U.S. Appl. No. 09/920,571, filed Jul. 31, 2001, Lasken et al., Notice of Appeal Filed, Jun. 1, 2004.
U.S. Appl. No. 09/920,571, filed Jul. 31, 2001, Lasken et al., Mail Final Rejection (PTOL-326), Feb. 18, 2004.
U.S. Appl. No. 09/920,571, filed Jul. 31, 2001, Lasken et al., Response after Non-Final Action, Oct. 17, 2003.
U.S. Appl. No. 09/920,571, filed Jul. 31, 2001, Lasken et al., Mail Non-Final Rejection, Dec. 20, 2002.
U.S. Appl. No. 09/920,571, filed Jul. 31, 2001, Lasken et al., Supplemental Response, Oct. 3, 2003.
U.S. Appl. No. 09/920,571, filed Jul. 31, 2001, Lasken et al., Supplemental Response, Sep. 20, 2002.
U.S. Appl. No. 09/920,571, filed Jul. 31, 2001, Lasken et al., Mail Notice of Informal or Non-Responsive Amendment, Aug. 27, 2002.
U.S. Appl. No. 09/920,571, filed Jul. 31, 2001, Lasken et al., Mail Non-Final Rejection, Dec. 12, 2001.

U.S. Appl. No. 09/577,444, filed May 24, 2000, Kingsmore et al., Issue Notification, Aug. 30, 2001.
U.S. Appl. No. 09/577,444, filed May 24, 2000, Kingsmore et al., Notice of Allowance, Mar. 29, 2001.
U.S. Appl. No. 09/577,444, filed May 24, 2000, Kingsmore et al., Examiner Interview Summary Record (PTOL-413), Mar. 22, 2001.
U.S. Appl. No. 09/897,665, filed Jul. 2, 2001, Kingsmore et al., Issue Notification, Dec. 11, 2003.
U.S. Appl. No. 09/897,665, filed Jul. 2, 2001, Kingsmore et al., Notice of Allowance, Jul. 30, 2003.
U.S. Appl. No. 09/897,665, filed Jul. 2, 2001, Kingsmore et al., Notice of Appeal Filed, Jun. 2, 2003.
U.S. Appl. No. 09/897,665, filed Jul. 2, 2001, Kingsmore et al., Terminal Disclaimer Filed, Jun. 2, 2003.
U.S. Appl. No. 09/897,665, filed Jul. 2, 2001, Kingsmore et al., Final Rejection (PTOL-326), Feb. 25, 2003.
U.S. Appl. No. 09/897,665, filed Jul. 2, 2001, Kingsmore et al., Response after Non-Final Action, Dec. 10, 2002.
U.S. Appl. No. 09/897,665, filed Jul. 2, 2001, Kingsmore et al., Non-Final Rejection, Jul. 19, 2002.
U.S. Appl. No. 09/910,372, filed Jul. 20, 2001, Bandaru et al., Issue Notification, Oct. 2, 2003.
U.S. Appl. No. 09/910,372, filed Jul. 20, 2001, Bandaru et al., Notice of Allowance, Apr. 8, 2003.
U.S. Appl. No. 09/910,372, filed Jul. 20, 2001, Bandaru et al., Response after Non-Final Action, Mar. 20, 2003.
U.S. Appl. No. 09/910,372, filed Jul. 20, 2001, Bandaru et al., Response after Non-Final Action, Jan. 22, 2003.
U.S. Appl. No. 09/910,372, filed Jul. 20, 2001, Bandaru et al., Non-Final Rejection, Nov. 13, 2002.
U.S. Appl. No. 09/910,372, filed Jul. 20, 2001, Bandaru et al., Response to Election / Restriction Filed, Oct. 4, 2002.
U.S. Appl. No. 09/910,372, filed Jul. 20, 2001, Bandaru et al., Restriction Requirement, Sep. 17, 2002.
U.S. Appl. No. 10/465,759, filed Jun. 19, 2003, Bandaru et al., Issue Notification, Oct. 14, 2004.
U.S. Appl. No. 10/465,759, filed Jun. 19, 2003, Bandaru et al., Notice of Allowance, May 4, 2004.
U.S. Appl. No. 10/465,759, filed Jun. 19, 2003, Bandaru et al., Response after Non-Final Action, Apr. 12, 2004.
U.S. Appl. No. 10/465,759, filed Jun. 19, 2003, Bandaru et al., Non-Final Rejection, Jan. 8, 2004.
U.S. Appl. No. 09/723,685, filed Nov. 28, 2000, Abarzua, Issue Notification, Dec. 5, 2002.
U.S. Appl. No. 09/723,685, filed Nov. 28, 2000, Abarzua, Notice of Allowance, Apr. 17, 2002.
U.S. Appl. No. 09/723,685, filed Nov. 28, 2000, Abarzua, Response after Non-Final Action, Dec. 10, 2001.
U.S. Appl. No. 09/723,685, filed Nov. 28, 2000, Abarzua, Non-Final Rejection, Aug. 28, 2001.
U.S. Appl. No. 09/723,685, filed Nov. 28, 2000, Abarzua, Response after Non-Final Action, Jun. 15, 2001.
U.S. Appl. No. 09/723,685, filed Nov. 28, 2000, Abarzua, Non-Final Rejection, Mar. 13, 2001.
U.S. Appl. No. 10/196,539, filed Jul. 16, 2002, Abarzua, Issue Notification, Apr. 19, 2006.
U.S. Appl. No. 10/196,539, filed Jul. 16, 2002, Abarzua, Notice of Allowance, Nov. 15, 2003.
U.S. Appl. No. 10/196,539, filed Jul. 16, 2002, Abarzua, Terminal Disclaimer Filed, Aug. 12, 2005.
U.S. Appl. No. 10/196,539, filed Jul. 16, 2002, Abarzua, Response after Non-Final Action, Aug. 12, 2005.
U.S. Appl. No. 10/196,539, filed Jul. 16, 2002, Abarzua, Non-Final Rejection, Mar. 10, 2005.
U.S. Appl. No. 11/429,549, filed May 5, 2006, Abarzua, Examiner Interview Summary (PTOL 413), Oct. 15, 2008.
U.S. Appl. No. 11/429,549, filed May 5, 2006, Abarzua, Abandonment, Oct. 15, 2008.
U.S. Appl. No. 11/429,549, filed May 5, 2006, Abarzua, Non-Final Rejection, Mar. 26, 2008.
U.S. Appl. No. 11/429,549, filed May 5, 2006, Abarzua, Notice of Publication, Jan. 18, 2007.
U.S. Appl. No. 11/429,549, filed May 5, 2006, Abarzua, Preliminary Amendment, May 5, 2006.
U.S. Appl. No. 09/827,289, filed Apr. 5, 2001, Abarzua, Issue Notification, Jul. 29, 2004.
U.S. Appl. No. 09/827,289, filed Apr. 5, 2001, Abarzua, Notice of Allowance, Apr. 1, 2004.
U.S. Appl. No. 09/827,289, filed Apr. 5, 2001, Abarzua, Supplemental Response, Feb. 17, 2004.
U.S. Appl. No. 09/827,289, filed Apr. 5, 2001, Abarzua, Notice of Informal or Non-Responsive Amendment. Feb. 2, 2004.
U.S. Appl. No. 09/827,289, filed Apr. 5, 2001, Abarzua, Response after Non-Final Action, Jan. 22, 2004.
U.S. Appl. No. 09/827,289, filed Apr. 5, 2001, Abarzua, Non-Final Rejection, Sep. 29, 2003.
U.S. Appl. No. 09/827,289, filed Apr. 5, 2001, Abarzua, Request for Continued Examination (RCE), Aug. 6, 2003.
U.S. Appl. No. 09/827,289, filed Apr. 5, 2001, Abarzua, Advisory Action (PTOL-303), Jun. 2, 2003.
U.S. Appl. No. 09/827,289, filed Apr. 5, 2001, Abarzua, Amendment after Final Rejection, May 15, 2003.
U.S. Appl. No. 09/827,289, filed Apr. 5, 2001, Abarzua, Final Rejection (PTOL-326), Feb. 10, 2003.
U.S. Appl. No. 09/827,289, filed Apr. 5, 2001, Abarzua, Response after Non-Final Action, Jan. 21, 2003.
U.S. Appl. No. 09/827,289, filed Apr. 5, 2001, Abarzua, Non-Final Rejection, Jul. 29, 2002.
U.S. Appl. No. 09/827,289, filed Apr. 5, 2001, Abarzua, Response to Election / Restriction Filed, Jun. 24, 2002.
U.S. Appl. No. 09/827,289, filed Apr. 5, 2001, Abarzua, Restriction Requirement, Jun. 11, 2002.
U.S. Appl. No. 10/177,629, filed Jun. 19, 2002, Wiltshire, Examiner Interview Summary (PTOL-413), Sep. 20, 2007.
U.S. Appl. No. 10/177,629, filed Jun. 19, 2002, Wiltshire, Abandonment for failure to respond to office action, Sep. 15, 2007.
U.S. Appl. No. 10/177,629, filed Jun. 19, 2002, Wiltshire, Final Rejection (PTOL-326), Aug. 21, 2006.
U.S. Appl. No. 10/177,629, filed Jun. 19, 2002, Wiltshire, Response after Non-Final Action & Terminal Disclaimer, Jun. 12, 2006.
U.S. Appl. No. 10/177,629, filed Jun. 19, 2002, Wiltshire, Non-Final Rejection, Jan. 10, 2006.
U.S. Appl. No. 10/177,629, filed Jun. 19, 2002, Wiltshire, Response to Election / Responsive Amendment, Sep. 30, 2005.
U.S. Appl. No. 10/177,629, filed Jun. 19, 2002, Wiltshire, Notice of Informal or Non-Responsive Amendment, Sep. 30, 2005.
U.S. Appl. No. 10/177,629, filed Jun. 19, 2002, Wiltshire, Response to Election / Restriction Filed, Sep. 19, 2005.
U.S. Appl. No. 10/177,629, filed Jun. 19, 2002, Wiltshire, Restriction Requirement, Mar. 17, 2005.
U.S. Appl. No. 09/931,736, filed Aug. 17, 2001, Shao, Issue Notification, Feb. 9, 2005.
U.S. Appl. No. 09/931,736, filed Aug. 17, 2001, Shao, Notice of Allowance, Nov. 18, 2004.
U.S. Appl. No. 09/931,736, filed Aug. 17, 2001, Shao, Appeal Brief Filed, Aug. 27, 2004.
U.S. Appl. No. 09/931,736, filed Aug. 17, 2001, Shao, Advisory Action (PTOL-303), May 4, 2004.
U.S. Appl. No. 09/931,736, filed Aug. 17, 2001, Shao, Amendment/ Argument after Notice of Appeal, Mar. 1, 2004.
U.S. Appl. No. 09/931,736, filed Aug. 17, 2001, Shao, Notice of Appeal filed, Mar. 1, 2004.
U.S. Appl. No. 09/931,736, filed Aug. 17, 2001, Shao, Final Rejection (PTOL-326), Dec. 3, 2003.
U.S. Appl. No. 09/931,736, filed Aug. 17, 2001, Shao, Response after Non-Final Action, Sep. 22, 2003.
U.S. Appl. No. 09/931,736, filed Aug. 17, 2001, Shao, Non-Final Rejection, Jun. 30, 2003.
U.S. Appl. No. 09/931,736, filed Aug. 17, 2001, Shao, Response to Election / Restriction Filed, May 16, 2003.
U.S. Appl. No. 09/931,736, filed Aug. 17, 2001, Shao, Restriction Requirement, Apr. 15, 2003.
U.S. Appl. No. 10/931,015, filed Aug. 31, 2004, Shao, Abandonment for Failure to Respond to Office Action, Aug. 8, 2006.

U.S. Appl. No. 10/931,015, filed Aug. 31, 2004, Shao, Final Rejection (PTOL-326), Jan. 9, 2006.
U.S. Appl. No. 10/931,015, filed Aug. 31, 2004, Shao, Response after Non-Final Action, Aug. 26, 2005.
U.S. Appl. No. 10/931,015, filed Aug. 31, 2004, Shao, Non-Final Rejection, May 24, 2005.
U.S. Appl. No. 10/931,015, filed Aug. 31, 2004, Shao, Response to Election / Restriction Filed, Feb. 28, 2005.
U.S. Appl. No. 10/931,015, filed Aug. 31, 2004, Shao, Restriction Requirement, Jan. 24, 2005.
U.S. Appl. No. 11/870,715, filed Oct. 11, 2007, Korfhage et al., Response after Non-Final Action, Feb. 9, 2009.
U.S. Appl. No. 11/870,715, filed Oct. 11, 2007, Korfhage et al., Non-Final Rejection, Nov. 12, 2008.
U.S. Appl. No. 11/744,553, filed May 4, 2007, Korfhage et al., Amendment/Req. Reconsideration-After Non-Final Reje, Dec. 17, 2008.
U.S. Appl. No. 11/744,553, filed May 4, 2007, Korfhage et al., Examiner Interview Summary Record (PTOL-413), Dec. 15, 2008.
U.S. Appl. No. 11/744,553, filed May 4, 2007, Korfhage et al., Non-Final Rejection, Aug. 19, 2008.
U.S. Appl. No. 11/744,553, filed May 4, 2007, Korfhage et al., Response to Restriction Requirement, Jun. 5, 2008.
U.S. Appl. No. 11/744,553, filed May 4, 2007, Korfhage et al., Requirement for Restriction, May 16, 2008.
U.S. Appl. No. 11/744,553, filed May 4, 2007, Korfhage et al., Notice of Publication, Mar. 6, 2008.
U.S. Appl. No. 11/887,678, Korfhage, No Transaction History Generated.
U.S. Appl. No. 11/991,435, Korfhage, Preliminary Amendment, Mar. 3, 2008.
U.S. Appl. No. 08/563,912, filed Nov. 21, 1995, Lizardi, Issue Notification, Nov. 23, 1998.
U.S. Appl. No. 08/563,912, filed Nov. 21, 1995, Lizardi, Notice of Allowance, Aug. 14, 1998.
U.S. Appl. No. 08/563,912, filed Nov. 21, 1995, Lizardi, Examiner Interview Summary Record (PTOL-413), Aug. 10, 1998.
U.S. Appl. No. 08/563,912, filed Nov. 21, 1995, Lizardi, Amendment/Argument after Notice of Appeal, Aug. 6, 1998.
U.S. Appl. No. 08/563,912, filed Nov. 21, 1995, Lizardi, Notice of Appeal Filed, Jun. 15, 1998.
U.S. Appl. No. 08/563,912, filed Nov. 21, 1995, Lizardi, Final Rejection (PTOL-326), Dec. 9, 1997.
U.S. Appl. No. 08/563,912, filed Nov. 21, 1995, Lizardi, Response after Non-Final Action, Sep. 2, 1997.
U.S. Appl. No. 08/563,912, filed Nov. 21, 1995, Lizardi, Notice of Restarted Response Period, Feb. 28, 1997.
U.S. Appl. No. 08/563,912, filed Nov. 21, 1995, Lizardi, Non-Final Rejection, Feb. 7, 1997.
U.S. Appl. No. 08/563,912, filed Nov. 21, 1995, Lizardi, Response to Election / Restriction FIled, Oct. 31, 1996.
U.S. Appl. No. 08/563,912, filed Nov. 21, 1995, Lizardi, Restriction Requirement, Sep. 24, 1996.
U.S. Appl. No. 09/132,553, filed Aug. 11, 1998, Lizardi, Issue Notification, Mar. 15, 2001.
U.S. Appl. No. 09/132,553, filed Aug. 11, 1998, Lizardi, Notice of Allowance, Nov. 7, 2000.
U.S. Appl. No. 09/132,553, filed Aug. 11, 1998, Lizardi, Preliminary Amengment, Aug. 17, 2000.
U.S. Appl. No. 09/132,553, filed Aug. 11, 1998, Lizardi, Non-Final Rejection, Apr. 11, 2000.
U.S. Appl. No. 09/132,553, filed Aug. 11, 1998, Lizardi, Response after Non-Final Action & Terminal Disclaimer Filed, Jan. 19, 2000.
U.S. Appl. No. 09/132,553, filed Aug. 11, 1998, Lizardi, Non-Final Rejection, Sep. 13, 1999.
U.S. Appl. No. 09/644,723, filed Aug. 23, 2000, Lizardi, Issue Notification, Jan. 18, 2002.
U.S. Appl. No. 09/644,723, filed Aug. 23, 2000, Lizardi, Notice of Allowance, Oct. 1, 2001.
U.S. Appl. No. 09/644,723, filed Aug. 23, 2000, Lizardi, Response after Non-Final Action & Terminal Disclaimer Filed, Jul. 16, 2001.
U.S. Appl. No. 09/644,723, filed Aug. 23, 2000, Lizardi, Non-Final Rejection, Mar. 13, 2001.
U.S. Appl. No. 09/132,552, filed Aug. 11, 1998, Lizardi, Issue Notification, Jan. 19, 2001.
U.S. Appl. No. 09/132,552, filed Aug. 11, 1998, Lizardi, Notice of Allowance, Jul. 12, 2000.
U.S. Appl. No. 09/132,552, filed Aug. 11, 1998, Lizardi, Amendment after Final Rejection, Jun. 19, 2000.
U.S. Appl. No. 09/132,552, filed Aug. 11, 1998, Lizardi, Final Rejection (PTOL-326), Apr. 6, 2000.
U.S. Appl. No. 09/132,552, filed Aug. 11, 1998, Lizardi, Response after Non-Final Action & Terminal Disclaimer Filed, Jan. 19, 2000.
U.S. Appl. No. 09/132,552, filed Aug. 11, 1998, Lizardi, Non-Final Rejection, Sep. 13, 1999.
U.S. Appl. No. 10/038,718, filed Jan. 2, 2002, Lizardi, Issue Notification, Sep. 9, 2004.
U.S. Appl. No. 10/038,718, filed Jan. 2, 2002, Lizardi, Notice of Allowance, Apr. 21, 2004.
U.S. Appl. No. 10/038,718, filed Jan. 2, 2002, Lizardi, Response after Non-Final Action & Terminal Disclaimer Filed, Jan. 20, 2004.
U.S. Appl. No. 10/038,718, filed Jan. 2, 2002, Lizardi, Non-Final Rejection, Oct. 22, 2003.
U.S. Appl. No. 10/038,718, filed Jan. 2, 2002, Lizardi, Response to Election / Restriction Filed, Jul. 16, 2003.
U.S. Appl. No. 10/038,718, filed Jan. 2, 2002, Lizardi, Restriction Requirement, Mar. 13, 2003.
U.S. Appl. No. 08/946,732, filed Oct. 8, 1997, Lizardi, Issue Notification, Sep. 8, 2000.
U.S. Appl. No. 08/946,732, filed Oct. 8, 1997, Lizardi, Notice of Allowance, Jun. 22, 1999.
U.S. Appl. No. 08/946,732, filed Oct. 8, 1997, Lizardi, Examiner Interview Summary Record (PTOL-413), Jun. 9, 1999.
U.S. Appl. No. 08/946,732, filed Oct. 8, 1997, Lizardi, Response after Non-Final Action, Apr. 5, 1999.
U.S. Appl. No. 08/946,732, filed Oct. 8, 1997, Lizardi, Non-Final Rejection, Sep. 28, 1998.
U.S. Appl. No. 09/397,915, filed Sep. 17, 1999, Lizardi, Petition Decision—Accept Late Payment of Maintenance Feed—Granted, Oct. 31, 2005.
U.S. Appl. No. 09/397,915, filed Sep. 17, 1999, Lizardi, Petition to Accept Late Payment of Maintenance Fee Payment Filed, Oct. 13, 2005.
U.S. Appl. No. 09/397,915, filed Sep. 17, 1999, Lizardi, Expire Patent, Sep. 28, 2005.
U.S. Appl. No. 09/397,915, filed Sep. 17, 1999, Lizardi, Issue Notification, Aug. 9, 2001.
U.S. Appl. No. 09/397,915, filed Sep. 17, 1999, Lizardi, Notice of Allowance, Apr. 9, 2001.
U.S. Appl. No. 09/397,915, filed Sep. 17, 1999, Lizardi, Examiner Interview Summary Record (PTOL-413), Apr. 4, 2001.
U.S. Appl. No. 09/397,915, filed Sep. 17, 1999, Lizardi, Terminal Disclaimer Filed, Jan. 29, 2001.
U.S. Appl. No. 09/397,915, filed Sep. 17, 1999, Lizardi, Response after Non-Final Action, Jan. 22, 2001.
U.S. Appl. No. 09/397,915, filed Sep. 17, 1999, Lizardi, Non-Final Rejection, Aug. 14, 2000.
U.S. Appl. No. 09/911,226, filed Jul. 23, 2001, Lizardi, Issue Notification, Oct. 16, 2003.
U.S. Appl. No. 09/911,226, filed Jul. 23, 2001, Lizardi, Notice of Allowance, Jun. 3, 2003.
U.S. Appl. No. 09/911,226, filed Jul. 23, 2001, Lizardi, Response after Non-Final Action & Terminal Disclaimer Filed, Mar. 19, 2003.
U.S. Appl. No. 09/911,226, filed Jul. 23, 2001, Lizardi, Non-Final Rejection, Dec. 18, 2002.
U.S. Appl. No. 10/700,018, filed Nov. 3, 2003, Lizardi, Amendment after Final Rejection, Jan. 27, 2009.
U.S. Appl. No. 10/700,018, filed Nov. 3, 2003, Lizardi, Final Rejection, Sep. 15, 2008.
U.S. Appl. No. 10/700,018, filed Nov. 3, 2003, Lizardi, Amendment after Non-Final Rejection, Jun. 12, 2008.
U.S. Appl. No. 10/700,018, filed Nov. 3, 2003, Lizardi, Non-Final Rejection, Jan. 24, 2008.
U.S. Appl. No. 10/700,018, filed Nov. 3, 2003, Lizardi, Response after Non-Final Action, Oct. 31, 2007.

U.S. Appl. No. 10/700,018, filed Nov. 3, 2003, Lizardi, Non-Final Rejection, Aug. 8, 2007.
U.S. Appl. No. 10/700,018, filed Nov. 3, 2003, Lizardi, Response after Non-Final Action, May 14, 2007.
U.S. Appl. No. 10/700,018, filed Nov. 3, 2003, Lizardi, Non-Final Rejection, Nov. 14, 2006.
U.S. Appl. No. 10/700,018, filed Nov. 3, 2003, Lizardi, Response after Non-Final Action, Aug. 28, 2006.
U.S. Appl. No. 10/700,018, filed Nov. 3, 2003, Lizardi, Request for Extension of Time—Granted, Aug. 28, 2006.
U.S. Appl. No. 10/700,018, filed Nov. 3, 2003, Lizardi, Non-Final Requestion, May 18, 2006.
U.S. Appl. No. 10/700,018, filed Nov. 3, 2003, Lizardi, Preliminary Amendment, Nov. 3, 2003.
U.S. Appl. No. 09/357,487, filed Jul. 20, 1999, Lizardi, Issue Notification, Oct. 25, 2001.
U.S. Appl. No. 09/357,487, filed Jul. 20, 1999, Lizardi, Notice of Allowance, Jun. 5, 2001.
U.S. Appl. No. 09/357,487, filed Jul. 20, 1999, Lizardi, Examiner Interview Summary Record (PTOL-413), May 30, 2001.
U.S. Appl. No. 09/357,487, filed Jul. 20, 1999, Lizardi, Examiner Interview Summary Record (PTOL-413), May 28, 2001.
U.S. Appl. No. 09/357,487, filed Jul. 20, 1999, Lizardi, Amendment after Final Rejection, May 21, 2001.
U.S. Appl. No. 09/357,487, filed Jul. 20, 1999, Lizardi, Final Rejection (PTOL-326), Feb. 13, 2001.
U.S. Appl. No. 09/357,487, filed Jul. 20, 1999, Lizardi, Response after Non-Final Action, Jan. 29, 2001.
U.S. Appl. No. 09/357,487, filed Jul. 20, 1999, Lizardi, Non-Final Rejection, Oct. 25, 2000.
U.S. Appl. No. 09/357,487, filed Jul. 20, 1999, Lizardi, Response after Non-Final Action, Sep. 18, 2000.
U.S. Appl. No. 09/357,487, filed Jul. 20, 1999, Lizardi, Non-Final Rejection, May 12, 2000.
PCT/US02/026001, Jan. 30, 2002, Molecular Staging, Inc., International Preliminary Examination Report, Mar. 29, 2004.
PCT/US02/02601, Jan. 30, 2002, Molecular Staging, Inc., International Search Report, Oct. 3, 2002.
TW, 91102150, Feb. 7, 2002, Molecular Staging, Inc.
EP, 01928481.9, Apr. 12, 2001, Molecular Staging, Inc., Communiation under Rule 51(4) EPC, Sep. 11, 2007.
EP, 01928481.9, Apr. 12, 2001, Molecular Staging, Inc., Response to Examination Report, Nov. 27, 2006.
EP, 01928481.9, Apr. 12, 2001, Molecular Staging, Inc., Consultation by Telephone, Nov. 10, 2006.
EP, 01928481.9, Apr. 12, 2001, Molecular Staging, Inc., Response to Examination Report, Mar. 6, 2006.
EP, 01928481.9, Apr. 12, 2001, Molecular Staging, Inc., Examination Report, May 25, 2005.
PCT/US01/11947, Apr. 12, 2001, Molecular Staging, Inc., International Preliminary Examination Report, Apr. 30, 2003.
PCT/US01/11947, Apr. 12, 2001, Molecular Staging, Inc., International Search Report, Mar. 20, 2003.
AU, 2001255331, Apr. 12, 2001, Molecular Staging, Inc.
CA, 2405456, Apr. 12, 2001, Molecular Staging, Inc., Notice of Abandonment, Apr. 12, 2007.
CA, 2405456, Apr. 12, 2001, Molecular Staging, Inc., Notice of Reinstatement, 0/10/2005.
CA, 2405456, Apr. 12, 2001, Molecular Staging, Inc., Notice of Abandonment, Apr. 13, 2004.
CA, 2405456, Apr. 12, 2001, Molecular Staging, Inc., Notice of National Entry, Oct. 2, 2002.
CA, 2405456, Apr. 12, 2001, Molecular Staging, Inc., Notice of Abandonment.
JP, 2001-577404, Apr. 12, 2001, Molecular Staging, Inc.
AU, 2001269944, Jun. 20, 2001, Molecular Staging, Inc., Abandoned Application, Feb. 28, 2007.
AU, 2001269944, Jun. 20, 2001, Molecular Staging, Inc., Examination Report, May 29, 2006.
AU, 2001269944, Jun. 20, 2001, Molecular Staging, Inc., Response to Examination Report, May 16, 2006.
AU, 2001269944, Jun. 20, 2001, Molecular Staging, Inc., Molecular Staging, Inc., Examination Report, May 19, 2005.
CA, 2411838, Jun. 20, 2001, Molecular Staging, Inc., Notice of Abandonment, Jun. 20, 2007.
CA, 2411838, Jun. 20, 2001, Molecular Staging, Inc., Notice of National Entry, Dec. 12, 2002.
CN, 01811542.X, Jun. 20, 2001, Molecular Staging, Inc., Response to Examination Report, Nov. 23, 2005.
CN, 01811542.X, Jun. 20, 2001, Molecular Staging, Inc., Instructions for Responding to Aug. 7, 2005 Examination Report with List of Claims, Nov. 21, 2005.
CN, 01811542.X, Jun. 20, 2001, Molecular Staging, Inc., Examination Report, Aug. 7, 2005.
EP, 1948505.1, Jun. 20, 2001, Molecular Staging, Inc., Notification of European Publication, Feb. 19, 2003.
JP, 2002-503102, Jun. 20, 2001, Molecular Staging, Inc., Request for Examination, Jan. 11, 2007.
PCT/US01/19657, Jun. 20, 2001, Molecular Staging, Inc., International Preliminary Examination Report, Feb. 5, 2003.
PCT/US01/19657, Jun. 20, 2001, Molecular Staging, Inc., International Search Report, Dec. 27, 2001.
SG, 200207285-8, Jun. 20, 2001, Molecular Staging, Inc., Issue Notification, Dec. 16, 2002.
TW, 90114960, Jun. 28, 2001, Molecular Staging, Inc., Office Action, Oct. 3, 2005.
TW, 90114960, Jun. 28, 2001, Molecular Staging, Inc., Response to Office Action (no translation), Sep. 13, 2005.
TW, 90114960, Jun. 28, 2001, Molecular Staging, Inc., Instructions for Responding to May 16, 2005 Office Action with Issued Claims of US Patent No. 6,531,283 and Allowed Claims of U.S. Appl. No. 10/341,267, Jun. 30, 2005.
TW, 90114960, Jun. 28, 2001, Molecular Staging, Inc., Office Action, May 16, 2005.
AU, 2001271722, Jul. 2, 2001, Molecular Staging, Inc., Notice of Acceptance, Mar. 29, 2006.
AU, 2001271722, Jul. 2, 2001, Molecular Staging, Inc., Response to Examination Report, Mar. 17, 2006.
AU, 2001271722, Jul. 2, 2001, Molecular Staging, Inc., Examination Report, Jun. 17, 2005.
CA, 2411794, Jul. 2, 2001, Molecular Staging, Inc., Notice of Abandonment, Aug. 28, 2007.
CA, 2411794, Jul. 2, 2001, Molecular Staging, Inc., Notice of National Entry, Jan. 16, 2003.
DE, 1950759.9, Jul. 2, 2001, Molecular Staging, Inc.
EP, 01950759.9, Jul. 2, 2001, Molecular Staging, Inc., Decision to Grant, Sep. 6, 2007.
EP, 01950759.9, Jul. 2, 2001, Molecular Staging, Inc., Response to Communication under Rule 51(4), Aug. 17, 2007.
EP, 01950759.9, Jul. 2, 2001, Molecular Staging, Inc., Communications under Rule 51(4), Apr. 26, 2007.
EP, 01950759.9, Jul. 2, 2001, Molecular Staging, Inc., Response to Examination Report, Jul. 7, 2006.
EP, 01950759.9, Jul. 2, 2001, Molecular Staging, Inc., Response to Examination Report, Oct. 24, 2005.
EP, 01950759.9, Jul. 2, 2001, Molecular Staging, Inc., Examination Report, Jun. 16, 2005.
EP, 01950759.9, Jul. 2, 2001, Molecular Staging, Inc., European Search Report, Jul. 1, 2004.
JP, 2002-508032, Jul. 2, 2001, Molecular Staging, Inc., Application Open for Public Inspection, Jan. 29, 2004.
PCT/US01/20933, Jul. 2, 2001, Molecular Staging, Inc., Yale University, International Preliminary Examination Report, Dec. 30, 2002.
PCT/US01/20933, Jul. 2, 2001, Molecular Staging, Inc., Yale University, International Search Report, Jan. 10, 2002.
PCT/US02/15045, May 10, 2002, Molecular Staging, Inc., International Preliminary Examination Report, Oct. 26, 2004.
PCT/US02/15045, May 10, 2002, Molecular Staging, Inc., International Search Report, Apr. 10, 2003.
AU, 2002362874, Oct. 15, 2002, Molecular Staging, Inc., Examination Report, Jan. 8, 2007.
CA, 246933, Oct. 15, 2002, Molecular Staging, Inc., Notice of Abandonment, Dec. 10, 2007.
CA, 246933, Oct. 15, 2002, Molecular Staging, Inc., Notice of National Entry, Jun. 1, 2004.

EP, 02801776.2, Oct. 15, 2002, Molecular Staging, Inc., Response to Examination Report, Dec. 5, 2007.
EP, 02801776.2, Oct. 15, 2002, Molecular Staging, Inc., Examination Report, Aug. 7, 2007.
EP, 02801776.2, Oct. 15, 2002, Molecular Staging, Inc., European Search Report, Nov. 4, 2007.
EP, 02801776.2, Oct. 15, 2002, Molecular Staging, Inc., Letter Regarding European Search Report, Dec. 7, 2006.
EP, 02801776.2, Oct. 15, 2002, Molecular Staging, Inc., European Search Report, Nov. 7, 2006.
PCT/US02/33244, Oct. 15, 2002, Molecular Staging, Inc., International Preliminary Examination Report, Jul. 13, 2004.
PCT/US02/33244, Oct. 15, 2002, Molecular Staging, Inc., International Search Report, Apr. 29, 2004.
AU, 10240/97, Nov. 21, 1996, Yale University, Notice of Acceptance, Nov. 22, 1999.
AU, 10240/97, Nov. 21, 1996, Yale University, Response to Examination Report, Nov. 16, 1999.
AU, 10240/97, Nov. 21, 1996, Yale University, Examination Report, Apr. 30, 1999.
BE, 96940601.6, Nov. 21, 1996, Yale University, Notice of National Processing Completion, Apr. 20, 2001.
CH, 96940601.6, Nov. 21, 1996, Yale University.
DE, 826656, Nov. 21, 1996, Yale University, Patent Granted, Sep. 11, 2001.
DK, 96940601.6, Nov. 21, 1996, Yale University.
FR, 96940601.6, Nov. 21, 1996, Yale University.
GB, 96940601.6, Nov. 21, 1996, Yale University.
CA, 2236161, Nov. 21, 1996, Yale University, Notice of Allowance, Jun. 13, 2007.
CA, 2236161, Nov. 21, 1996, Yale University, Response to Examination Report, Oct. 4, 2006.
CA, 2236161, Nov. 21, 1996, Yale University, Examination Report, Apr. 4, 2006.
EP, 96940601.6, Nov. 21, 1996, Yale University, Decision to Grant, Jan. 25, 2001.
EP, 96940601.6, Nov. 21, 1996, Yale University, Response to Communication under Rule 51(4), Dec. 21, 1999.
EP, 96940601.6, Nov. 21, 1996, Yale University, Communication under Rule 51(4), Jul. 1, 1999.
JP, 9-519942, Nov. 21, 1996, Yale University, Letter from Foreign Associate re Notice of Allowance, May 30, 2007.
JP, 9-519942, Nov. 21, 1996, Yale University, Instructions for Responding to Jun. 27, 2006 Examination Report, Dec. 13, 2006.
JP, 9-519942, Nov. 21, 1996, Yale University, Examination Report, Jun. 27, 2006.
LU, 96940601.6, Nov. 21, 1996 Yale University.
MC, 96940601.6, Nov. 21, 1996, Yale University.
NL, 96940601.6, Nov. 21, 1996, Yale University.
PCT/US96/18812, Nov. 21, 1996, Yale University, International Preliminary Examination Report, Jan. 28, 1998.
PCT/US96/18812, Nov. 21, 1996, Yale University, International Search Report, Jun. 3, 1997.
PCT/US96/18812, Nov. 21, 1996, Yale University, Response to Written Opinion, Nov. 18, 1997.
PCT/US96/18812, Nov. 21, 1996, Yale University, Written Opinion, Aug. 21, 1997.
PCT/US96/18812, Nov. 21, 1996, Yale University, International Search Report, Nov. 21, 1995.
SE, 96940601.6, Nov. 21, 1996, Yale University.
PCT/US03/00678, Jan. 9, 2003, Molecular Staging, Inc., International Search Report, Aug. 14, 2003.
AU, 27819/00, Dec. 14, 1999, Molecular Staging, Inc., Deed of Letter.
AU, 27819/00, Dec. 14, 1999, Molecular Staging, Inc., Notice of Acceptance, May 12, 2005.
AU, 27819/00, Dec. 14, 1999, Molecular Staging, Inc., Response to Examination Report, Apr. 15, 2005.
AU, 27819/00, Dec. 14, 1999, Molecular Staging, Inc., Examination Report, Dec. 8, 2004.
AU, 27819/00, Dec. 14, 1999, Molecular Staging, Inc., Response to Examination Report, Nov. 30, 2004.
AU, 27819/00, Dec. 14, 1999, Molecular Staging, Inc., Examination Report, Oct. 14, 2004.
AU, 27819/00, Dec. 14, 1999, Molecular Staging, Inc., Response to Examination Report, Sep. 22, 2004.
AU, 27819/00, Dec. 14, 1999, Molecular Staging, Inc., Examination Report, Aug. 8, 2003.
CA, 2394800, Dec. 14, 1999, Molecular Staging, Inc., Notice of Abandonment, Feb. 11, 2008.
CA, 2394800, Dec. 14, 1999, Molecular Staging, Inc., Notice of Reinstatement, Jan. 5, 2005.
CA, 2394800, Dec. 14, 1999, Molecular Staging, Inc., Notice of Abandonment, Feb. 9, 2004.
CA, 2394800, Dec. 14, 1999, Molecular Staging, Inc., Notice of National Entry, Sep. 27, 2002.
EP, 99969209.8, Dec. 14, 1999, Molecular Staging, Inc., European Search Report, Feb. 21, 2003.
JP, 2000-588388, Dec. 14, 1999, Molecular Staging, Inc., Notice of Allowance, Jul. 22, 2008.
JP, 2000-588388, Dec. 14, 1999, Molecular Staging, Inc., Examination Report, Jul. 24, 2007.
PCT/AU99/01110, Dec. 14, 1999, Diatech Pty. Ltd., International Search Report, Jun. 22, 2000.
AU, 2003297891, Dec. 11, 2003, Qiagen GMBH.
CA, 2512196, Dec. 11, 2003, Qiagen GMGH, Notice of Abandonment, Feb. 8, 2008.
CA, 2512196, Dec. 11, 2003, Qiagen GMGH, Notice of National Entry, Oct. 3, 2005.
EP, 03796961.5, Dec. 11, 2003, Qiagen GMBH, Response to Examination Report, Oct. 26, 2007.
EP, 03796961.5, Dec. 11, 2003, Qiagen GMBH, Examination Report, Jun. 29, 2007.
EP, 03796961.5, Dec. 11, 2003, Qiagen GMBH, European Search Report, Jan. 16, 2007.
JP, 2004-565385, Dec. 11, 2003, Qiagen GMBH, Request for Examination, Nov. 22, 2006.
PCT/US03/39430, Dec. 11, 2003, Qiagen GMBH, International Search Report, Nov. 11, 2004.
AU, 2001268725, Jun. 27, 2001, Qiagen GMBH, Notice of Abandonment, Feb. 4, 2008.
AU, 2001268725, Jun. 27, 2001, Qiagen GMBH, Notice of Acceptance, Jul. 20, 2006.
AU, 2001268725, Jun. 27, 2001, Qiagen GMBH, Response to Examination Report, Jun. 23, 2006.
AU, 2001268725, Jun. 27, 2001, Qiagen GMBH, Examination Report, Jul. 18, 2005.
CA, 2410951, Jun. 27, 2001, Qiagen GMBH, Notice of Abandonment, Aug. 22, 2007.
CA, 2410951, Jun. 27, 2001, Qiagen GMBH, Notice of National Entry, Jan. 14, 2003.
DE, 01946712.5, Jun. 27, 2001, Qiagen GMBH.
EP, 01946712.5, Jun. 27, 2001, Molecular Staging, Inc., Decision to Grant, Sep. 21, 2006.
EP, 01946712.5, Jun. 27, 2001, Molecular Staging, Inc., Response to Communication under Rule 51(4), Aug. 18, 2006.
EP, 01946712.5, Jun. 27, 2001, Molecular Staging, Inc., Communication under Rule 51(4), Apr. 19, 2006.
EP, 01946712.5, Jun. 27, 2001, Molecular Staging, Inc., Response to Examination Report, Feb. 7, 2006.
EP, 01946712.5, Jun. 27, 2001, Molecular Staging, Inc., Observations by Third Parties, Jan. 23, 2006.
EP, 01946712.5, Jun. 27, 2001, Molecular Staging, Inc., Transmittal of Third Party Observations, Jan. 9, 2006.
EP, 01946712.5, Jun. 27, 2001, Molecular Staging, Inc., Observations by Third Parties, Dec. 28, 2005.
EP, 01946712.5, Jun. 27, 2001, Molecular Staging, Inc., Consultation by Phone, Dec. 15, 2005.
EP, 01946712.5, Jun. 27, 2001, Molecular Staging, Inc., Notification Concerning Date of Oral Proceedings, Dec. 6, 2005.
EP, 01946712.5, Jun. 27, 2001, Molecular Staging, Inc., Letter Dealing with Oral Proceedings, Nov. 29, 2005.
EP, 01946712.5, Jun. 27, 2001, Molecular Staging, Inc., Consultation by Phone, Nov. 16, 2005.

EP, 01946712.5, Jun. 27, 2001, Molecular Staging, Inc., Letter Dealing with Oral Proceedings, Oct. 31, 2005.
EP, 01946712.5, Jun. 27, 2001, Molecular Staging, Inc., Summons to attend Oral Proceedings, Jul. 1, 2005.
EP, 01946712.5, Jun. 27, 2001, Molecular Staging, Inc., Preparation for Oral Proceedings, Jun. 28, 2005.
EP, 01946712.5, Jun. 27, 2001, Molecular Staging, Inc., Response to Examination Report, Dec. 21, 2004.
EP, 01946712.5, Jun. 27, 2001, Molecular Staging, Inc., Examination Report, Nov. 11, 2004.
EP, 01946712.5, Jun. 27, 2001, Molecular Staging, Inc., Acknowledgment of Receipt of Third Party Observations, Oct. 29, 2004.
EP, 01946712.5, Jun. 27, 2001, Molecular Staging, Inc., Observations by Third Parties, Oct. 19, 2004.
EP, 01946712.5, Jun. 27, 2001, Molecular Staging, Inc., Response to Examination Report, Jul. 29, 2004.
EP, 01946712.5, Jun. 27, 2001, Molecular Staging, Inc., Examination Report, Mar. 19, 2004.
EP, 01946712.5, Jun. 27, 2001, Molecular Staging, Inc., Response to Examination Report, Jan. 30, 2004.
EP, 01946712.5, Jun. 27, 2001, Molecular Staging, Inc., Examination Report, Jul. 24, 2003.
FR, 01946712.5, Jun. 27, 2001, Molecular Staging, Inc.
GB, 01946712.5, Jun. 27, 2001, Molecular Staging, Inc.
IL, 153097, Jun. 27, 2001, Molecular Staging, Inc.
IT, 01946712.5, Jun. 27, 2001, Molecular Staging, Inc.
JP, 2002/506247, Jun. 27, 2001, Molecular Staging, Inc.
PCT/US01/20217, Jun. 27, 2001, Molecular Staging, Inc., International Preliminary Examination Report, Dec. 6, 2004.
PCT/US01/20217, Jun. 27, 2001, Molecular Staging, Inc., International Search Report, Apr. 3, 2003.
AU, 200253328, Jun. 12, 2000, Molecular Staging, Inc.
EPC, 938263.1, Jun. 12, 2000, Molecular Staging, Inc.
JP, 469290-19, Jun. 12, 2000, Molecular Staging, Inc.
PCT/US00/16130, Jun. 12, 2000, Molecular Staging, Inc., International Preliminary Examination Report, Dec. 28, 2004.
PCT/US00/16130, Jun. 12, 2000, Molecular Staging, Inc., International Search Report, Nov. 22, 2001.
AU, 2002/239809, Jan. 4, 2002, Molecular Staging, Inc.
CA, PCT/US02/00005, Jan. 4, 2002, Molecular Staging, Inc.
EPC, 2705674.6, Jan. 4, 2002, Molecular Staging, Inc.
PCT/US02/00005, Jan. 4, 2002, Molecular Staging, Inc., International Preliminary Examination Report, Jul. 5, 2003.
PCT/US02/00005, Jan. 4, 2002, Molecular Staging, Inc., International Search Report, May 22, 2003.
AU, 18040/01, Nov. 28, 2000, Molecular Staging, Inc.
CA, 2360342, Nov. 28, 2000, Molecular Staging, Inc.
EP, 00980827.0, Nov. 28, 2000, Molecular Staging, Inc., Response to Communication Pursuant to Rules 109 and 110 EPC, Oct. 17, 2001.
EP, 00980827.0, Nov. 28, 2000, Molecular Staging, Inc., Communication Pursuant to Rules 109 and 110 EPC, Sep. 13, 2001.
JP, 469290-68, Nov. 28, 2000, Molecular Staging, Inc.
PCT/US00/32370, Nov. 28, 2000, Molecular Staging, Inc., International Search Report, Jul. 11, 2002.
AU, 2001/251359, Apr. 5, 2001, Molecular Staging, Inc.
CA, 2405687, Apr. 5, 2001, Molecular Staging, Inc.
EPC, 1924731.1, Apr. 5, 2001, Molecular Staging, Inc.
JP, 2001-575244, Apr. 5, 2001, Molecular Staging, Inc.
PCT/US01/11151, Apr. 5, 2001, Molecular Staging, Inc., International Preliminary Examination Report, Oct. 15, 2004.
PCT/US01/11151, Apr. 5, 2001, Molecular Staging, Inc., International Search Report, Oct. 18, 2002.
PCT/US02/19443, Jun. 19, 2002, Molecular Staging, Inc., International Preliminary Examination Report, Feb. 16, 2006.
PCT/US02/19443, Jun. 19, 2002, Molecular Staging, Inc., International Search Report, Oct. 10, 2003.
PCT/US02/27097, Aug. 14, 2002, Molecular Staging, Inc., International Preliminary Examination Report, Oct. 12, 2004.
PCT/US02/27097, Aug. 14, 2002, Molecular Staging, Inc., International Search Report, Jan. 29, 2003.
EPC, 7118804.9, Oct. 18, 2007, Qiagen GMBH, European Search Report, Feb. 15, 2008.
AU, 97915/98, Oct. 8, 1998, Yale University, Issue Notification, Oct. 10, 2002.
AU, 97915/98, Oct. 18, 1998, Yale University, Notice of Acceptance, May 20, 2002.
AU, 97915/98, Oct. 8, 1998, Yale University, Response to Examination, Mar. 27, 2002.
AU, 97915/98, Oct. 8, 1998, Yale University, Examination Report, May 25, 2001.
CA, 2308004, Oct. 8, 1998, Yale University, Notice of Abandonment, Dec. 4, 2007.
CA, 2308004, Oct. 8, 1998, Yale University, Notice of Acceptance, Oct. 23, 2006.
CA, 2308004, Oct. 8, 1998, Yale University, Response to Examination, Dec. 23, 2004.
CA, 2308004, Oct. 8, 1998, Yale University, Examination Report, Jun. 30, 2004.
EP, 98952147.1, Oct. 8, 1998, Yale University, Decision to Grant, Dec. 6, 2007.
EP, 98952147.1, Oct. 8, 1998, Yale University, Response to Communication under Rule 51(4), Oct. 5, 2007.
EP, 98952147.1, Oct. 8, 1998, Yale University, Communication under Rule 51(4), Jun. 6, 2007.
EP, 98952147.1, Oct. 8, 1998, Yale University, Response to Examination Report, May 15, 2007.
EP, 98952147.1, Oct. 8, 1998, Yale University, Consultation by Phone, Apr. 16, 2007.
EP, 98952147.1, Oct. 8, 1998, Yale University, Response to Examination Report, Mar. 13, 2007.
EP, 98952147.1, Oct. 8, 1998, Yale University, Consultation by Phone, Dec. 29, 2006.
EP, 98952147.1, Oct. 8, 1998, Yale University, Response to Examination Report, Mar. 6, 2006.
EP, 98952147.1, Oct. 8, 1998, Yale University, Examination Report, Sep. 21, 2005.
JP, 2000-515033, Oct. 8, 1998, Yale University, Notice of Allowance, Feb. 3, 2009.
JP, 2000-515033, Oct. 8, 1998, Yale University, Argument and an Amendment to the outstanding Official Action, Dec. 22, 2008.
JP, 2000-515033, Oct. 8, 1998, Yale University, Notice of Rejection, Dec. 2, 2008.
JP, 2000-515033, Oct. 8, 1998, Yale University, Report Concerning Reconsideration by Examiner before Appeal, Oct. 2, 2007.
JP, 2000-515033, Oct. 8, 1998, Yale University, Letter from Foreign Associate re Filing Amendment and Response to Official Action, Mar. 24, 2006.
JP, 2000-515033, Oct. 8, 1998, Yale University, Instructions to Foreign Associate re Sep. 2, 2005, Final Rejection, Feb. 8, 2006.
JP, 2000-515033, Oct. 8, 1998, Yale University, Instructions to Foreign Associate re Sep. 2, 2005 Final Rejection, Dec. 2, 2005.
JP, 2000-515033, Oct. 8, 1998, Yale University, Final Rejection, Sep. 2, 2005.
JP, 2000-515033, Oct. 8, 1998, Yale University, Response to Examination (no translation), Nov. 11, 2004.
JP, 2000-515033, Oct. 8, 1998, Yale University, Instructions to Foreign Associate re May 7, 2004 Examination Report, Aug. 9, 2004.
JP, 2000-515033, Oct. 8, 1998, Yale University, Examination Report, May 7, 2004.
PCT/US98/21177, Oct. 8, 1998, Yale University, International Preliminary Examination Report, Oct. 12, 1999.
PCT/US98/21177, Oct. 8, 1998, Yale University, International Search Report, Apr. 15, 1999.
EP, 99935725.4, Jul. 20, 1999, Yale University, Examination Report, Aug. 13, 2003.
PCT/US99/16373, Jul. 20, 1999, Yale University, International Search Report, Nov. 9, 2000.

* cited by examiner

ROLLING CIRCLE AMPLIFICATION

LM-RCA FOLLOWED BY TRANSCRIPTION
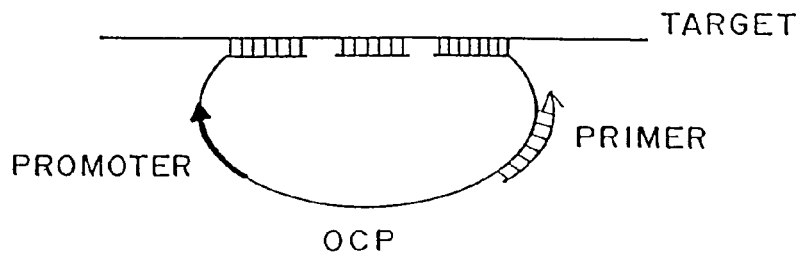
FIG. 8
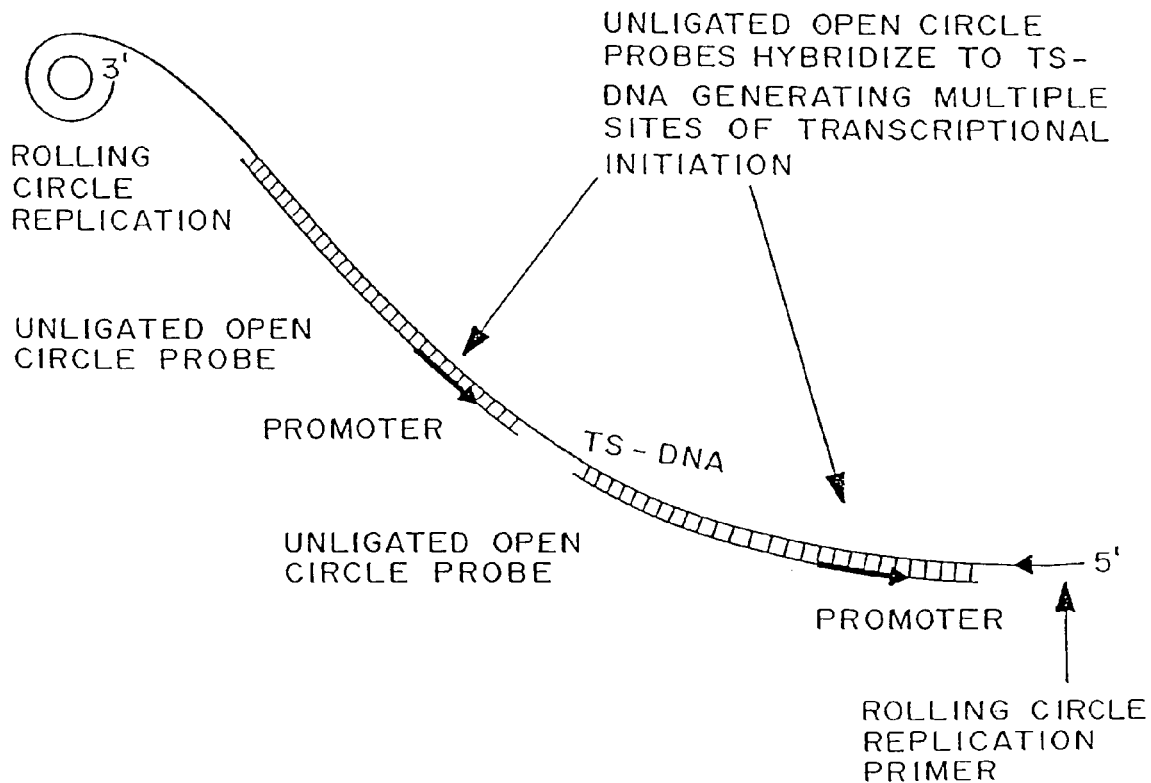

REPORTER ANTIBODIES

ASSAY

DETECTION EXAMPLE

DETECTION EXAMPLE

OPPOSITE STRAND AMPLIFICATION

ROLLING CIRCLE REPLICATION REPORTER SYSTEMS

CROSS-REFERENCE TO RELATED APPLICATIONS

This application is a continuation of U.S. patent application Ser. No. 10/038,718, filed on Jan. 2, 2002 now U.S. Pat. No. 6,797,474, which is a continuation of U.S. application Ser. No. 09/644,723, filed on Aug. 23, 2000 now U.S. Pat. No. 6,344,329, which is a continuation of U.S. patent application Ser. No. 09/132,553, filed Aug. 11, 1998 now U.S. Pat. No. 6,210,844, which is a continuation of U.S. patent application Ser. No. 08/563,912, filed Nov. 21, 1995 now U.S. Pat. No. 5,854,033, all of which are hereby incorporated by this reference in their entirety.

BACKGROUND OF THE INVENTION

The disclosed invention is generally in the field of assays for detection of analytes, and specifically in the field of nucleic acid amplification and detection.

A number of methods have been developed which permit the implementation of extremely sensitive diagnostic assays based on nucleic acid detection. Most of these methods employ exponential amplification of targets or probes. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117-126 (1991); Landegren, *Trends Genetics*, 9:199-202 (1993)).

While all of these methods offer good sensitivity, with a practical limit of detection of about 100 target molecules, all of them suffer from relatively low precision in quantitative measurements. This lack of precision manifests itself most dramatically when the diagnostic assay is implemented in multiplex format, that is, in a format designed for the simultaneous detection of several different target sequences.

In practical diagnostic applications it is desirable to assay for many targets simultaneously. Such multiplex assays are typically used to detect five or more targets. It is also desirable to obtain accurate quantitative data for the targets in these assays. For example, it has been demonstrated that viremia can be correlated with disease status for viruses such as HIV-1 and hepatitis C (Lefrere et al., *Br. J. Haematol.*, 82(2):467-471 (1992), Gunji et al., *Int. J. Cancer*, 52(5):726-730 (1992), Hagiwara et al., *Hepatology*, 17(4):545-550 (1993), Lu et al., *J. Infect. Dis.*, 168(5):1165-8116 (1993), Piatak et al., *Science*, 259(5102):1749-1754 (1993), Gupta et al., Ninth International Conference on AIDS/Fourth STD World Congress, Jun. 7-11, 1993, Berlin, Germany, Saksela et al., *Proc. Natl. Acad. Sci. USA*, 91(3):1104-1108 (1994)). A method for accurately quantitating viral load would be useful.

In a multiplex assay, it is especially desirable that quantitative measurements of different targets accurately reflect the true ratio of the target sequences. However, the data obtained using multiplexed, exponential nucleic acid amplification methods is at best semi-quantitative. A number of factors are involved:

1. When a multiplex assay involves different priming events for different target sequences, the relative efficiency of these events may vary for different targets. This is due to the stability and structural differences between the various primers used.
2. If the rates of product strand renaturation differ for different targets, the extent of competition with priming events will not be the same for all targets.
3. For reactions involving multiple ligation events, such as LCR, there may be small but significant differences in the relative efficiency of ligation events for each target sequence. Since the ligation events are repeated many times, this effect is magnified.
4. For reactions involving reverse transcription (3SR, NASBA) or klenow strand displacement (SDA), the extent of polymerization processivity may differ among different target sequences.
5. For assays involving different replicatable RNA probes, the replication efficiency of each probe is usually not the same, and hence the probes compete unequally in replication reactions catalyzed by Qβ replicase.
6. A relatively small difference in yield in one cycle of amplification results in a large difference in amplification yield after several cycles. For example, in a PCR reaction with 25 amplification cycles and a 10% difference in yield per cycle, that is, 2-fold versus 1.8-fold amplification per cycle, the yield would be $2.0^{25}=33,554,000$ versus $1.8^{25}=2,408,800$. The difference in overall yield after 25 cycles is 14-fold. After 30 cycles of amplification, the yield difference would be more than 20-fold.

Accordingly, there is a need for amplification methods that are less likely to produce variable and possibly erroneous signal yields in multiplex assays.

It is therefore an object of the disclosed invention to provide a method of amplifying diagnostic nucleic acids with amplification yields proportional to the amount of a target sequence in a sample.

It is another object of the disclosed invention to provide a method of detecting specific target nucleic acid sequences present in a sample where detection efficiency is not dependent on the structure of the target sequences.

It is another object of the disclosed invention to provide a method of determining the amount of specific target nucleic acid sequences present in a sample where the signal level measured is proportional to the amount of a target sequence in a sample and where the ratio of signal levels measured for different target sequences substantially matches the ratio of the amount of the different target sequences present in the sample.

It is another object of the disclosed invention to provide a method of detecting and determining the amount of multiple specific target nucleic acid sequences in a single sample where the ratio of signal levels measured for different target nucleic acid sequences substantially matches the ratio of the amount of the different target nucleic acid sequences present in the sample.

It is another object of the disclosed invention to provide a method of detecting the presence of single copies of target nucleic acid sequences in situ.

It is another object of the disclosed invention to provide a method of detecting the presence of target nucleic acid sequences representing individual alleles of a target genetic element.

SUMMARY OF THE INVENTION

Disclosed are compositions and a method for amplifying nucleic acid sequences based on the presence of a specific target sequence or analyte. The method is useful for detecting specific nucleic acids or analytes in a sample with high specificity and sensitivity. The method also has an inherently low level of background signal. Preferred embodiments of the method consist of a DNA ligation operation, an amplification operation, and, optionally, a detection operation. The DNA ligation operation circularizes a specially designed nucleic acid probe molecule. This step is dependent on hybridization of the probe to a target sequence and forms circular probe molecules in proportion to the amount of target sequence present in a sample. The amplification operation is rolling circle replication of the circularized probe. A single round of amplification using rolling circle replication results in a large amplification of the circularized probe sequences, orders of magnitude greater than a single cycle of PCR replication and other amplification techniques in which each cycle is limited to a doubling of the number of copies of a target sequence. Rolling circle amplification can also be performed independently of a ligation operation. By coupling a nucleic acid tag to a specific binding molecule, such as an antibody, amplification of the nucleic acid tag can be used to detect analytes in a sample. Optionally, an additional amplification operation can be performed on the DNA produced by rolling circle replication.

Following amplification, the amplified probe sequences can be detected and quantified using any of the conventional detection systems for nucleic acids such as detection of fluorescent labels, enzyme-linked detection systems, antibody-mediated label detection, and detection of radioactive labels. Since the amplified product is directly proportional to the amount of target sequence present in a sample, quantitative measurements reliably represent the amount of a target sequence in a sample. Major advantages of this method are that the ligation operation can be manipulated to obtain allelic discrimination, the amplification operation is isothermal, and signals are strictly quantitative because the amplification reaction is linear and is catalyzed by a highly processive enzyme. In multiplex assays, the primer oligonucleotide used for DNA replication can be the same for all probes.

The disclosed method has two features that provide simple, quantitative, and consistent amplification and detection of a target nucleic acid sequence. First, target sequences are amplified via a small diagnostic probe with an arbitrary primer binding sequence. This allows consistency in the priming and replication reactions, even between probes having very different target sequences. Second, amplification takes place not in cycles, but in a continuous, isothermal replication: rolling circle replication. This makes amplification less complicated and much more consistent in output.

BRIEF DESCRIPTION OF THE DRAWINGS

FIG. 8 is a diagram of an example of ligation-mediated rolling circle replication followed by transcription (LM-RCT). Diagramed at the top is a gap oligonucleotide and an open circle probe, having a primer complement portion and a promoter portion next to the right and left target probe portions, respectively, hybridized to a target sequence. Diagramed at the bottom is the rolling circle replication product hybridized to unligated copies of the open circle probe and gap oligonucleotide. This hybridization forms the double-stranded substrate for transcription.

FIG. 11B illustrates secondary DNA strand displacement carried out simultaneously with rolling circle replication.

DETAILED DESCRIPTION OF THE INVENTION

The disclosed composition and method make use of certain materials and procedures which allow consistent and quantitative amplification and detection of target nucleic acid sequences. These materials and procedures are described in detail below.

Some major features of the disclosed method are:
1. The ligation operation can be manipulated to obtain allelic discrimination, especially with the use of a gap-filling step.
2. The amplification operation is isothermal.
3. Signals can be strictly quantitative because in certain embodiments of the amplification operation amplification is linear and is catalyzed by a highly processive enzyme. In multiplex assays, the primer used for DNA replication is the same for all probes.
4. Modified nucleotides or other moieties may be incorporated during DNA replication or transcription.
5. The amplification product is a repetitive DNA molecule, and may contain arbitrarily chosen tag sequences that are useful for detection.

I. Materials

A. Open Circle Probes

Figure 5:
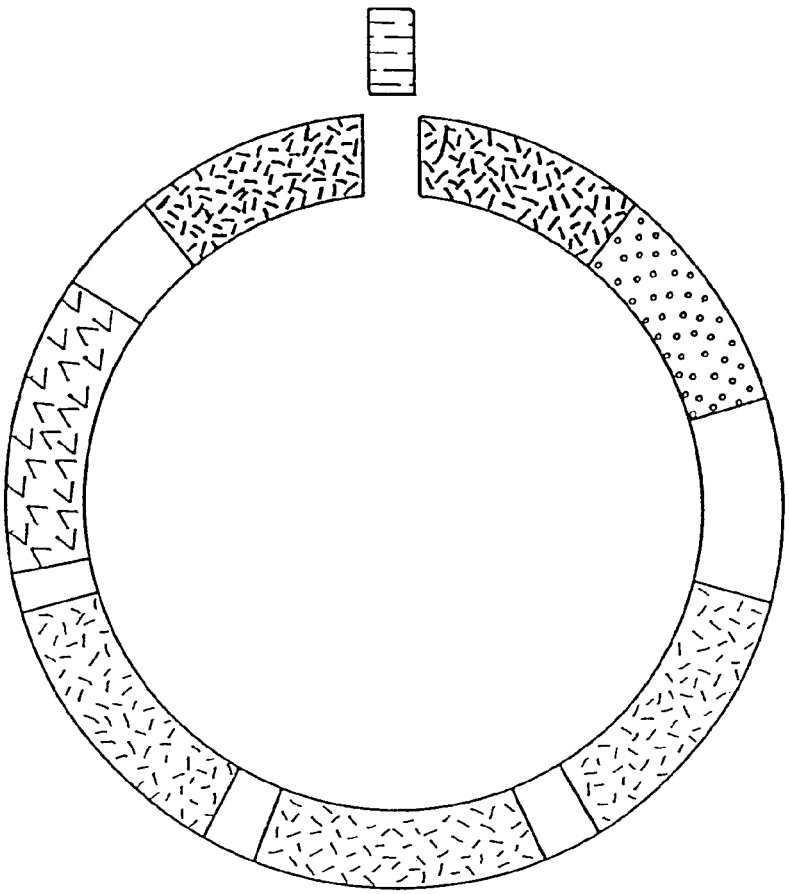
FIG. 5 is a diagram of an example of an open circle probe. Various portions of the open circle probe are indicated by different fills.

An open circle probe (OCP) is a linear single-stranded DNA molecule, generally containing between 50 to 1000 nucleotides, preferably between about 60 to 150 nucleotides, and most preferably between about 70 to 100 nucleotides. The OCP has a 5' phosphate group and a 3' hydroxyl group. This allows the ends to be ligated using a DNA ligase, or extended in a gap-filling operation. Portions of the OCP have specific functions making the OCP useful for RCA and LM-RCA. These portions are referred to as the target probe portions, the primer complement portion, the spacer region, the detection tag portions, the secondary target sequence portions, the address tag portions, and the promoter portion (FIG. 5). The target probe portions and the primer complement portion are required elements of an open circle probe. The primer complement portion is part of the spacer region. Detection tag portions, secondary target sequence portions, and promoter portions are optional and, when present, are part of the spacer region. Address tag portions are optional and, when present, may be part of the spacer region. Generally, an open circle probe is a single-stranded, linear DNA molecule comprising, from 5' end to 3' end, a 5' phosphate group, a right target probe portion, a spacer region, a left target probe portion, and a 3' hydroxyl group, with a primer complement portion present as part of the spacer region. Those segments of the spacer region that do not correspond to a specific portion of the OCP can be arbitrarily chosen sequences. It is preferred that OCPs do not have any sequences that are self-complementary. It is considered that this condition is met if there are no complementary regions greater than six nucleotides long without a mismatch or gap. It is also preferred that OCPs containing a promoter portion do not have any sequences that resemble a transcription terminator, such as a run of eight or more thymidine nucleotides.

The open circle probe, when ligated and replicated, gives rise to a long DNA molecule containing multiple repeats of sequences complementary to the open circle probe. This long DNA molecule is referred to herein as tandem sequences DNA (TS-DNA). TS-DNA contains sequences complementary to the target probe portions, the primer complement portion, the spacer region, and, if present on the open circle probe, the detection tag portions, the secondary target sequence portions, the address tag portions, and the promoter portion. These sequences in the TS-DNA are referred to as target sequences (which match the original target sequence), primer sequences (which match the sequence of the rolling circle replication primer), spacer sequences (complementary to the spacer region), detection tags, secondary target sequences, address tags, and promoter sequences.

A particularly preferred embodiment is an open circle probe of 70 to 100 nucleotides including a left target probe of 20 nucleotides and a right target probe of 20 nucleotides. The left target probe and right target probe hybridize to a target sequence leaving a gap of five nucleotides, which is filled by a single pentanucleotide gap oligonucleotide.

1. Target Probe Portions

There are two target probe portions on each OCP, one at each end of the OCP. The target probe portions can each be any length that supports specific and stable hybridization between the target probes and the target sequence. For this purpose, a length of 10 to 35 nucleotides for each target probe portion is preferred, with target probe portions 15 to 20 nucleotides long being most preferred. The target probe portion at the 3' end of the OCP is referred to as the left target probe, and the target probe portion at the 5' end of the OCP is referred to as the right target probe. These target probe portions are also referred to herein as left and right target probes or left and right probes. The target probe portions are complementary to a target nucleic acid sequence.

Figure 1:
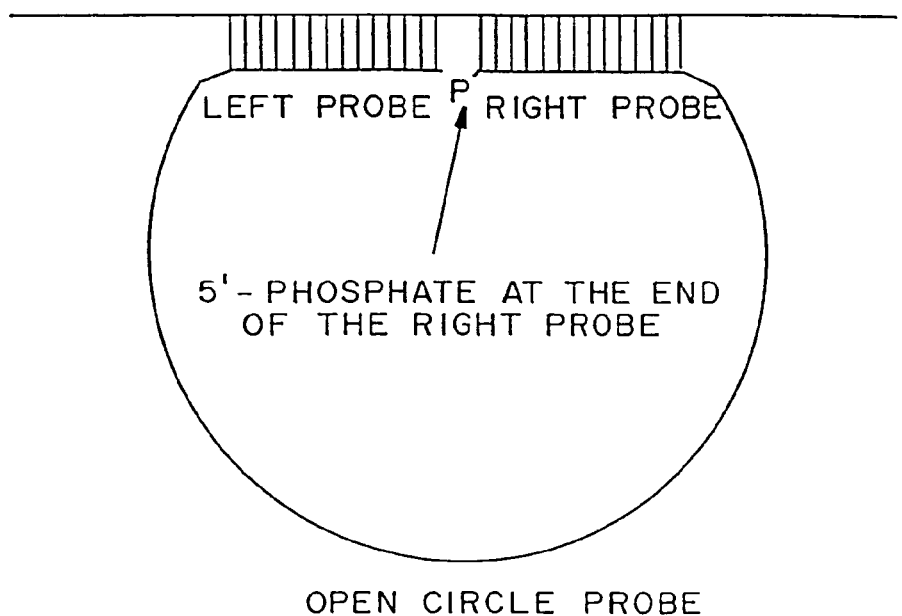
FIG. 1 is a diagram of an example of an open circle probe hybridized to a target sequence. The diagram shows the relationship between the target sequence and the right and left target probes.
Figure 2:
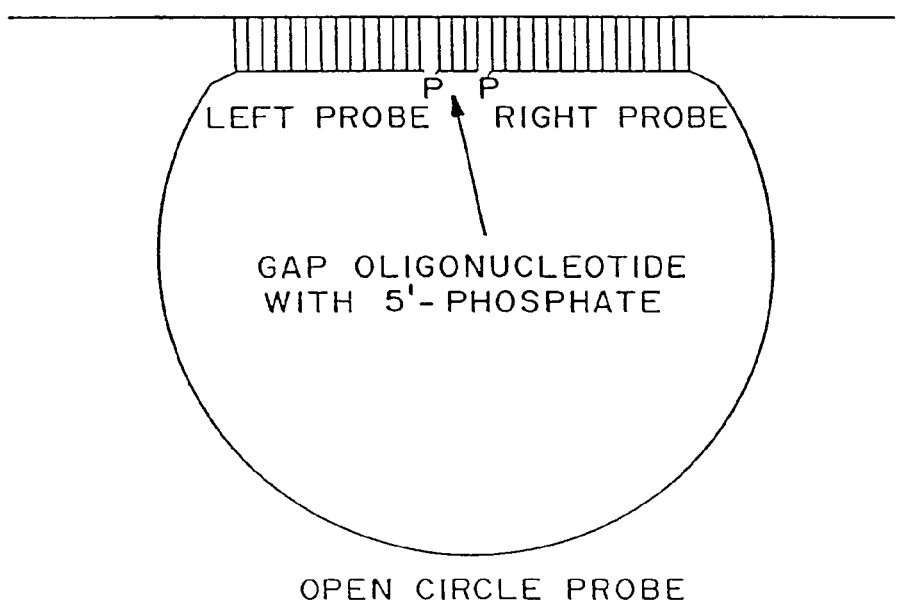
FIG. 2 is a diagram of an example of a gap oligonucleotide and an open circle probe hybridized to a target sequence. The diagram shows the relationship between the target sequence, the gap oligonucleotide, and the right and left target probes.
Figure 3:
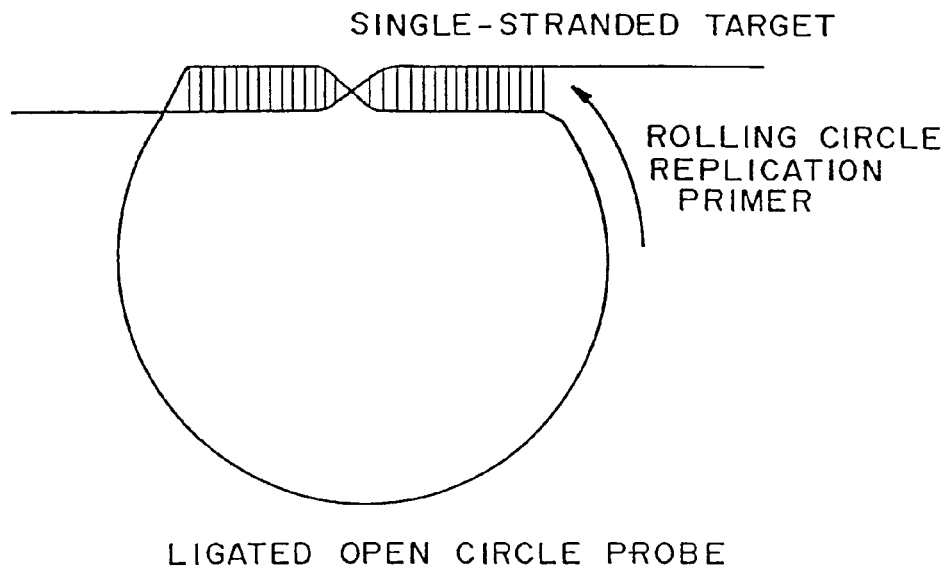
FIG. 3 is a diagram of an open circle probe hybridized and ligated to a target sequence. The diagram shows how the open circle probe becomes topologically locked to the target sequence.

The target probe portions are complementary to the target sequence, such that upon hybridization the 5' end of the right target probe portion and the 3' end of the left target probe portion are base-paired to adjacent nucleotides in the target sequence, with the objective that they serve as a substrate for ligation (FIG. 1). Optionally, the 5' end and the 3' end of the target probe portions may hybridize in such a way that they are separated by a gap space. In this case the 5' end and the 3' end of the OCP may only be ligated if one or more additional oligonucleotides, referred to as gap oligonucleotides, are used, or if the gap space is filled during the ligation operation. The gap oligonucleotides hybridize to the target sequence in the gap space to a form continuous probe/target hybrid (FIG. 2). The gap space may be any length desired but is generally ten nucleotides or less. It is preferred that the gap space is between about three to ten nucleotides in length, with a gap space of four to eight nucleotides in length being most preferred. Alternatively, a gap space could be filled using a DNA polymerase during the ligation operation (see Example 3). When using such a gap-filling operation, a gap space of three to five nucleotides in length being most preferred.

2. Primer Complement Portion

The primer complement portion is part of the spacer region of an open circle probe. The primer complement portion is complementary to the rolling circle replication primer (RCRP). Each OCP should have a single primer complement portion. This allows rolling circle replication to initiate at a single site on ligated OCPs. The primer complement portion and the cognate primer can have any desired sequence so long as they are complementary to each other. In general, the sequence of the primer complement can be chosen such that it is not significantly similar to any other portion of the OCP. The primer complement portion can be any length that supports specific and stable hybridization between the primer complement portion and the primer. For this purpose, a length of 10 to 35 nucleotides is preferred, with a primer complement portion 16 to 20 nucleotides long being most preferred. The primer complement portion can be located anywhere within the spacer region of an OCP. It is preferred that the primer complement portion is adjacent to the right target probe, with the right target probe portion and the primer complement portion preferably separated by three to ten nucleotides, and most preferably separated by six nucleotides. This location prevents the generation of any other spacer sequences, such as detection tags and secondary target sequences, from unligated open circle probes during DNA replication.

3. Detection Tag Portions

Detection tag portions are part of the spacer region of an open circle probe. Detection tag portions have sequences matching the sequence of the complementary portion of detection probes. These detection tag portions, when amplified during rolling circle replication, result in TS-DNA having detection tag sequences that are complementary to the complementary portion of detection probes. If present, there may be one, two, three, or more than three detection tag portions on an OCP. It is preferred that an OCP have two, three or four detection tag portions. Most preferably, an OCP will have three detection tag portions. Generally, it is preferred that an OCP have 60 detection tag portions or less. There is no fundamental limit to the number of detection tag portions that can be present on an OCP except the size of the OCP. When there are multiple detection tag portions, they may have the same sequence or they may have different sequences, with each different sequence complementary to a different detection probe. It is preferred that an OCP contain detection tag portions that have the same sequence such that they are all complementary to a single detection probe. The detection tag portions can each be any length that supports specific and stable hybridization between the detection tags and the detection probe. For this purpose, a length of 10 to 35 nucleotides is preferred, with a detection tag portion 15 to 20 nucleotides long being most preferred.

4. Secondary Target Sequence Portions

Secondary target sequence portions are part of the spacer region of an open circle probe. Secondary target sequence portions have sequences matching the sequence of target probes of a secondary open circle probe. These secondary target sequence portions, when amplified during rolling circle replication, result in TS-DNA having secondary target sequences that are complementary to target probes of a secondary open circle probe. If present, there may be one, two, or more than two secondary target sequence portions on an OCP. It is preferred that an OCP have one or two secondary target sequence portions. Most preferably, an OCP will have one secondary target sequence portion. Generally, it is preferred that an OCP have 50 secondary target sequence portions or less. There is no fundamental limit to the number of secondary target sequence portions that can be present on an OCP except the size of the OCP. When there are multiple secondary target sequence portions, they may have the same sequence or they may have different sequences, with each different sequence complementary to a different secondary OCP. It is preferred that an OCP contain secondary target sequence portions that have the same sequence such that they are all complementary to a single target probe portion of a secondary OCP. The secondary target sequence portions can each be any length that supports specific and stable hybridization between the secondary target sequence and the target sequence probes of its cognate OCP. For this purpose, a length of 20 to 70 nucleotides is preferred, with a secondary target sequence portion 30 to 40 nucleotides long being most preferred. As used herein, a secondary open circle probe is an open circle probe where the target probe portions match or are complementary to secondary target sequences in another open circle probe or an amplification target circle. It is contemplated that a secondary open circle probe can itself contain secondary target sequences that match or are complementary to the target probe portions of another secondary open circle probe. Secondary open circle probes related to each other in this manner are referred to herein as nested open circle probes.

5. Address Tag Portion

Figure 6:
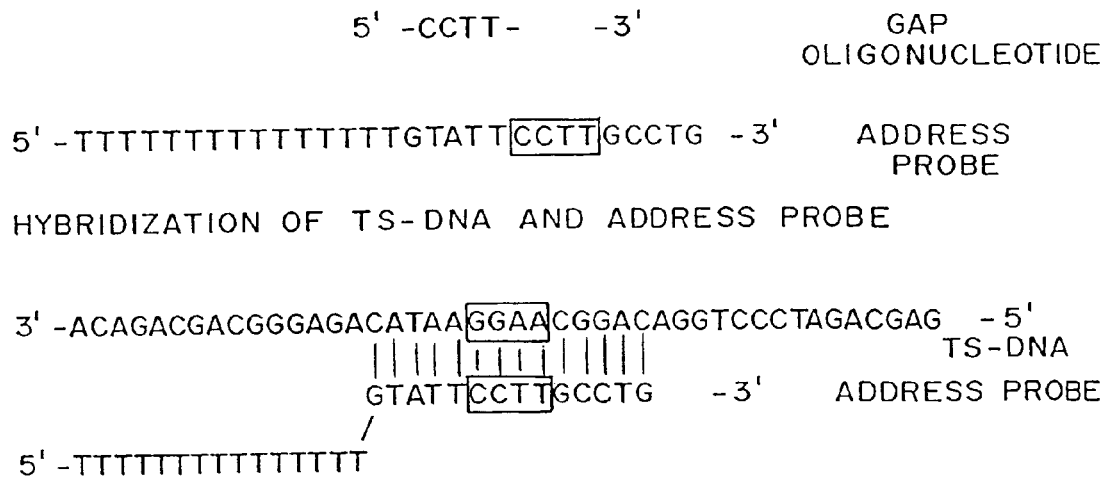
FIG. 6 is a diagram of tandem sequence DNA (TS-DNA) and an address probe designed to hybridize to the portion of the TS-DNA corresponding to part of the right and left target probes of the open circle probe and the gap oligonucleotide. The TS-DNA is SEQ ID NO:2 and the address probe is SEQ ID NO:3.

The address tag portion is part of either the target probe portions or the spacer region of an open circle probe. The address tag portion has a sequence matching the sequence of the complementary portion of an address probe. This address tag portion, when amplified during rolling circle replication, results in TS-DNA having address tag sequences that are complementary to the complementary portion of address probes. If present, there may be one, or more than one, address tag portions on an OCP. It is preferred that an OCP have one or two address tag portions. Most preferably, an OCP will have one address tag portion. Generally, it is preferred that an OCP have 50 address tag portions or less. There is no fundamental limit to the number of address tag portions that can be present on an OCP except the size of the OCP. When there are multiple address tag portions, they may have the same sequence or they may have different sequences, with each different sequence complementary to a different address probe. It is preferred that an OCP contain address tag portions that have the same sequence such that they are all complementary to a single address probe. Preferably, the address tag portion overlaps all or a portion of the target probe portions, and all of any intervening gap space (FIG. 6). Most preferably, the address tag portion overlaps all or a portion of both the left and right target probe portions. The address tag portion can be any length that supports specific and stable hybridization between the address tag and the address probe. For this purpose, a length between 10 and 35 nucleotides long is preferred, with an address tag portion 15 to 20 nucleotides long being most preferred.

6. Promoter Portion

The promoter portion corresponds to the sequence of an RNA polymerase promoter. A promoter portion can be included in an open circle probe so that transcripts can be generated from TS-DNA. The sequence of any promoter may be used, but simple promoters for RNA polymerases without complex requirements are preferred. It is also preferred that the promoter is not recognized by any RNA polymerase that may be present in the sample containing the target nucleic acid sequence. Preferably, the promoter portion corresponds to the sequence of a T7 or SP6 RNA polymerase promoter. The T7 and SP6 RNA polymerases are highly specific for particular promoter sequences. Other promoter sequences specific for RNA polymerases with this characteristic would also be preferred. Because promoter sequences are generally recognized by specific RNA polymerases, the cognate polymerase for the promoter portion of the OCP should be used for transcriptional amplification. Numerous promoter sequences are known and any promoter specific for a suitable RNA polymerase can be used. The promoter portion can be located anywhere within the spacer region of an OCP and can be in either orientation. Preferably, the promoter portion is immediately adjacent to the left target probe and is oriented to promote transcription toward the 3' end of the open circle probe. This orientation results in transcripts that are complementary to TS-DNA, allowing independent detection of TS- DNA and the transcripts, and prevents transcription from interfering with rolling circle replication.

B. Gap Oligonucleotides

Gap oligonucleotides are oligonucleotides that are complementary to all or a part of that portion of a target sequence which covers a gap space between the ends of a hybridized open circle probe. An example of a gap oligonucleotide and its relationship to a target sequence and open circle probe is shown in FIG. 2. Gap oligonucleotides have a phosphate group at their 5' ends and a hydroxyl group at their 3' ends. This facilitates ligation of gap oligonucleotides to open circle probes, or to other gap oligonucleotides. The gap space between the ends of a hybridized open circle probe can be filled with a single gap oligonucleotide, or it can be filled with multiple gap oligonucleotides. For example, two 3 nucleotide gap oligonucleotides can be used to fill a six nucleotide gap space, or a three nucleotide gap oligonucleotide and a four nucleotide gap oligonucleotide can be used to fill a seven nucleotide gap space. Gap oligonucleotides are particularly useful for distinguishing between closely related target sequences. For example, multiple gap oligonucleotides can be used to amplify different allelic variants of a target sequence. By placing the region of the target sequence in which the variation occurs in the gap space formed by an open circle probe, a single open circle probe can be used to amplify each of the individual variants by using an appropriate set of gap oligonucleotides.

C. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides. Ligated open circle probes are a type of ATC, and as used herein the term amplification target circle includes ligated open circle probes. An ATC can be used in the same manner as described herein for OCPs that have been ligated.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as tags for specific binding molecules.

D. Rolling Circle Replication Primer

A rolling circle replication primer (RCRP) is an oligonucleotide having sequence complementary to the primer complement portion of an OCP or ATC. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the OCP or ATC. The complementary portion of a rolling circle replication primer can be any length that supports specific and stable hybridization between the primer and the primer complement portion. Generally this is 10 to 35 nucleotides long, but is preferably 16 to 20 nucleotides long.

It is preferred that rolling circle replication primers also contain additional sequence at the 5' end of the RCRP that is not complementary to any part of the OCP or ATC. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. The rolling circle replication primer may also include modified nucleotides to make it resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. A rolling circle replication primer can be used as the tertiary DNA strand displacement primer in strand displacement cascade amplification.

E. Detection Labels

To aid in detection and quantitation of nucleic acids amplified using RCA and RCT, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid or antibody probes are known to those of skill in the art. Examples of detection labels suitable for use in RCA and RCT are radioactive isotopes, fluorescent molecules, phosphorescent molecules, enzymes, antibodies, and ligands.

Examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources, including Molecular Probes, Eugene, Oreg. and Research Organics, Cleveland, Ohio.

Labeled nucleotides are preferred form of detection label since they can be directly incorporated into the products of RCA and RCT during synthesis. Examples of detection labels that can be incorporated into amplified DNA or RNA include nucleotide analogs such as BrdUrd (Hoy and Schimke, *Muta-*

*tion Research* 290:217-230 (1993)), BrUTP (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim).

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3,3,1,1$^{3,7}$]decane]-4-yl)phenyl phosphate; Tropix, Inc.).

A preferred detection label for use in detection of amplified RNA is acridinium-ester-labeled DNA probe (GenProbe, Inc., as described by Arnold et al., *Clinical Chemistry* 35:1588-1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled.

F. Detection Probes

Detection probes are labeled oligonucleotides having sequence complementary to detection tags on TS-DNA or transcripts of TS-DNA. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized. The use of such probes eliminates the need for removal of unhybridized probes prior to label detection because the unhybridized detection probes will not produce a signal. This is especially useful in multiplex assays.

G. Address Probes

An address probe is an oligonucleotide having a sequence complementary to address tags on TS-DNA or transcripts of TS-DNA. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. Preferably, the complementary portion of an address probe is complementary to all or a portion of the target probe portions of an OCP. Most preferably, the complementary portion of an address probe is complementary to a portion of either or both of the left and right target probe portions of an OCP and all or a part of any gap oligonucleotides or gap sequence created in a gap-filling operation (see FIG. 6). Address probe can contain a single complementary portion or multiple complementary portions. Preferably, address probes are coupled, either directly or via a spacer molecule, to a solid-state support. Such a combination of address probe and solid-state support are a preferred form of solid-state detector.

H. DNA Strand Displacement Primers

Primers used for secondary DNA strand displacement are referred to herein as DNA strand displacement primers. One form of DNA strand displacement primer, referred to herein as a secondary DNA strand displacement primer, is an oligonucleotide having sequence matching part of the sequence of an OCP or ATC. This sequence is referred to as the matching portion of the secondary DNA strand displacement primer. This matching portion of a secondary DNA strand displacement primer is complementary to sequences in TS-DNA. The matching portion of a secondary DNA strand displacement primer may be complementary to any sequence in TS-DNA. However, it is preferred that it not be complementary TS-DNA sequence matching either the rolling circle replication primer or a tertiary DNA strand displacement primer, if one is being used. This prevents hybridization of the primers to each other. The matching portion of a secondary DNA strand displacement primer may be complementary to all or a portion of the target sequence. In this case, it is preferred that the 3' end nucleotides of the secondary DNA strand displacement primer are complementary to the gap sequence in the target sequence. It is most preferred that nucleotide at the 3' end of the secondary DNA strand displacement primer falls complementary to the last nucleotide in the gap sequence of the target sequence, that is, the 5' nucleotide in the gap sequence of the target sequence. The matching portion of a secondary DNA strand displacement primer can be any length that supports specific and stable hybridization between the primer and its complement. Generally this is 12 to 35 nucleotides long, but is preferably 18 to 25 nucleotides long.

It is preferred that secondary DNA strand displacement primers also contain additional sequence at their 5' end that does not match any part of the OCP or ATC. This sequence is referred to as the non-matching portion of the secondary DNA strand displacement primer. The non-matching portion of the secondary DNA strand displacement primer, if present, serves to facilitate strand displacement during DNA replication. The non-matching portion of a secondary DNA strand displacement primer may be any length, but is generally 1 to 100 nucleotides long, and preferably 4 to 8 nucleotides long.

Another form of DNA strand displacement primer, referred to herein as a tertiary DNA strand displacement primer, is an oligonucleotide having sequence complementary to part of the sequence of an OCP or ATC. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the OCP or ATC. However, it is preferred that it not be complementary OCP or ATC sequence matching the secondary DNA strand displacement primer. This prevents hybridization of the primers to each other. Preferably, the complementary portion of the tertiary DNA strand displacement primer has sequence complementary to a portion of the spacer portion of an OCP. The complementary portion of a tertiary DNA strand displacement primer can be any length that supports specific and stable hybridization between the primer and its complement. Generally this is 12 to 35 nucleotides long, but is preferably 18 to 25 nucleotides long. It is preferred that tertiary DNA strand displacement primers also contain additional sequence at their 5' end that is not complementary to any part of the OCP or ATC. This sequence is referred to as the non-complementary portion of the tertiary DNA strand displacement primer. The non-complementary portion of the tertiary DNA strand displacement primer, if present, serves to facilitate strand displacement during DNA replication. The non-complementary portion of a tertiary DNA strand displacement primer may be any length, but is generally 1 to 100 nucleotides long, and preferably 4 to 8 nucleotides long. A rolling circle replication primer is a preferred form of tertiary DNA strand displacement primer.

DNA strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. DNA strand displacement primers can be used for secondary DNA strand displacement and strand displacement cascade amplification, both described below.

I. Peptide Nucleic Acid Clamps

Peptide nucleic acids (PNA) are a modified form of nucleic acid having a peptide backbone. Peptide nucleic acids form extremely stable hybrids with DNA (Hanvey et al., *Science* 258:1481-1485 (1992); Nielsen et al., *Anticancer Drug Des.* 8:53-63 (1993)), and have been used as specific blockers of PCR reactions (Orum et al., *Nucleic Acids Res.*, 21:5332-5336 (1993)). PNA clamps are peptide nucleic acids complementary to sequences in both the left target probe portion and right target probe portion of an OCP, but not to the sequence of any gap oligonucleotides or filled gap space in the ligated OCP. Thus, a PNA clamp can hybridize only to the ligated junction of OCPs that have been illegitimately ligated, that is, ligated in a non-target-directed manner. The PNA clamp can be any length that supports specific and stable hybridization between the clamp and its complement. Generally this is 7 to 12 nucleotides long, but is preferably 8 to 10 nucleotides long. PNA clamps can be used to reduce background signals in rolling circle amplifications by preventing replication of illegitimately ligated OCPs.

J. Oligonucleotide Synthesis

Open circle probes, gap oligonucleotides, rolling circle replication primers, detection probes, address probes, amplification target circles, DNA strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

K. Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Address probes immobilized on a solid-state substrate allow capture of the products of RCA and RCT on a solid-state detector. Such capture provides a convenient means of washing away reaction components that might interfere with subsequent detection steps. By attaching different address probes to different regions of a solid-state detector, different RCA or RCT products can be captured at different, and therefore diagnostic, locations on the solid-state detector. For example, in a microtiter plate multiplex assay, address probes specific for up to 96 different TS-DNAs (each amplified via a different target sequence) can be immobilized on a microtiter plate, each in a different well. Capture and detection will occur only in those wells corresponding to TS-DNAs for which the corresponding target sequences were present in a sample.

Methods for immobilization of oligonucleotides to solid-state substrates are well established. Oligonucleotides, including address probes and detection probes, can be coupled to substrates using established coupling methods.

For example, suitable attachment methods are described by Pease et al., *Proc. Natl. Acad. Sci. USA* 91(11):5022-5026 (1994), and Khrapko et al., *Mol Biol (Mosk) (USSR)* 25:718-730 (1991). A method for immobilization of 3'-amine oligonucleotides on casein-coated slides is described by Stimpson et al., *Proc. Natl. Acad. Sci. USA* 92:6379-6383 (1995). A preferred method of attaching oligonucleotides to solid-state substrates is described by Guo et al., *Nucleic Acids Res.* 22:5456-5465 (1994).

Some solid-state detectors useful in RCA and RCT assays have detection antibodies attached to a solid-state substrate. Such antibodies can be specific for a molecule of interest. Captured molecules of interest can then be detected by binding of a second, reporter antibody, followed by RCA or RCT. Such a use of antibodies in a solid-state detector allows RCA assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), and Johnstone and Thorpe, *Immunochemistry In Practice* (Blackwell Scientific Publications, Oxford, England, 1987) pages 209-216 and 241-242. Antibodies can be attached to a substrate by chemically cross-linking a free amino group on the antibody to reactive side groups present within the solid-state substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

L. Reporter Binding Agents

A reporter binding agent is a specific binding molecule coupled or tethered to an oligonucleotide. The specific binding molecule is referred to as the affinity portion of the reporter binding agent and the oligonucleotide is referred to as the oligonucleotide portion of the reporter binding agent. As used herein, a specific binding molecule is a molecule that interacts specifically with a particular molecule or moiety. Antibodies, either member of a receptor/ligand pair, and other molecules with specific binding affinities are examples of specific binding molecules, useful as the affinity portion of a reporter binding molecule. By tethering an amplification target circle or coupling a target sequence to such specific binding molecules, binding of a specific binding molecule to its specific target can be detected by amplifying the ATC or target sequence with rolling circle amplification. This amplification allows sensitive detection of a very small number of bound specific binding molecules.

In one embodiment, the oligonucleotide portion of a reporter binding agent includes a sequence, referred to as a target sequence, that serves as a target sequence for an OCP. The sequence of the target sequence can be arbitrarily chosen.

In a multiplex assay using multiple reporter binding agents, it is preferred that the target sequence for each reporter binding agent be substantially different to limit the possibility of non-specific target detection. Alternatively, it may be desirable in some multiplex assays, to use target sequences with related sequences. By using different, unique gap oligonucleotides to fill different gap spaces, such assays can use one or a few OCPs to amplify and detect a larger number of target sequences. The oligonucleotide portion can be coupled to the affinity portion by any of several established coupling reactions. For example, Hendrickson et al., *Nucleic Acids Res.*, 23(3):522-529 (1995) describes a suitable method for coupling oligonucleotides to antibodies.

In another embodiment, the oligonucleotide portion of a reporter binding agent can include an amplification target circle which serves as a template for rolling circle replication. In a multiplex assay using multiple reporter binding agents, it is preferred that address tag portions and detection tag portions of the ATC comprising the oligonucleotide portion of each reporter binding agent be substantially different to unique detection of each reporter binding agent. It is desirable, however, to use the same primer complement portion in all of the ATCs used in a multiplex assay. The ATC is tethered to the specific binding molecule by looping the ATC around a tether loop. This allows the ATC to rotate freely during rolling circle replication while remaining coupled to the affinity portion. The tether loop can be any material that can form a loop and be coupled to a specific binding molecule. Linear polymers are a preferred material for tether loops.

A preferred method of producing a reporter binding agent with a tethered ATC is to form the tether loop by ligating the ends of oligonucleotides coupled to a specific binding molecule around an ATC. Oligonucleotides can be coupled to specific binding molecules using known techniques. For example, Hendrickson et al. (1995), describes a suitable method for coupling oligonucleotides to antibodies. This method is generally useful for coupling oligonucleotides to any protein. To allow ligation, oligonucleotides comprising the two halves of the tether loop should be coupled to the specific binding molecule in opposite orientations such that the free end of one is the 5' end and the free end of the other is the 3' end. Ligation of the ends of the tether oligonucleotides can be mediated by hybridization of the ends of the tether oligonucleotides to adjacent sequences in the ATC to be tethered. In this way, the ends of the tether oligonucleotides are analogous to the target probe portions of an open circle probe, with the ATC containing the target sequence.

Another preferred method of producing a reporter binding agent with a tethered ATC is to ligate an open circle probe while hybridized to an oligonucleotide tether loop on a specific binding molecule. This is analogous to the ligation operation of LM-RCA. In this case, the target sequence is part of an oligonucleotide with both ends coupled to a specific binding molecule. In this method, both ends of a single tether oligonucleotide are coupled to a specific binding molecule. This can be accomplished using known coupling techniques as described above.

The ends of tether loops can be coupled to any specific binding molecule with functional groups that can be derivatized with suitable activating groups. When the specific binding molecule is a protein, or a molecule with similar functional groups, coupling of tether ends can be accomplished using known methods of protein attachment. Many such methods are described in *Protein immobilization: fundamentals and applications* Richard F. Taylor, ed. (M. Dekker, New York, 1991).

Antibodies useful as the affinity portion of reporter binding agents, can be obtained commercially or produced using well established methods. For example, Johnstone and Thorpe, on pages 30-85, describe general methods useful for producing both polyclonal and monoclonal antibodies. The entire book describes many general techniques and principles for the use of antibodies in assay systems.

M. DNA Ligases

Any DNA ligase is suitable for use in the disclosed amplification method. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590-4592 (1978)), AMPLIGASE® (Kalin et al., *Mutat. Res.*, 283(2):119-123 (1992); Winn-Deen et al., *Mol Cell Probes* (England) 7(3):179-186 (1993)), Taq DNA ligase (Barany, *Proc. Natl. Acad. Sci. USA* 88:189-193 (1991), *Thermus thermophilus* DNA ligase (Abbott Laboratories), *Thermus scotoductus* DNA ligase and *Rhodothermus marinus* DNA ligase (Thorbjarnardottir et al., *Gene* 151:177-180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction*, American Association for the Study of Liver Diseases (Chicago, Ill., Nov. 3-7, 1995)).

The frequency of non-target-directed ligation catalyzed by a ligase can be determined as follows. LM-RCA is performed with an open circle probe and a gap oligonucleotide in the presence of a target sequence. Non-targeted-directed ligation products can then be detected by using an address probe specific for the open circle probe ligated without the gap oligonucleotide to capture TS-DNA from such ligated probes. Target directed ligation products can be detected by using an address probe specific for the open circle probe ligated with the gap oligonucleotide. By using a solid-state detector with regions containing each of these address probes, both target directed and non-target-directed ligation products can be detected and quantitated. The ratio of target-directed and non-target-directed TS-DNA produced provides a measure of the specificity of the ligation operation. Target-directed ligation can also be assessed as discussed in Barany (1991).

N. DNA Polymerases

DNA polymerases useful in the rolling circle replication step of RCA must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ligated OCP. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), VENT® DNA polymerase (Kong et al., *J. Biol. Chem.* 268:1965-1975 (1993)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), PRD1 DNA polymerase (Zhu and Ito, *Biochim. Biophys. Acta*. 1219:267-276 (1994)), and T4 DNA polymerase holoenzyme (Kaboord and Benkovic, *Curr. Biol.* 5:149-157 (1995)). φ29 DNA polymerase is most preferred.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include BMRF1 polymerase accessory subunit (Tsurumi et al., *J. Virology* 67(12):7648-7653 (1993)), adenovirus DNA-binding protein (Zijderveld and van der Vliet, *J. Virology* 68(2): 1158-1164 (1994)), herpes simplex viral protein ICP8 (Boehmer and Lehman, *J. Virology* 67(2):711-715 (1993); Skaliter and Lehman, *Proc. Natl. Acad. Sci. USA* 91(22):10665-10669 (1994)), single-stranded DNA binding proteins (SSB; Rigler and Romano, *J. Biol. Chem.* 270:8910-8919 (1995)), and calf thymus helicase (Siegel et al., *J. Biol. Chem.* 267:13629-13635 (1992)).

The ability of a polymerase to carry out rolling circle replication can be determined by using the polymerase in a rolling circle replication assay such as those described in Fire and Xu, *Proc. Natl. Acad. Sci. USA* 92:4641-4645 (1995) and in Example 1.

Another type of DNA polymerase can be used if a gap-filling synthesis step is used, such as in gap-filling LM-RCA (see Example 3). When using a DNA polymerase to fill gaps, strand displacement by the DNA polymerase is undesirable. Such DNA polymerases are referred to herein as gap-filling DNA polymerases. Unless otherwise indicated, a DNA polymerase referred to herein without specifying it as a rolling circle DNA polymerase or a gap-filling DNA polymerase, is understood to be a rolling circle DNA polymerase and not a gap-filling DNA polymerase. Preferred gap-filling DNA polymerases are T7 DNA polymerase (Studier et al., *Methods Enzymol.* 185:60-89 (1990)), DEEP VENT® DNA polymerase (New England Biolabs, Beverly, Mass.), and T4 DNA polymerase (Kunkel et al., *Methods Enzymol.* 154:367-382 (1987)). An especially preferred type of gap-filling DNA polymerase is the *Thermus flavus* DNA polymerase (MBR, Milwaukee, Wis.). The most preferred gap-filling DNA polymerase is the Stoffel fragment of Taq DNA polymerase (Lawyer et al., *PCR Methods Appl.* 2(4):275-287 (1993), King et al., *J. Biol. Chem.* 269(18):13061-13064 (1994)).

The ability of a polymerase to fill gaps can be determined by performing gap-filling LM-RCA. Gap-filling LM-RCA is performed with an open circle probe that forms a gap space when hybridized to the target sequence. Ligation can only occur when the gap space is filled by the DNA polymerase. If gap-filling occurs, TS-DNA can be detected, otherwise it can be concluded that the DNA polymerase, or the reaction conditions, is not useful as a gap-filling DNA polymerase.

O. RNA Polymerases

Any RNA polymerase which can carry out transcription in vitro and for which promoter sequences have been identified can be used in the disclosed rolling circle transcription method. Stable RNA polymerases without complex requirements are preferred. Most preferred are T7 RNA polymerase (Davanloo et al., *Proc. Natl. Acad. Sci. USA* 81:2035-2039 (1984)) and SP6 RNA polymerase (Butler and Chamberlin, *J. Biol. Chem.* 257:5772-5778 (1982)) which are highly specific for particular promoter sequences (Schenbom and Meirendorf, *Nucleic Acids Research* 13:6223-6236 (1985)). Other RNA polymerases with this characteristic are also preferred. Because promoter sequences are generally recognized by specific RNA polymerases, the OCP or ATC should contain a promoter sequence recognized by the RNA polymerase that is used. Numerous promoter sequences are known and any suitable RNA polymerase having an identified promoter sequence can be used. Promoter sequences for RNA polymerases can be identified using established techniques.

The materials described above can be packaged together in any suitable combination as a kit useful for performing the disclosed method.

II. Method

The disclosed rolling circle amplification (RCA) method involves replication of circular single-stranded DNA molecules. In RCA, a rolling circle replication primer hybridizes to circular OCP or ATC molecules followed by rolling circle replication of the OCP or ATC molecules using a strand-displacing DNA polymerase. Amplification takes place during rolling circle replication in a single reaction cycle. Rolling circle replication results in large DNA molecules containing tandem repeats of the OCP or ATC sequence. This DNA molecule is referred to as a tandem sequence DNA (TS-DNA).

A preferred embodiment, ligation-mediated rolling circle amplification (LM-RCA) method involves a ligation operation prior to replication. In the ligation operation, an OCP hybridizes to its cognate target nucleic acid sequence, if present, followed by ligation of the ends of the hybridized OCP to form a covalently closed, single-stranded OCP. After ligation, a rolling circle replication primer hybridizes to OCP molecules followed by rolling circle replication of the circular OCP molecules using a strand-displacing DNA polymerase. Generally, LM-RCA comprises (a) mixing an open circle probe (OCP) with a target sample, resulting in an OCP-target sample mixture, and incubating the OCP-target sample mixture under conditions promoting hybridization between the open circle probe and a target sequence, (b) mixing ligase with the OCP-target sample mixture, resulting in a ligation mixture, and incubating the ligation mixture under conditions promoting ligation of the open circle probe to form an amplification target circle (ATC), (c) mixing a rolling circle replication primer (RCRP) with the ligation mixture, resulting in a primer-ATC mixture, and incubating the primer-ATC mixture under conditions that promote hybridization between the amplification target circle and the rolling circle replication primer, (d) mixing DNA polymerase with the primer-ATC mixture, resulting in a polymerase-ATC mixture, and incubating the polymerase-ATC mixture under conditions promoting replication of the amplification target circle, where replication of the amplification target circle results in formation of tandem sequence DNA (TS-DNA).

The open circle probe is a single-stranded, linear DNA molecule comprising, from 5' end to 3' end, a 5' phosphate group, a right target probe portion, a primer complement portion, a spacer region, a left target probe portion, and a 3' hydroxyl group, wherein the left target probe portion is complementary to the 5' region of a target sequence and the right target probe portion is complementary to the 3' region of the target sequence.

The left and right target probe portions hybridize to the two ends of the target nucleic acid sequence, with or without a central gap to be filled by one or more gap oligonucleotides. Generally, LM-RCA using gap oligonucleotides can be performed by, in an LM-RCA reaction, (1) using a target sequence with a central region located between a 5' region and a 3' region, and an OCP where neither the left target probe portion of the open circle probe nor the right target probe portion of the open circle probe is complementary to the central region of the target sequence, and (2) mixing one or more gap oligonucleotides with the target sample, such that the OCP-target sample mixture contains the open circle probe, the one or more gap oligonucleotides, and the target sample, where each gap oligonucleotide consists of a single-stranded, linear DNA molecule comprising a 5' phosphate group and a 3' hydroxyl group, where each gap oligonucleotide is complementary all or a portion of the central region of the target sequence.

A. The Ligation Operation

An open circle probe, optionally in the presence of one or more gap oligonucleotides, is incubated with a sample containing DNA, RNA, or both, under suitable hybridization conditions, and then ligated to form a covalently closed circle. The ligated open circle probe is a form of amplification target circle. This operation is similar to ligation of padlock probes described by Nilsson et al., *Science*, 265:2085-2088 (1994). The ligation operation allows subsequent amplification to be dependent on the presence of a target sequence. Suitable ligases for the ligation operation are described above. Ligation conditions are generally known. Most ligases require $Mg^{++}$. There are two main types of ligases, those that are ATP-dependent and those that are NAD-dependent. ATP or NAD, depending on the type of ligase, should be present during ligation.

The ligase and ligation conditions can be optimized to limit the frequency of ligation of single-stranded termini. Such ligation events do not depend on the presence of a target sequence. In the case of AMPLIGASE®-catalyzed ligation, which takes place at 60° C., it is estimated that no more than 1 in 1,000,000 molecules with single-stranded DNA termini will be ligated. This is based on the level of non-specific amplification seen with this ligase in the ligase chain reaction. Any higher nonspecific ligation frequency would cause enormously high background amplification in the ligase chain reaction. Using this estimate, an approximate frequency for the generation of non-specifically ligated open circles with a correctly placed gap oligonucleotide in at the ligation junction can be calculated. Since two ligation events are involved, the frequency of such events using AMPLIGASE® should be the square of 1 in 1,000,000, or 1 in $1 \times 10^{12}$. The number of probes used in a typical ligation reaction of 50 µl is $2 \times 10^{12}$. Thus, the number of non-specifically ligated circles containing a correct gap oligonucleotide would be expected to be about 2 per reaction.

When RNA is to be detected, it is preferred that a reverse transcription operation be performed to make a DNA target sequence. An example of the use of such an operation is described in Example 4. Alternatively, an RNA target sequence can be detected directly by using a ligase that can perform ligation on a DNA:RNA hybrid substrate. A preferred ligase for this is T4 DNA ligase.

B. The Replication Operation

Figure 4:
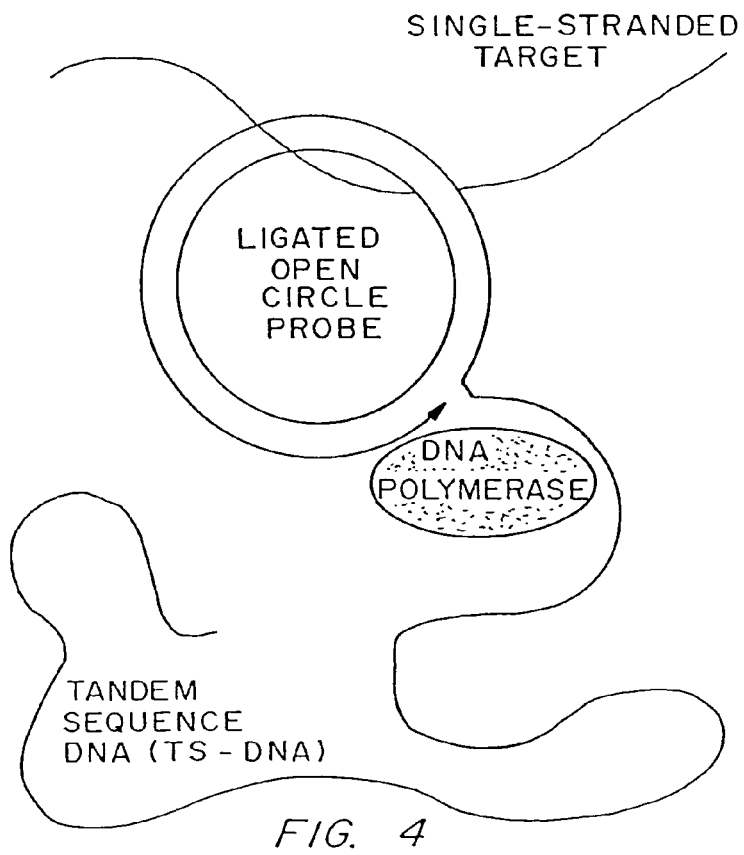
FIG. 4 is a diagram of rolling circle amplification of an open circle probe topologically locked to the nucleic acid containing the target sequence.

The circular open circle probes formed by specific ligation and amplification target circles serve as substrates for a rolling circle replication. This reaction requires the addition of two reagents: (a) a rolling circle replication primer, which is complementary to the primer complement portion of the OCP or ATC, and (b) a rolling circle DNA polymerase. The DNA polymerase catalyzes primer extension and strand displacement in a processive rolling circle polymerization reaction that proceeds as long as desired, generating a molecule of up to 100,000 nucleotides or larger that contains up to approximately 1000 tandem copies of a sequence complementary to the amplification target circle or open circle probe (FIG. 4). This tandem sequence DNA (TS-DNA) consists of, in the case of OCPs, alternating target sequence and spacer sequence. Note that the spacer sequence of the TS-DNA is the complement of the sequence between the left target probe and the right target probe in the original open circle probe. A preferred rolling circle DNA polymerase is the DNA polymerase of the bacteriophage φ29.

During rolling circle replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

C. Modifications and Additional Operations

1. Detection of Amplification Products

Current detection technology makes a second cycle of RCA unnecessary in many cases. Thus, one may proceed to detect the products of the first cycle of RCA directly. Detection may be accomplished by primary labeling or by secondary labeling, as described below.

(a) Primary Labeling

Primary labeling consists of incorporating labeled moieties, such as fluorescent nucleotides, biotinylated nucleotides, digoxygenin-containing nucleotides, or bromodeoxyuridine, during rolling circle replication in RCA, or during transcription in RCT. For example, one may incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

(b) Secondary Labeling with Detection Probes

Figure 7:
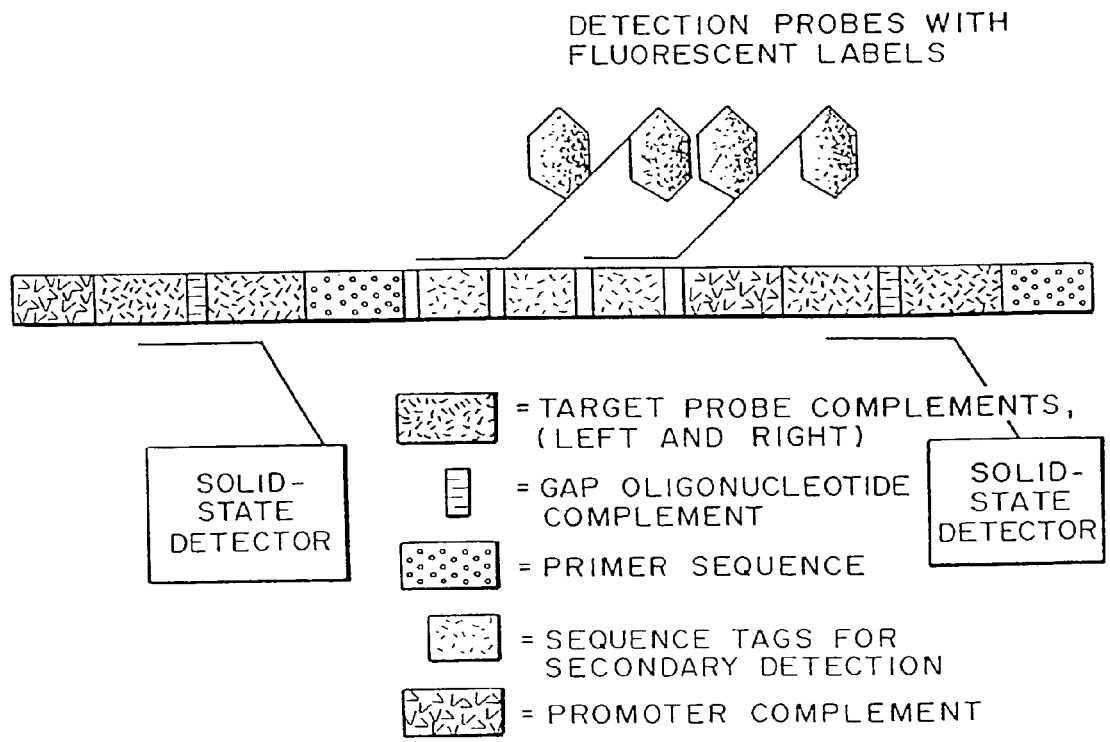
FIG. 7 is a diagram of the capture and detection of TS-DNA. Capture is effected by hybridization of the TS-DNA to address probes attached to a solid-state detector. Detection is effected by hybridization of secondary detection probes to the captured TS-DNA. Portions of the TS-DNA corresponding to various portions of the open circle probe are indicated by different fills.
Figure 9:
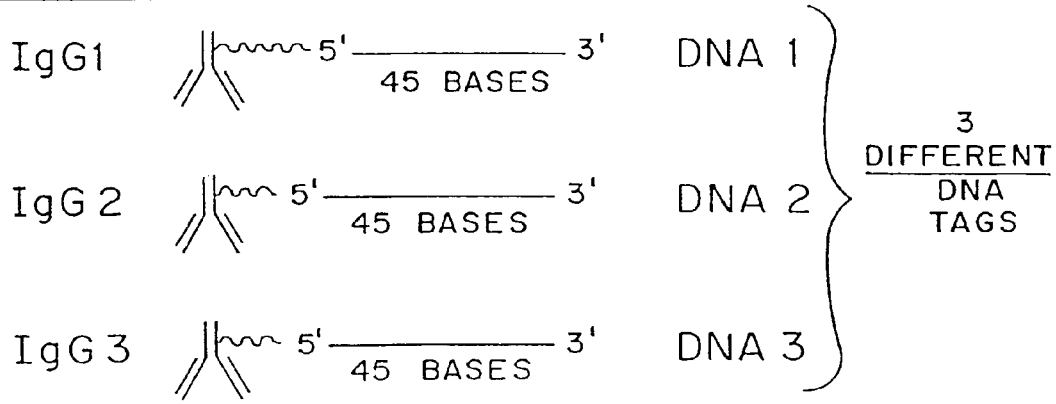
FIG. 9 is a diagram of an example of a multiplex antibody assay employing open circle probes and LM-RCT for generation of an amplified signal. Diagramed are three reporter antibodies, each with a different oligonucleotide as a DNA tag. Diagramed at the bottom is amplification of only that DNA tag coupled to a reporter antibody that bound.
Figure 9:
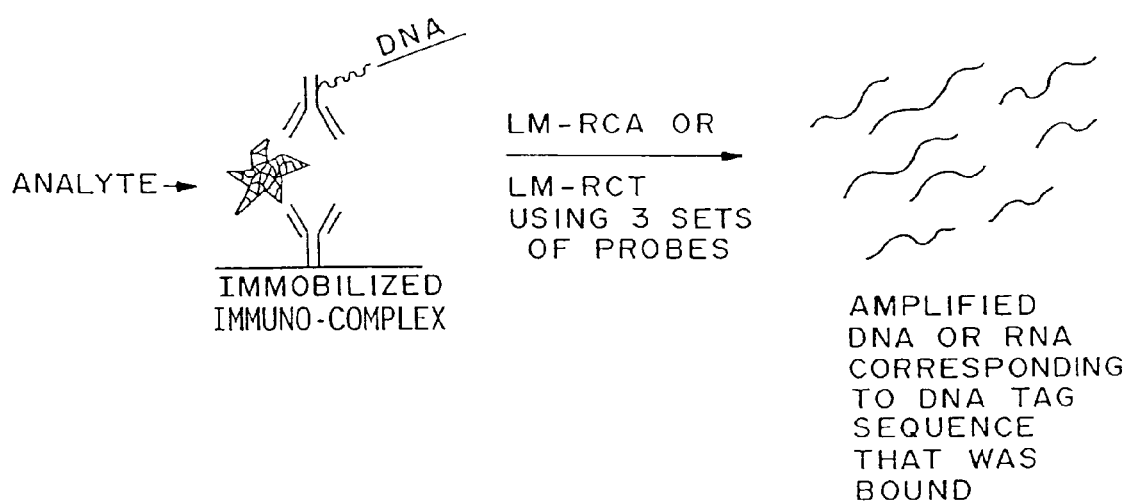
Figure 10:
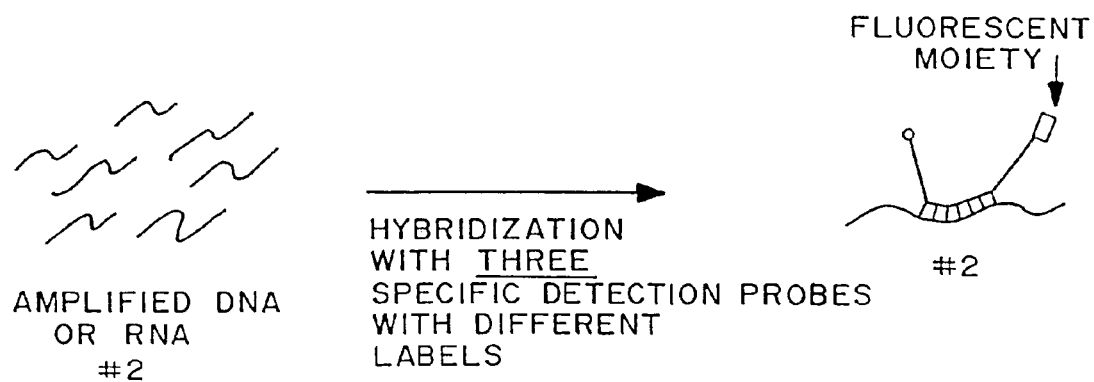
FIG. 10 is a diagram of two schemes for multiplex detection of specific amplified nucleic acids. Diagramed at the top is hybridization of detection probes with different labels to amplified nucleic acids. Diagramed at the bottom is hybridization of amplified nucleic acid to a solid-state detector with address probes for the different possible amplification products attached in a pattern.
Figure 10:
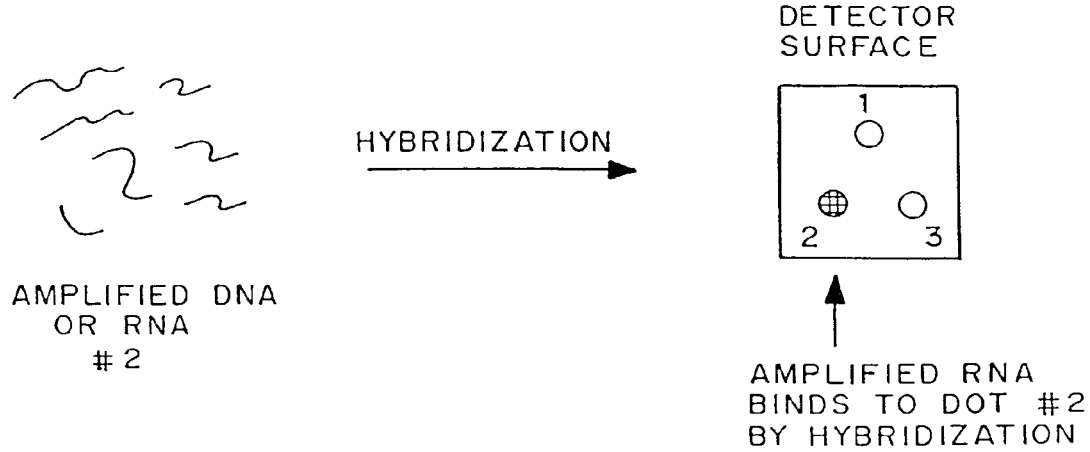

Secondary labeling consists of using suitable molecular probes, referred to as detection probes, to detect the amplified DNA or RNA. For example, an open circle may be designed to contain several repeats of a known arbitrary sequence, referred to as detection tags. A secondary hybridization step can be used to bind detection probes to these detection tags (FIG. 7). The detection probes may be labeled as described above with, for example, an enzyme, fluorescent moieties, or radioactive isotopes. By using three detection tags per open circle probe, and four fluorescent moieties per each detection probe, one may obtain a total of twelve fluorescent signals for every open circle probe repeat in the TS-DNA, yielding a total of 12,000 fluorescent moieties for every ligated open circle probe that is amplified by RCA.

(c) Multiplexing and Hybridization Array Detection

RCA is easily multiplexed by using sets of different open circle probes, each set carrying different target probe sequences designed for binding to unique targets. Note that although the target probe sequences designed for each target are different, the primer complement portion may remain unchanged, and thus the primer for rolling circle replication can remain the same for all targets. Only those open circle probes that are able to find their targets will give rise to TS-DNA. The TS-DNA molecules generated by RCA are of high molecular weight and low complexity; the complexity being the length of the open circle probe. There are two alternatives for capturing a given TS-DNA to a fixed position in a solid-state detector. One is to include within the spacer region of the open circle probes a unique address tag sequence for each unique open circle probe. TS-DNA generated from a given open circle probe will then contain sequences corresponding to a specific address tag sequence. A second and preferred alternative is to use the target sequence present on the TS-DNA as the address tag.

(d) Detecting Groups of Target Sequences

Multiplex RCA assays are particularly useful for detecting mutations in genes where numerous distinct mutations are associated with certain diseases or where mutations in multiple genes are involved. For example, although the gene responsible for Huntington's chorea has been identified, a wide range of mutations in different parts of the gene occur among affected individuals. The result is that no single test has been devised to detect whether an individual has one or more of the many Huntington's mutations. A single LM-RCA assay can be used to detect the presence of one or more members of a group of any number of target sequences. This can be accomplished, for example, by designing an open circle probe (and associated gap oligonucleotides, if desired) for each target sequence in the group, where the target probe portions of each open circle probe are different but the sequence of the primer portions and the sequence of the detection tag portions of all the open circle probes are the same. All of the open circle probes are placed in the same OCP-target sample mixture, and the same primer and detection probe are used to amplify and detect TS-DNA. If any of the target sequences are present in the target sample, the OCP for that target will be ligated into a circle and the circle will be amplified to form TS-DNA. Since the detection tags on TS-DNA resulting from amplification of any of the OCPs are the same, TS-DNA resulting from ligation of any of the OCPs will be detected in that assay. Detection indicates that at least one member of the target sequence group is present in the target sample. This allows detection of a trait associated with multiple target sequences in a single tube or well.

If a positive result is found, the specific target sequence involved can be identified by using a multiplex assay. This can be facilitated by including an additional, different detection tag in each of the OCPs of the group. In this way, TS-DNA generated from each different OCP, representing each different target sequence, can be individually detected. It is convenient that such multiple assays need be performed only when an initial positive result is found.

The above scheme can also be used with arbitrarily chosen groups of target sequences in order to screen for a large number of target sequences without having to perform an equally large number of assays. Initial assays can be performed as described above, each using a different group of OCPs designed to hybridize to a different group of target sequences. Additional assays to determine which target sequence is present can then be performed on only those groups that produce TS-DNA. Such group assays can be further nested if desired.

(e) In Situ Detection Using RCA

In situ hybridization, and its most powerful implementation, known as fluorescent in situ hybridization (FISH), is of fundamental importance in cytogenetics. RCA can be adapted for use in FISH, as follows.

Open circle probes are ligated on targets on microscope slides, and incubated in situ with fluorescent precursors during rolling circle replication. The rolling circle DNA polymerase displaces the ligated open circle probe from the position where it was originally hybridized. However, the circle will remain topologically trapped on the chromosome unless the DNA is nicked (Nilsson et al. (1994)). The presence of residual chromatin may slow diffusion of the circle along the chromosome. Alternatively, fixation methods may be modified to minimize this diffusional effect. This diffusion has an equal probability of occurring in either of two directions along the chromosome, and hence net diffusional displacement may be relatively small during a 10 minute incubation. During this time rolling circle replication should generate a linear molecule of approximately 25,000 nucleotides containing approximately 2,500 bromodeoxyuridine moieties, which can be detected with a biotinylated anti-BUDR IgG (Zymed Labs, Inc.) and fluorescein-labeled avidin. This level of incorporation should facilitate recording of the image using a microscope-based CCD system. Diffusion may also be limited because the TS-DNA should be able to hybridize with the complement of the target strand.

Multiplexed in situ detection can be carried out as follows: Rolling circle replication is carried out using unlabeled nucleotides. The different TS-DNAs are then detected using standard multi-color FISH with detection probes specific for each unique target sequence or each unique detection tag in the TS-DNA.

(f) Enzyme-linked Detection

Amplified nucleic acid labeled by incorporation of labeled nucleotides can be detected with established enzyme-linked detection systems. For example, amplified nucleic acid labeled by incorporation of biotin-16-UTP (Boehringher Mannheim) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

2. Nested LM-RCA

After RCA, a round of LM-RCA can be performed on the TS-DNA produced in the first RCA. This new round of LM-RCA is performed with a new open circle probe, referred to as a secondary open circle probe, having target probe portions complementary to a target sequence in the TS-DNA produced in the first round. When such new rounds of LM-RCA are performed, the amplification is referred to herein as nested LM-RCA. Nested LM-RCA is particularly useful for in situ hybridization applications of LM-RCA. Preferably, the target probe portions of the secondary OCP are complementary to a secondary target sequence in the spacer sequences of the TS-DNA produced in the first RCA. The complement of this secondary target sequence is present in the spacer portion of the OCP or ATC used in the first RCA. After mixing the secondary OCP with the TS-DNA, ligation and rolling circle amplification proceed as in LM-RCA. Each ligated secondary OCP generates a new TS-DNA. By having, for example, two secondary target sequence portions in the first round OCP, the new round of LM-RCA will yield two secondary TS-DNA molecules for every OCP or ATC repeat in the TS-DNA produced in the first RCA. Thus, the amplification yield of nested LM-RCA is about 2000-fold. The overall amplification using two cycles of RCA is thus 1000×2000=2,000,000. Nested LM-RCA can follow any DNA replication or transcription operation described herein, such as RCA, LM-RCA, secondary DNA strand displacement, strand displacement cascade amplification, or transcription.

Generally, nested LM-RCA involves, following a first RCA, (a) mixing a secondary open circle probe with the polymerase mixture, resulting in an OCP-TS mixture, and incubating the OCP-TS mixture under conditions promoting hybridization between the secondary open circle probe and the tandem sequence DNA, (b) mixing ligase with the OCP-TS mixture, resulting in a secondary ligation mixture, and incubating the secondary ligation mixture under conditions promoting ligation of the secondary open circle probe to form a secondary amplification target circle, (c) mixing a rolling circle replication primer with the secondary ligation mixture, resulting in a secondary primer-ATC mixture, and incubating the secondary primer-ATC mixture under conditions that promote hybridization between the secondary amplification target circle and rolling circle replication primer, (d) mixing DNA polymerase with the secondary primer-ATC mixture, resulting in a secondary polymerase-ATC mixture, and incubating the secondary polymerase-ATC mixture under conditions promoting replication of the secondary amplification target circle, where replication of the secondary amplification target circle results in formation of nested tandem sequence DNA.

An exonuclease digestion step can be added prior to performing the nested LM-RCA. This is especially useful when the target probe portions of the secondary open circle probe are the same as those in the first open circle probe. Any OCP which has been ligated will not be digested since ligated OCPs have no free end. A preferred way to digest OCPs that have hybridized to TS-DNA during the first round of LM-RCA is to use a special rolling circle replication primer containing at least about four phosphorothioate linkages between the nucleotides at the 5' end. Then, following rolling circle replication, the reaction mixture is subjected to exonuclease digestion. By using a 5' exonuclease unable to cleave these phosphorothioate linkages, only the OCPs hybridized to TS-DNA will be digested, not the TS-DNA. The TS-DNA generated during the first cycle of amplification will not be digested by the exonuclease because it is protected by the phosphorothioate linkages at the 5' end. A preferred exonuclease for this purpose is the T7 gene 6 exonuclease. The T7 gene 6 exonuclease can be inactivated prior to adding the secondary open circle probe by heating to 90° C. for 10 minutes.

By using an exonuclease digestion, nested LM-RCA can be performed using the same target sequence used in a first round of LM-RCA. This can be done, for example, generally as follows. After the first round of LM-RCA, the unligated open circle probes and gap oligonucleotides hybridized to TS-DNA are digested with T7 gene 6 exonuclease. The exonuclease is inactivated by heating for 10 minutes at 90° C. Then a second open circle probe is added. In this scheme, the second open circle probe has target probe portions complementary to the same original target sequence, but which contain a different (arbitrary) spacer region sequence. A second round of LM-RCA is then performed. In this second round, the target of the second open circle probes comprises the repeated target sequences contained in the TS-DNA generated by the first cycle. This procedure has the advantage of preserving the original target sequence in the amplified DNA obtained after nested LM-RCA.

Figure 12:
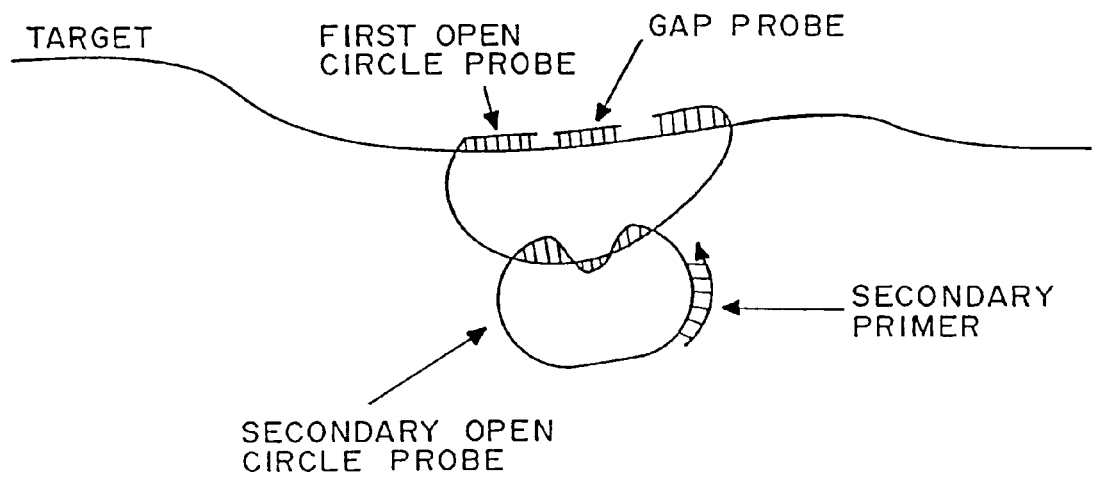
FIG. 12 is a diagram of an example of nested RCA using an unamplified first open circle probe as the target sequence. Diagramed at the top is a gap oligonucleotide and a first open circle probe hybridized to a target sequence, and a secondary open circle probe hybridized to the first open circle probe. Diagramed at the bottom is the rolling circle replication product of the secondary open circle probe.
Figure 12:
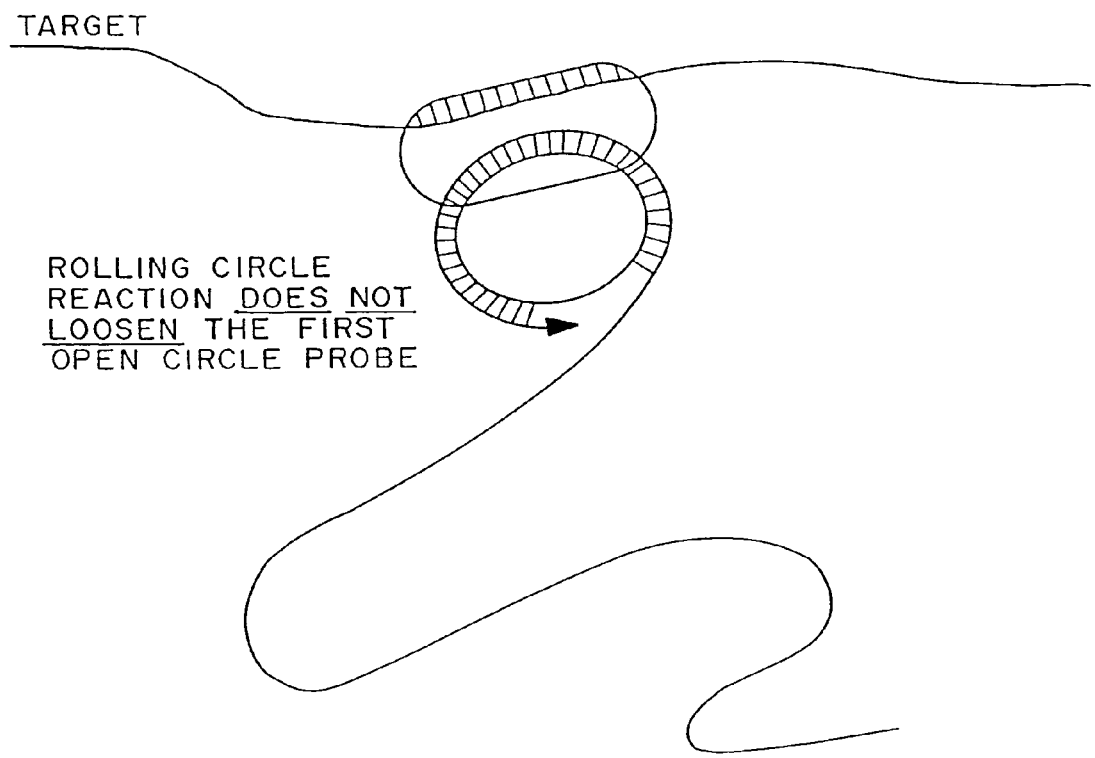

Nested LM-RCA can also be performed on ligated OCPs or ATCs that have not been amplified. In this case, LM-RCA can be carried out using either ATCs or target-dependent ligated OCPs. This is especially useful for in situ detection. For in situ detection, the first, unamplified OCP, which is topologically locked to its target sequence, can be subjected to nested LM-RCA. By not amplifying the first OCP, it can remain hybridized to the target sequence while LM-RCA amplifies a secondary OCP topologically locked to the first OCP. This is illustrated in FIG. 12.

Figure 11A:
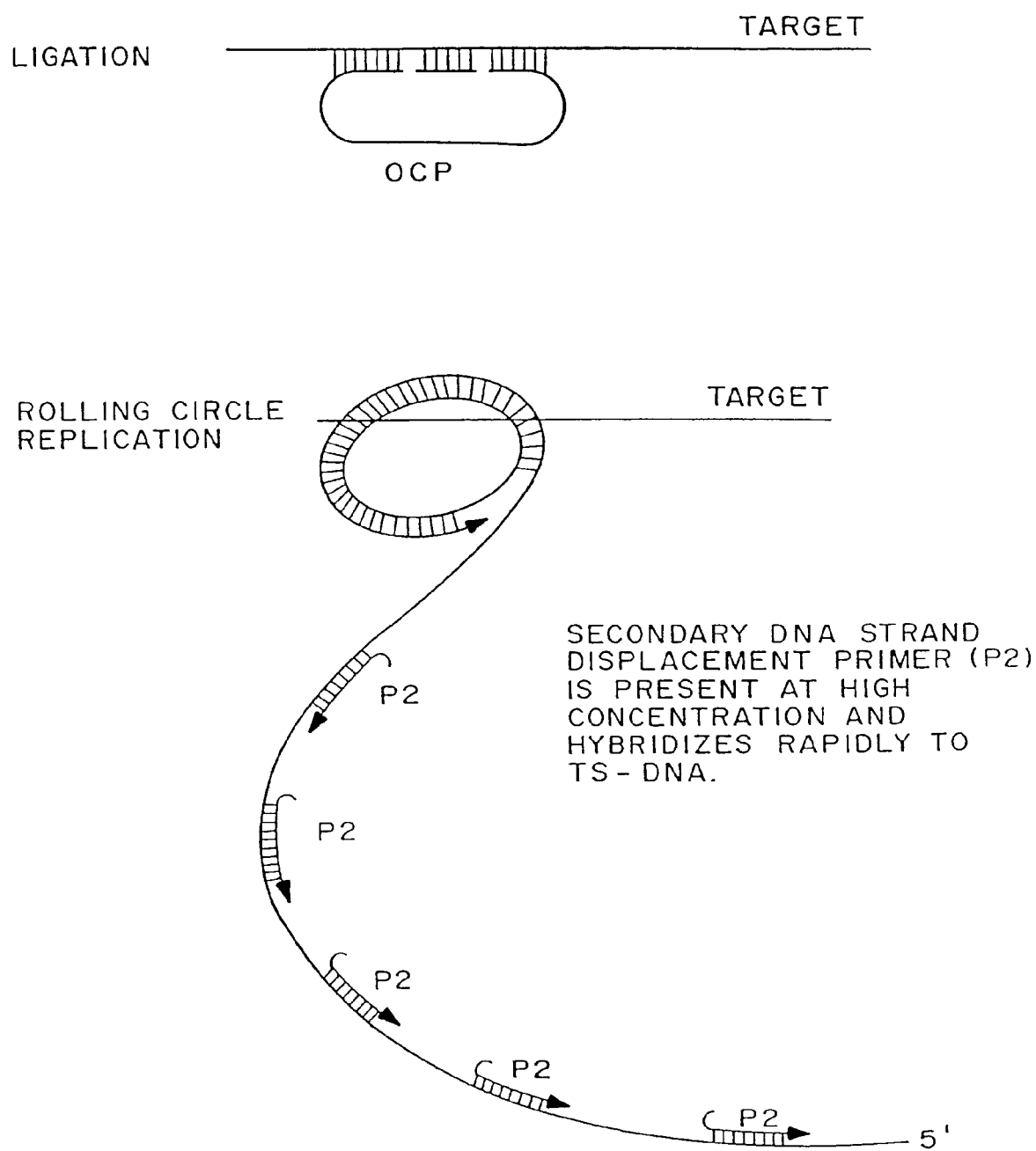
FIGS. 11A and 11B are diagrams of an example of secondary DNA strand displacement. Diagramed at the top of FIG. 11A is a gap oligonucleotide and an open circle probe hybridized to a target sequence. Diagramed at the bottom of FIG. 11A is the rolling circle replication product hybridized to secondary DNA strand displacement primers. Diagramed in FIG. 11B is secondary DNA strand displacement initiated from multiple primers.

3. Secondary DNA Strand Displacement and Strand Displacement Cascade Amplification Secondary DNA strand displacement is another way to amplify TS-DNA. Secondary DNA strand displacement is accomplished by hybridizing secondary DNA strand displacement primers to TS-DNA and allowing a DNA polymerase to synthesize DNA from these primed sites (FIG. 11). Since a complement of the secondary DNA strand displacement primer occurs in each repeat of the TS-DNA, secondary DNA strand displacement can result in a level of amplification similar to or larger than that obtained in RCT. The product of secondary DNA strand displacement is referred to as secondary tandem sequence DNA or TS-DNA-2.

Secondary DNA strand displacement can be accomplished by performing RCA to produce TS-DNA in a polymerase-ATC mixture, and then mixing secondary DNA strand displacement primer with the polymerase-ATC mixture, resulting in a secondary DNA strand displacement mixture, and incubating the secondary DNA strand displacement mixture under conditions promoting replication of the tandem sequence DNA. The secondary DNA strand displacement primer is complementary to a part of the OCP or ATC used to generated TS-DNA as described earlier. It is preferred that the secondary DNA strand displacement primer is not complementary to the rolling circle replication primer, or to a tertiary DNA strand displacement primer, if used.

Figure 11B:
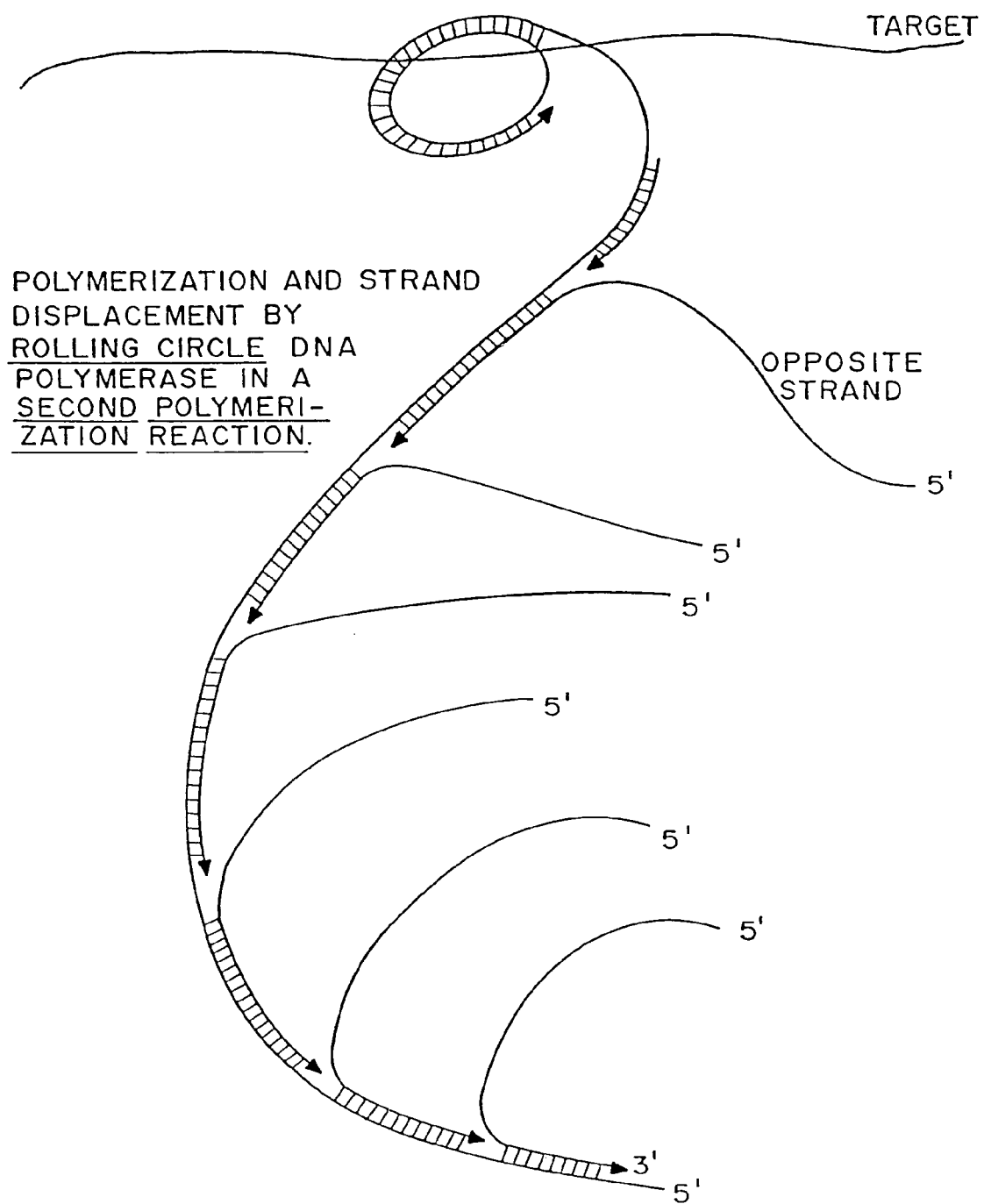

Secondary DNA strand displacement can also be carried out simultaneously with rolling circle replication. This is accomplished by mixing secondary DNA strand displacement primer with the polymerase-ATC mixture prior to incubating the mixture for rolling circle replication. For simultaneous rolling circle replication and secondary DNA strand displacement, it is preferred that the rolling circle DNA polymerase be used for both replications. This allows optimum conditions to be used and results in displacement of other strands being synthesized downstream as shown in FIG. 11B. Secondary DNA strand displacement can follow any DNA replication operation disclosed herein, such as RCA, LM-RCA or nested LM-RCA.

To optimize the efficiency of secondary DNA strand displacement, it is preferred that a sufficient concentration of secondary DNA strand displacement primer be used to obtain sufficiently rapid priming of the growing TS-DNA strand to outcompete any remaining unligated OCPs and gap oligonucleotides that might be present for binding to TS-DNA. In general, this is accomplished when the secondary DNA strand displacement primer is in very large excess compared to the concentration of single-stranded sites for hybridization of the secondary DNA strand displacement primer on TS-DNA. Optimization of the concentration of secondary DNA strand displacement primer can be aided by analysis of hybridization kinetics using methods such as those described by Young and Anderson, "Quantitative analysis of solution hybridization" in *Nucleic Acid Hybridization: A Practical Approach* (IRL Press, 1985) pages 47-71. For example, assuming that $\phi$29 DNA polymerase is used as the rolling circle DNA polymerase, TS-DNA is generated at a rate of about 53 nucleotides per second, and the rolling circle DNA polymerase generates approximately 10 copies of the amplification target circle. Analysis of the theoretical solution hybridization kinetics for an OCP driver DNA (unligated OCP) present at a concentration of 80 nM (a typical concentration used for a LM-RCA ligation operation), and the theoretical solution hybridization kinetics for a secondary DNA strand displacement primer driver DNA present at a concentration of 800 nM, indicates that the secondary DNA strand displacement primer will bind to those 10 copies within 30 seconds, while unligated OCP will hybridize to less than one site in 30 seconds (8% of sites filled). If the concentration of DNA polymerase is relatively high (for this example, in the range of 100 to 1000 nM), the polymerase will initiate DNA synthesis at each available 3' terminus on the hybridized secondary DNA strand displacement primers, and these elongating TS-DNA-2 molecules will block any hybridization by the unligated OCP molecules. Alternatively, the efficiency of secondary DNA strand displacement can be improved by the removal of unligated open circle probes and gap oligonucleotides prior to amplification of the TS-DNA. In secondary DNA strand displacement, it is preferred that the concentration of secondary DNA strand displacement primer generally be from 500 nM to 5000 nM, and most preferably from 700 nM to 1000 nM.

As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. The generation of TS-DNA-2 and its release into solution by strand displacement is shown diagrammatically in FIG. 11.

Generally, secondary DNA strand displacement can be performed by, simultaneous with or following RCA, mixing a secondary DNA strand displacement primer with the polymerase-ATC mixture, and incubating the polymerase-ATC mixture under conditions that promote both hybridization between the tandem sequence DNA and the secondary DNA strand displacement primer, and replication of the tandem sequence DNA, where replication of the tandem sequence DNA results in the formation of secondary tandem sequence DNA.

Figure 13:
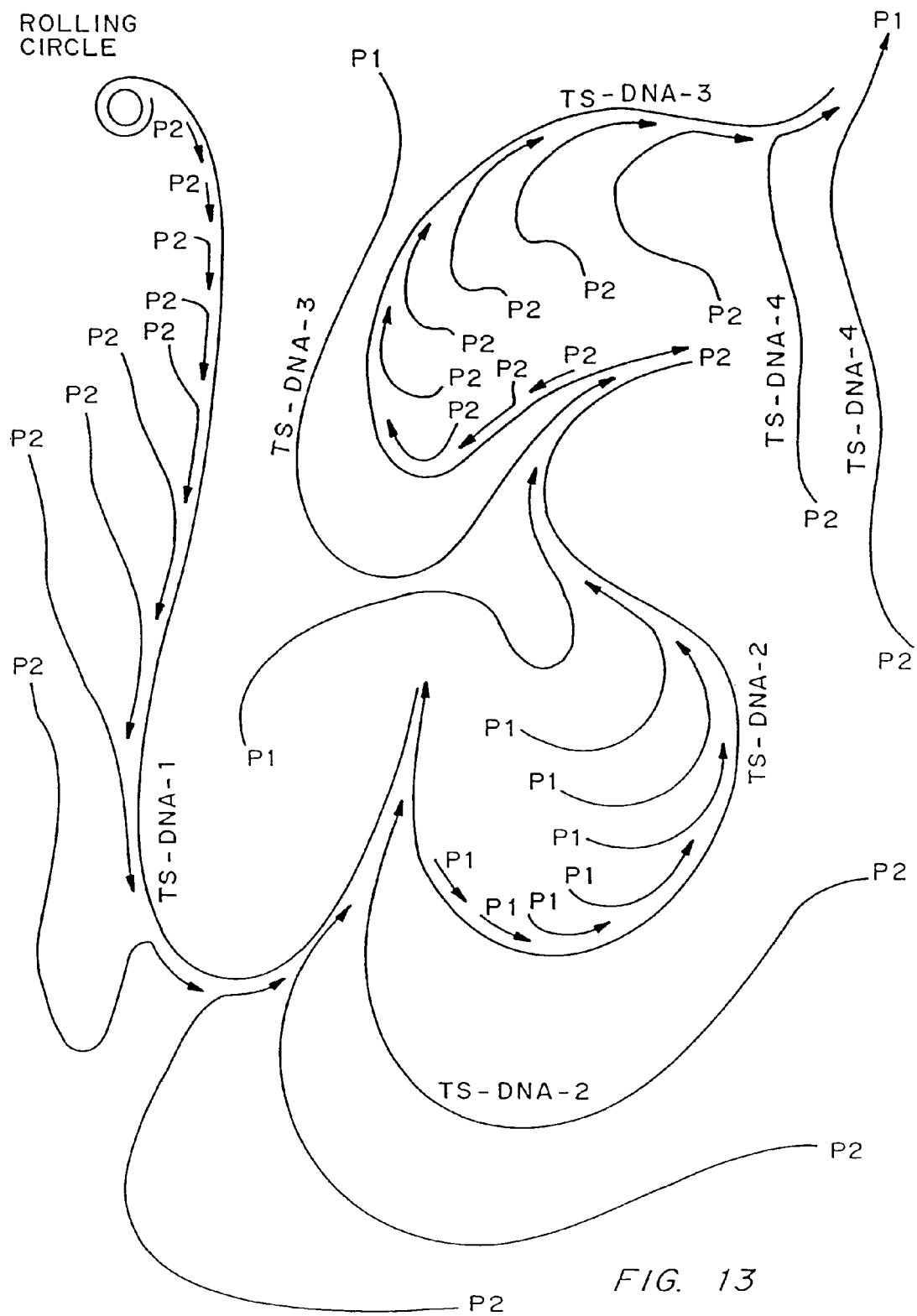
FIG. 13 is a diagram of an example of strand displacement cascade amplification. Diagramed is the synthesis and template relationships of four generations of TS-DNA. TS-DNA-1 is generated by rolling circle replication primed by the rolling circle replication primer. TS-DNA-2 and TS-DNA-4 are generated by secondary DNA strand displacement primed by a secondary DNA strand displacement primer (P2). TS-DNA-3 is generated by strand-displacing secondary DNA strand displacement primed by a tertiary DNA strand displacement primer (P1).
Figure 14:
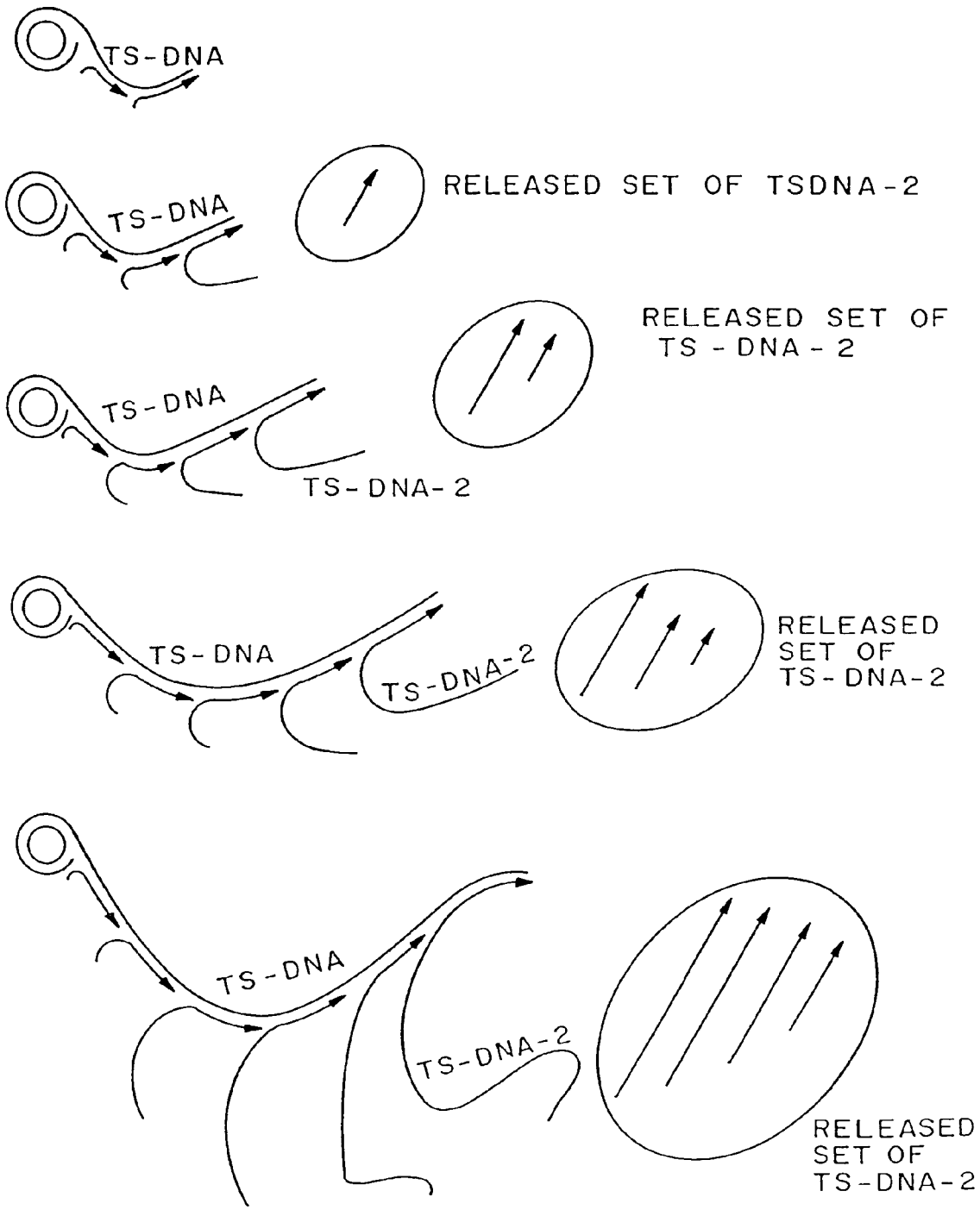
FIG. 14 is a diagram of an example of opposite strand amplification. Diagramed are five different stages of the reaction as DNA synthesis proceeds. TS-DNA-2 is generated by secondary DNA strand displacement of TS-DNA primed by the secondary DNA strand displacement primer. As rolling circle replication creates new TS-DNA sequence, the secondary DNA strand displacement primer hybridizes to the newly synthesized DNA and primes synthesis of another copy of TS-DNA-2.

When secondary DNA strand displacement is carried out in the presence of a tertiary DNA strand displacement primer, an exponential amplification of TS-DNA sequences takes place. This special and preferred mode of secondary DNA strand displacement is referred to as strand displacement cascade amplification (SDCA). In SDCA, illustrated in FIG. 13, a secondary DNA strand displacement primer primes replication of TS-DNA to form TS-DNA-2, as described above. The tertiary DNA strand displacement primer strand can then hybridize to, and prime replication of, TS-DNA-2 to form TS-DNA-3. Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. This reaction amplifies DNA at an almost exponential rate, although kinetics are not truly exponential because there are stochastically distributed priming failures, as well as steric hindrance events related to the large size of the DNA network produced during the reaction. In a preferred mode of SDCA, the rolling circle replication primer serves as the tertiary DNA strand displacement primer, thus eliminating the need for a separate primer. For this mode, the rolling circle replication primer should be used at a concentration sufficiently high to obtain rapid priming on the growing TS-DNA-2 strands. To optimize the efficiency of SDCA, it is preferred that a sufficient concentration of secondary DNA strand displacement primer and tertiary DNA strand displacement primer be used to obtain sufficiently rapid priming of the growing TS-DNA strand to outcompete TS-DNA for binding to its complementary TS-DNA, and, in the case of secondary DNA strand displacement primer, to outcompete any remaining unligated OCPs and gap oligonucleotides that might be present for binding to TS-DNA. In general, this is accomplished when the secondary DNA strand displacement primer and tertiary DNA strand displacement primer are both in very large excess compared to the concentration of single-stranded sites for hybridization of the DNA strand displacement primers on TS-DNA. For example, it is preferred that the secondary DNA strand displacement primer is in excess compared to the concentration of single-stranded secondary DNA strand displacement primer complement sites on TS-DNA, TS-DNA-3, TS-DNA-5, and so on. In the case of tertiary DNA strand displacement primer, it is preferred that the tertiary DNA strand displacement primer is in excess compared to the concentration of single-stranded tertiary DNA strand displacement primer complement sites on TS-DNA-2, TS-DNA-4, TS-DNA-6, and so on. Such an excess generally results in a primer hybridizing to its complement in TS-DNA before amplified complementary TS-DNA can hybridize. Optimization of primer concentrations can be aided by analysis of hybridization kinetics (Young and Anderson). In a strand displacement cascade amplification, it is preferred that the concentration of both secondary and tertiary DNA strand displacement primers generally be from 500 nM to 5000 nM, and most preferably from 700 nM to 1000 nM.

As in the case of secondary DNA strand displacement primers, if the concentration of DNA polymerase is sufficiently high, the polymerase will initiate DNA synthesis at each available 3' terminus on the hybridized tertiary DNA strand displacement primers, and these elongating TS-DNA-3 molecules will block any hybridization by TS-DNA-2. As a tertiary DNA strand displacement primer is elongated to form TS-DNA-3, the DNA polymerase will run into the 5' end of the next hybridized tertiary DNA strand displacement primer molecule and will displace its 5' end. In this fashion a tandem queue of elongating DNA polymerases is formed on the TS-DNA-2 template. As long as the reaction continues, new rolling circle replication primers and new DNA polymerases are added to TS-DNA-2 at the growing ends of TS-DNA-2. This hybridization/replication/strand displacement cycle is repeated with hybridization of secondary DNA strand displacement primers on the growing TS-DNA-3. The cascade of TS-DNA generation, and their release into solution by strand displacement is shown diagrammatically in FIG. 13.

Generally, strand displacement cascade amplification can be performed by, simultaneous with, or following, RCA, mixing a secondary DNA strand displacement primer and a tertiary DNA strand displacement primer with the polymerase-ATC mixture, and incubating the polymerase-ATC mixture under conditions that promote both hybridization between the tandem sequence DNA and the DNA strand displacement primers, and replication of the tandem sequence DNA, where replication of the tandem sequence DNA results in the formation of secondary tandem sequence DNA.

An example of the amplification yield generated by a strand displacement cascade amplification can be roughly estimated as follows. A rolling circle reaction that proceeds for 35 minutes at 53 nucleotides per second will generate 1236 copies of a 90 nucleotide amplification target circle. Thus, TS-DNA-1 contains 1236 tandem repeats. As these 1236 tandem repeats grow, priming and synthesis with secondary DNA strand displacement primers can generate at least 800 TS-DNA-2 molecules, taking into account delays and missed priming events. These new molecules will have lengths linearly distributed in the range of 1 to 799 repeats. Next, priming events on TS-DNA-2 by tertiary DNA strand displacement primers can generate at least 500 TS-DNA-3 molecules, taking into account delays and missed priming events, and these new molecules will have lengths linearly distributed in the range of 1 to 499 repeats. Then, priming events on TS-DNA-3 by secondary DNA strand displacement primers can generate at least 300 TS-DNA-4 molecules, taking into account delays and missed priming events, and these new molecules will have lengths linearly distributed in the range of 1 to 299 repeats. A conservative overall amplification yield, calculated as the product of only these four amplification levels, is estimated to be $1.86 \times 10^{10}$ repeats of the original OCP or ATC. Thus, SDCA is capable of extremely high amplification yields in an isothermal 35-minute reaction.

A modified form of secondary DNA strand displacement results in amplification of TS-DNA and is referred to as opposite strand amplification (OSA). OSA is the same as secondary DNA strand displacement except that a special form of rolling circle replication primer is used that prevents it from hybridizing to TS-DNA-2. This can be accomplished in a number of ways. For example, the rolling circle replication primer can have an affinity tag coupled to its non-complementary portion allowing the rolling circle replication primer to be removed prior to secondary DNA strand displacement. Alternatively, remaining rolling circle replication primer can be crippled following initiation of rolling circle replication. One preferred form of rolling circle replication primer for use in OSA is designed to form a hairpin that contains a stem of perfectly base-paired nucleotides. The stem can contain 5 to 12 base pairs, most preferably 6 to 9 base pairs. Such a hairpin-forming rolling circle replication primer is a poor primer at lower temperature (less than 40° C.) because the hairpin structure prevents it from hybridizing to complementary sequences. The stem should involve a sufficient number of nucleotides in the complementary portion of the rolling circle replication primer to interfere with hybridization of the primer to the OCP or ATC. Generally, it is preferred that a stem involve 5 to 24 nucleotides, and most preferably 6 to 18 nucleotides, of the complementary portion of a rolling circle replication primer. A rolling circle replication primer where half of the stem involves nucleotides in the complementary portion of the rolling circle replication primer and the other half of the stem involves nucleotides in the non-complementary portion of the rolling circle replication primer is most preferred. Such an arrangement eliminates the need for self-complementary regions in the OCP or ATC when using a hairpin-forming rolling circle replication primer.

When starting the rolling circle replication reaction, secondary DNA strand displacement primer and rolling circle replication primer are added to the reaction mixture, and the solution is incubated briefly at a temperature sufficient to disrupt the hairpin structure of the rolling circle replication primer but to still allow hybridization to the primer complement portion of the amplification target circle (typically greater than 50° C.). This incubation permits the rolling circle replication primer to hybridize to the primer complement portion of the amplification target circle. The solution is then brought to the proper temperature for rolling circle replication, and the rolling circle DNA polymerase is added. As the rolling circle reaction proceeds, TS-DNA is generated, and as the TS-DNA grows in length, the secondary DNA strand displacement primer rapidly initiates DNA synthesis with multiple strand displacement reactions on TS-DNA. These reactions generate TS-DNA-2, which is complementary to the TS-DNA. While TS-DNA-2 contains sequences complementary to the rolling circle replication primer, the primer is not able to hybridize nor prime efficiently at the reaction temperature due to its hairpin structure at this temperature. Thus, there is no further priming by the rolling circle replication primer and the only products generated are TS-DNA and TS-DNA-2. The reaction comes to a halt as rolling circle amplification stops and TS-DNA becomes completely double-stranded. In the course of the reaction, an excess of single-stranded TS-DNA-2 is generated.

Another form of rolling circle replication primer useful in OSA is a chimera of DNA and RNA. In this embodiment, the rolling circle primer has deoxyribonucleotides at its 3' end and ribonucleotides in the remainder of the primer. It is preferred that the rolling circle replication primer have five or six deoxyribonucleotides at its 3' end. By making part of the rolling circle replication primer with ribonucleotide, the primer can be selectively degraded by RNAse H when it is hybridized to DNA. Such hybrids form during OSA as TS-DNA-2 is synthesized. The deoxyribonucleotides at the 3' end allow the rolling circle DNA polymerase to initiate rolling circle replication. RNAse H can then be added to the OSA reaction to prevent priming of TS-DNA-2 replication.

An example of the amplification yield generated by OSA can be roughly estimated as follows. A rolling circle reaction that proceeds for 45 minutes at 53 nucleotides per second will generate tandem 1590 copies of a 90 nucleotide amplification target circle. Thus, TS-DNA-1 contains 1590 tandem repeats. As these 1590 tandem repeats grow, priming and displacement reactions with secondary DNA strand displacement primers will generate and release up to 1400 TS-DNA-2 molecules, and those new molecules will have lengths linearly distributed in the range of 1 to 1399 repeats. Calculations indicate that after 45 minutes, single-stranded TS-DNA-2 exceeds the amount of TS-DNA by a factor of about 700. OSA is useful for generating single-stranded DNA that contains the reverse complement of the target sequence. Overall amplification can be of the order of one million fold.

If secondary DNA strand displacement is used with a ligated OCP, unligated OCPs and gap oligonucleotides may be removed prior to rolling circle replication to eliminate competition between unligated OCPs and gap oligonucleotides and the secondary DNA strand displacement primer for hybridization to TS-DNA. An exception would be when secondary DNA strand displacement is used in conjunction with gap-filling LM-RCA, as described below. Alternatively, the concentration of the secondary DNA strand displacement primer can be made sufficiently high so that it outcompetes unligated OCP for hybridization to TS-DNA. This allows secondary DNA strand displacement to be performed without removal of unligated OCPs.

The DNA generated by secondary DNA strand displacement can be labeled and/or detected using the same labels, labeling methods, and detection methods described for use with TS-DNA. Most of these labels and methods are adaptable for use with nucleic acids in general. A preferred method of labeling the DNA is by incorporation of labeled nucleotides during synthesis.

4. Multiple Ligation Cycles

Using a thermostable DNA ligase, such as AMPLIGASE® (Epicentre Technologies, Inc.), the open circle probe ligation reaction may be cycled a number of times between a annealing temperature (55° C.) and a melting temperature (96° C.). This cycling will produce multiple ligations for every target sequence present in the sample. For example, 8 cycles of ligation would provide and approximate 6-fold increase in the number of ligated circles. A preferred cycling protocol is 96° C. for 2 seconds, 55° C. for 2 seconds, and 60° C. for 70 seconds in a Perkin Elmer 9600 thermal cycler. If the number of cycles is kept small, the linearity of the amplification response should not be compromised.

The expected net amplification yield using eight ligation cycles, secondary fluorescent tags, and array hybridization can be calculated as shown below.

| | |
|---|---|
| Ligation cycling yield: | 6 |
| OSA yield | 1,000,000 |
| number of fluorescent tags/circle | 5 |
| 20% array hybridization yield | 0.2 |

Net yield=6×1,000,000×5×0.2=6,000,000 target molecules×6,000,000=6×10$^8$ fluors bound on the surface

5. Transcription Following RCA (RCT)

Once TS-DNA is generated using RCA, further amplification can be accomplished by transcribing the TS-DNA from promoters embedded in the TS-DNA. This combined process, referred to as rolling circle replication with transcription (RCT), or ligation mediated rolling circle replication with transcription (LM-RCT), requires that the OCP or ATC from which the TS-DNA is made have a promoter portion in its spacer region. The promoter portion is then amplified along with the rest of the OCP or ATC resulting in a promoter embedded in each tandem repeat of the TS-DNA (FIG. 8). Since transcription, like rolling circle amplification, is a process that can go on continuously (with re-initiation), multiple transcripts can be produced from each of the multiple promoters present in the TS-DNA. RCT effectively adds another level of amplification of ligated OCP sequences.

Generally, RCT can be accomplished by performing RCA to produce TS-DNA in a polymerase-OCP mixture or polymerase-ATC mixture, and then mixing RNA polymerase with the polymerase-OCP mixture or polymerase-ATC mixture, resulting in a transcription mixture, and incubating the transcription mixture under conditions promoting transcription of the tandem sequence DNA. The OCP or ATC must include the sequence of a promoter for the RNA polymerase (a promoter portion) in its spacer region for RCT to work. The transcription step in RCT generally can be performed using established conditions for in vitro transcription of the particular RNA polymerase used. Preferred conditions are described in the Examples. Alternatively, transcription can be carried out simultaneously with rolling circle replication. This is accomplished by mixing RNA polymerase with the polymerase-OCP mixture or polymerase-ATC mixture prior to incubating the mixture for rolling circle replication. For simultaneous rolling circle replication and transcription the rolling circle DNA polymerase and RNA polymerase must be active in the same conditions. Such conditions can be optimized in order to balance and/or maximize the activity of both polymerases. It is not necessary that the polymerase achieve their maximum activity, a balance between the activities is preferred. Transcription can follow any DNA replication operation described herein, such as RCA, LM-RCA, nested LM-RCA, secondary DNA strand displacement, or strand displacement cascade amplification.

The transcripts generated in RCT can be labeled and/or detected using the same labels, labeling methods, and detection methods described for use with TS-DNA. Most of these labels and methods are adaptable for use with nucleic acids in general. A preferred method of labeling RCT transcripts is by direct labeling of the transcripts by incorporation of labeled nucleotides, most preferably biotinylated nucleotides, during transcription.

6. Gap-Filling Ligation

The gap space formed by an OCP hybridized to a target sequence is normally occupied by one or more gap oligonucleotides as described above. Such a gap space may also be filled in by a gap-filling DNA polymerase during the ligation operation. This modified ligation operation is referred to herein as gap-filling ligation and is the preferred form of the ligation operation. The principles and procedure for gap-filling ligation are generally analogous to the filling and ligation performed in gap LCR (Wiedmann et al., *PCR Methods and Applications* (Cold Spring Harbor Laboratory Press, Cold Spring Harbor Laboratory, NY, 1994) pages S51-S64; Abravaya et al., *Nucleic Acids Res.*, 23(4):675-682 (1995); European Patent Application EP0439182 (1991)). In the case of LM-RCA, the gap-filling ligation operation is substituted for the normal ligation operation. Gap-filling ligation provides a means for discriminating between closely related target sequences. An example of this is described in Example 3. Gap-filling ligation can be accomplished by using a different DNA polymerase, referred to herein as a gap-filling DNA polymerase. Suitable gap-filling DNA polymerases are described above. Alternatively, DNA polymerases in general can be used to fill the gap when a stop base is used. The use of stop bases in the gap-filling operation of LCR is described in European Patent Application EP0439182. The principles of the design of gaps and the ends of flanking probes to be joined, as described in EP0439182, is generally applicable to the design of the gap spaces and the ends of target probe portions described herein.

To prevent interference of the gap-filling DNA polymerase with rolling circle replication, the gap-filling DNA polymerase can be removed by extraction or inactivated with a neutralizing antibody prior to performing rolling circle replication. Such inactivation is analogous to the use of antibodies for blocking Taq DNA polymerase prior to PCR (Kellogg et al., *Biotechniques* 16(6):1134-1137 (1994)).

Gap-filling ligation is also preferred because it is highly compatible with exponential amplification of OCP sequences similar to the strand displacement cascade amplification (SDCA) as described above. As TS-DNA is formed during rolling circle replication, unligated OCP molecules present in the reaction hybridize to TS-DNA, leaving gap spaces between every OCP repeat. The hybridized OCP molecules serve as primers for secondary DNA synthesis.

Generally, gap-filling LM-RCA can be performed by, in an LM-RCA reaction, (1) using a target sequence with a central region located between a 5' region and a 3' region, and an OCP where neither the left target probe portion of the open circle probe nor the right target probe portion of the open circle probe is complementary to the central region of the target sequence, and (2) mixing gap-filling DNA polymerase with the OCP-target sample mixture.

D. Discrimination Between Closely Related Target Sequences

Open circle probes, gap oligonucleotides, and gap spaces can be designed to discriminate closely related target sequences, such as genetic alleles. Where closely related target sequences differ at a single nucleotide, it is preferred that open circle probes be designed with the complement of this nucleotide occurring at one end of the open circle probe, or at one of the ends of the gap oligonucleotide(s). Ligation of gap oligonucleotides with a mismatch at either terminus is extremely unlikely because of the combined effects of hybrid instability and enzyme discrimination. When the TS-DNA is generated, it will carry a copy of the gap oligonucleotide sequence that led to a correct ligation. Gap oligonucleotides may give even greater discrimination between related target sequences in certain circumstances, such as those involving wobble base pairing of alleles. Features of open circle probes and gap oligonucleotides that increase the target-dependency of the ligation operation are generally analogous to such features developed for use with the ligation chain reaction. These features can be incorporated into open circle probes and gap oligonucleotides for use in LM-RCA. In particular, European Patent Application EP0439182 describes several features for enhancing target-dependency in LCR that can be adapted for use in LM-RCA. The use of stop bases in the gap space, as described in European Patent Application EP0439182, is a preferred mode of enhancing the target discrimination of a gap-filling ligation operation.

A preferred form of target sequence discrimination can be accomplished by employing two types of open circle probes. These two OCPs would be designed essentially as shown in FIG. 2, with small modifications. In one embodiment, a single gap oligonucleotide is used which is the same for both target sequences, that is, the gap oligonucleotide is complementary to both target sequences. In a preferred embodiment, a gap-filling ligation operation can be used (Example 3). Target sequence discrimination would occur by virtue of mutually exclusive ligation events, or extension-ligation events, for which only one of the two open-circle probes is competent. Preferably, the discriminator nucleotide would be located at the penultimate nucleotide from the 3' end of each of the open circle probes. The two open circle probes would also contain two different detection tags designed to bind alternative detection probes and/or address probes. Each of the two detection probes would have a different detection label. Both open circle probes would have the same primer complement portion. Thus, both ligated open circle probes can be amplified using a single primer. Upon array hybridization, each detection probe would produce a unique signal, for example, two alternative fluorescence colors, corresponding to the alternative target sequences.

E. Optimization of RCA

1. Assay Background

A potential source of background signals is the formation of circular molecules by non-target-directed ligation events.

The contribution of such events to background signals can be minimized using five strategies, alone or in combination, as follows:

(a) The use of a thermostable DNA ligase such as AMPLIGASE® (Kalin et al. (1992)) or the *T. thermophilus* DNA ligase (Barany (1991)) will minimize the frequency of non-target-directed ligation events because ligation takes place at high temperature (50 to 75° C.).

(b) In the case of in situ hybridization, ligation of the open circle probe to the target sequence permits extensive washing. This washing will remove any circles that may have been formed by non-target-directed ligation, while circles ligated on-target are impossible to remove because they are topologically trapped (Nilsson et al. (1994)).

(c) The use of one or more gap oligonucleotides provides additional specificity in the ligation event. Using a gap oligonucleotide greatly reduces the probability of non-target-directed ligation. Particularly favored is the use of a gap oligonucleotide, or a gap-filling ligation operation, coupled to a capture hybridization step where the complementary portion of an address probe spans the ligation junction in a highly discriminatory fashion, as shown below and in FIG. 6.

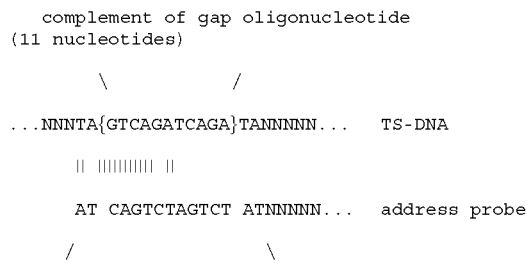

complementary portion of address probe (15 nucleotides hybridized) Brackets ({ }) mark sequence complementary to the gap oligonucleotide. The TS-DNA shown is SEQ ID NO:10 and the address probe sequence shown is SEQ ID NO:4. This system can be used with gap oligonucleotides of any length. Where the gap between the ends of an open circle probe hybridized to a target sequence is larger than the desired address probe length, an address probe can be designed to overlap just one of the junctions between the gap sequence and the open circle probe sequence.

The capture step involves hybridization of the amplified DNA to an address probe via a specific sequence interaction at the ligation junction, involving the complement of the gap oligonucleotide, as shown above. Guo et al. (1994), have shown that 15-mer oligonucleotides bound covalently on glass slides using suitable spacers, can be used to capture amplified DNA with reasonably high efficiency. This system can be adapted to detection of amplified nucleic acid (TS-DNA or TS-RNA) by using address probes to capture the amplified nucleic acid. In the example shown above, only LM-RCA amplified DNA generated from correct ligation events will be captured on the solid-state detector.

Optionally one may use additional immobilizing reagents, known in the art as capture probes (Syvanen et al., *Nucleic Acids Res.*, 14:5037 (1986)) in order to bind nucleic acids containing the target sequence to a solid surface. Suitable capture probes contain biotinylated oligonucleotides (Langer et al. (1981)) or terminal biotin groups. Immobilization may take place before or after the ligation reaction. Immobilization serves to allow removal of unligated open circle probes as well as non-specifically ligated circles.

(d) Using ligation conditions that favor intramolecular ligation. Conditions are easily found where circular ligation of OCPs occurs much more frequently than tandem linear ligation of two OCPs. For example, circular ligation is favored when the temperature at which the ligation operation is performed is near the melting temperature ($T_m$) of the least stable of the left target probe portion and the right target probe portion when hybridized to the target sequence. When ligation is carried out near the $T_m$ of the target probe portion with the lowest $T_m$, the target probe portion is at association/dissociation equilibrium. At equilibrium, the probability of association in cis (that is, with the other target probe portion of the same OCP) is much higher than the probability of association in trans (that is, with a different OCP). When possible, it is preferred that the target probe portions be designed with melting temperatures near suitable temperatures for the ligation operation. The use of a thermostable ligase, however, allows a wide range of ligation temperatures to be used, allowing greater freedom in the selection of target sequences.

(e) Peptide nucleic acids form extremely stable hybrids with DNA, and have been used as specific blockers of PCR reactions (Orum et al., *Nucleic Acids Res.*, 21:5332-5336 (1993)). A special PNA probe, referred to herein as a PNA clamp, can be used to block rolling circle amplification of OCPs that have been ligated illegitimately (that is, ligated in the absence of target). By using one or more gap oligonucleotides during ligation, or by using gap-filling ligation, illegitimately ligated circles will lack the gap sequence and they can be blocked with a PNA clamp that is complementary to the sequence resulting from the illegitimate ligation of the 3' end and the 5' end of the OCP. This is illustrated in the diagram below, where the PNA clamp llllrrrr is positioned exactly over the junction:

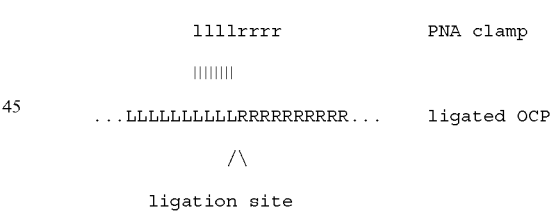

In this diagram, "L" and "l" represent a nucleotide in the left target probe portion of the OCP and its complement in the PNA clamp, and "R" and "r" represent a nucleotide in the right target probe portion of the OCP and its complement in the PNA clamp. The most preferred length for a PNA clamp is 8 to 10 nucleotides. The PNA clamp is incapable of hybridizing to unligated OCP because it can only form four to five base pairs with either target probe portion, and it is also incapable of hybridizing with correctly ligated OCP because a gap sequence is present. However, the PNA clamp will hybridize strongly with illegitimately ligated OCP, and it will block the progress of the rolling circle reaction because the DNA polymerase is incapable of displacing a hybridized PNA molecule. This prevents amplification of illegitimately ligated OCPs.

2. Removing Excess Unligated OCPs

The gene 6 exonuclease of phage T7 provides a useful tool for the elimination of excess open circle probes and excess gap oligonucleotides that will bind to the TS-DNA or LM-RCT transcripts and interfere with its hybridization to detection probes. This exonuclease digests DNA starting from the 5'-end of a double-stranded structure. It has been used successfully for the generation of single-stranded DNA after PCR amplification (Holloway et al., *Nucleic Acids Res.* 21:3905-3906 (1993); Nikiforov et al., *PCR Methods and Applications* 3:285-291(1994)). In an LM-RCA assay this enzyme can be added after ligation, together with the rolling circle DNA polymerase. To protect TS-DNA from degradation, the rolling circle replication primer can contain 3 or 4 phosphorothioate linkages at the 5' end, to make this molecule resistant to the exonuclease (Nikiforov et al. (1994)). The exonuclease will degrade excess open circle probe molecules as they become associated with the rolling circle DNA product. The use of this nuclease eliminates the need for capture probes as well as the need for washing to remove excess probes. In general, such a nuclease digestion should not be used when performing LM-RCT, since unligated OCPs and gap oligonucleotides are needed to form a double-stranded transcription template with the TS-DNA. This nuclease digestion is a preferred method of eliminating unligated OCPs and gap oligonucleotides when nested LM-RCA is to be performed.

EXAMPLES

Example 1

Target-mediated Ligation of Open Circle Probes and Rolling Circle Replication of Ligated Open Circle Probes 1. Ligation of Open Circle Probes Linear oligonucleotides with 5'-phosphates are efficiently ligated by ligase in the presence of a complementary target sequence. In particular, open circle probes hybridized to a target sequence as shown in FIG. 1, and open circle probes with gap oligonucleotides hybridized to a target sequence as shown in as shown in FIG. 2, are readily ligated. The efficiency of such ligation can be measured by LM-RCA.

The following is an example of target-dependent ligation of an open circle probe:

A DNA sample (target sample) is heat-denatured for 3 minutes at 95° C., and incubated under ligation conditions (45 minutes at 60° C.) in a buffer consisting of 20 mM Tris-HCl (pH 8.2), 25 mM KCl, 10 mM MgCl$_2$, 0.5 mM NAD, 0.05% Triton X-100, in the presence of (a) DNA ligase (AMPLI-GASE®, Epicentre Technologies) at a concentration of 1 unit per 50 μl, and (b) the following 5'-phosphorylated oligonucleotides:

This results in hybridization of the open circle probe and gap oligonucleotide to the target sequence, if present in the target sample, and ligation of the hybridized open circle probe and gap oligonucleotide.

2. Measuring the Rate of Rolling Circle Replication (a) On large template: 7 kb single-stranded phage M13 circle The rate of oligonucleotide-primed rolling circle replication on single-stranded M13 circles mediated by any DNA polymerase can be measured by using the assay described by Blanco et al., *J. Biol. Chem.* 264:8935-8940 (1989). The efficiency of primed synthesis by the φ29 DNA polymerase is stimulated about 3-fold in the presence of Gene-32 protein, a single-stranded DNA binding protein.

(b) On small templates: 110-nucleotide ligated open circle probes

The rate of oligonucleotide-primed rolling circle replication on single-stranded small circles of 110 bases was measured using the φ29 DNA polymerase generally as described in Example 2. After five minutes of incubation, the size of the DNA product is approximately 16 kilobases. This size corresponds to a polymerization rate of 53 nucleotides per second. The rate of synthesis with other DNA polymerases can be measured and optimized using a similar assay, as described by Fire and Xu, *Proc. Natl. Acad. Sci. USA* 92:4641-4645 (1995). It is preferred that single-stranded circles of 110 nucleotides be substituted for the 34 nucleotide circles of Fire and Xu.

The φ29 DNA polymerase provides a rapid rate of polymerization of the φ29 rolling circle reaction on 110 nucleotide circular templates. At the observed rate of 50 nucleotides per second, a 35 minute polymerization reaction will produce a DNA product of approximately 105,000 bases. This would yield an amplification of 954-fold over the original 110-base template. Fire and Xu (1995) shows that rolling circle reactions catalyzed by bacterial DNA polymerases may take place on very small circular templates of only 34 nucleotides. On the basis of the results of Fire and Yu, rolling circle replication can be carried out using circles of less than 90 nucleotides.

Example 2

Detection of a Mutant Ornithine Transcarbamylase (OTC) Gene Using LM-RCA Followed by Transcription (LM-RCT)

This example describes detection of human DNA containing a mutant form (G to C) at position 114 of exon 9 of the ornithine transcarbamylase gene (Hata et al., *J. Biochem.* 103:302-308 (1988)). Human DNA for the assay is prepared by extraction from buffy coat using a standard phenol procedure.

```
Open circle probe (111 nucleotides):

5'-GCCTGTCCAGGGATCTGCTCAAGACTCGTCATGTCTCAGTAGCTTCTAACG

GTCACAAGCTTCTAACGGTCACAAGCTTCTAACGGTCACATGTCTGCTGCCCT

CTGTATT-3' (SEQ ID NO: 1)

Gap oligonucleotide: 5'-CCTT-3'
```

1. Two DNA samples (400 ng each) are heat-denatured for 4 minutes at 97° C., and incubated under ligation conditions in the presence of two 5'-phosphorylated oligonucleotides, an open circle probe and one gap oligonucleotide:
Open circle probe (95 nucleotides):

5'-GAGGAGAATAAAAGTTTCTCATAAGACTCGTCATGTCTCAGCAGCTTCTA (SEQ ID NO: 5)
ACGGTCACTAATACGACTCACTATAGGTTCTGCCTCTGGGAACAC-3'

Gap oligonucleotide for mutant gene (8 nucleotides)

5'-TAGTGATG-3'

Gap oligonucleotide for wild type gene (8 nucleotides)

5'-TAGTGATC-3'

T4 DNA ligase (New England Biolabs) is present at a concentration of 5 units per µl, in a buffer consisting of 10 mM Tris-HCl (pH 7.5), 0.20 M NaCl, 10 mM MgCl$_2$, 2 mM ATP. The concentration of open circle probe is 80 nM, and the concentration of gap oligonucleotide is 100 nM. The total volume is 40 µl. Ligation is carried out for 25 minutes at 37° C.

2. 25 µl are taken from each of the above reactions and mixed with an equal volume of a buffer consisting of 50 mM Tris-HCl (pH 7.5), 10 mM MgCl$_2$, 1 mM DTT, 400 µM each of dTTP, dATP, dGTP, dCTP, which contains an 18-base rolling circle replication primer 5'-GCTGAGA-CATGACGAGTC-3' (SEQ ID NO:6), at a concentration of 0.2 µM. The φ29 DNA polymerase (160 ng per 50 µl) is added and the reaction mixture is incubated for 30 minutes at 30° C.

3. To the above solutions a compensating buffer is added to achieve the following concentrations of reagents: 35 mM Tris-HCl (pH 8.2), 2 mM spermidine, 18 mM MgCl$_2$, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reaction is incubated for 90 minutes at 37° C.

4. One-tenth volume of 5 M NaCl is added to the above reactions, and the resulting solution is mixed with an equal volume of ExpressHyb reagent (Clontech Laboratories, Palo Alto, Calif.). Hybridization is performed by contacting the amplified RNA solution, under a cover slip, with the surface of a glass slide (Guo et al. (1994)) containing a 2.5 mm dot with 2×10$^{11}$ molecules of a covalently bound 29-mer oligonucleotide with the sequence 5'-TTTTTTTTTTTCCAACCTCCATCACTAGT-3' (SEQ ID NO:7). The last 14 nucleotides of this sequence are complementary to the amplified mutant gene RNA, and hence the mutant RNA binds specifically. Another 2.5 mm dot on the slide surface contains 2×10$^{11}$ molecules of a covalently bound 29-mer oligonucleotide with the sequence 5'-TTTTTTTTTTTCCAACCTCGATCAC-TAGT-3' (SEQ ID NO:8). The last 14 nucleotides of this sequence are complementary to the amplified wild type gene RNA, and hence the wild type RNA binds specifically. The glass slide is washed once with 2×SSPE as described (Guo et al. (1994)), then washed twice with 2×SSC (0.36 M sodium saline citrate), and then incubated with fluoresceinated avidin (5 µg/ml) in 2×SSC for 20 minutes at 30° C. The slide is washed 3 times with 2×SSC and the slide-bound fluorescence is imaged at 530 nm using a Molecular Dynamics Fluorimager.

Example 3

Detection of a Mutant Ornithine Transcarbamylase (OTC) Gene Using Gap-filling LM-RCT This example describes detection of human DNA containing a mutant form (G to C) at position 114 of exon 9 of the ornithine transcarbamylase gene (Hata et al. (1988)) using gap-filling LM-RCT. Human DNA for the assay is prepared by extraction from buffy coat using a standard phenol procedure. In this example, two different open circle probes are used to detect the mutant and wild type forms of the gene. No gap oligonucleotide is used.

1. Two DNA samples (400 ng each) are heat-denatured for 4 minutes at 97° C., and incubated in the presence of one of the following 5'-phosphorylated open circle probes.
Open circle probe for mutant gene (96 nucleotides):
5'-TAAAAGACTTCATCATCCATCTCATAA-GACTCGTCATGTCTCAGCAGCT-TCTAACGGTCACTAATACGACTCACTAT-AGGGGAACACTAGTGATGG-3' (SEQ ID NO:11). When this probe hybridizes to the target sequence, there is a gap space of seven nucleotides between the ends of the open circle probe.
Open circle probe for wild type gene (96 nucleotides):
5'-TAAAAGACTTCATCATCCATCTCATAA-GACTCGTCATGTCTCAGCAGCT-TCTAACGGTCACTAATACGACTCACTAT-AGGGGAACACTAGTGATCG-3' (SEQ ID NO:12). When this probe hybridizes to the target sequence, there is a gap space of seven nucleotides between the ends of the open circle probe.

Each of the OCP-target sample mixtures are incubated in an extension-ligation mixture as described by Abravaya et al. (1995). The reaction, in a volume of 40 µl, contains 50 mM Tris-HCl (pH 7.8), 25 mM MgCl$_2$, 20 mM potassium acetate, 10 µM NAD, 80 nM open circle probe, 40 µM dATP, 40 µM dGTP, 1 Unit *Thermus flavus* DNA polymerase (lacking 3'-5' exonuclease activity; MBR, Milwaukee, Wis.), and 4000 Units *Thermus thermophilus* DNA ligase (Abbott laboratories). The reaction is incubated for 60 seconds at 85° C., and 50 seconds at 60° C. in a thermal cycler. No thermal cycling is performed. This results in hybridization of the open circle probe to the target sequence, if present, filling in of the gap space by the *T. flavus* DNA polymerase, and ligation by the *T. thermophilus* ligase. The discriminating nucleotide in the open circle probes above is the penultimate nucleotide. *T. flavus* DNA polymerase is used in the reaction to match the thermal stability of the *T. thermophilus* ligase.

2. 25 µl are taken from each of the above reactions and mixed with an equal volume of a buffer consisting of 50 mM Tris-HCl (pH 7.5), 10 mM MgCl$_2$, 1 mM DTT, 400 µM each of dTTP, dATP, dGTP, dCTP; and containing the 18-base oligonucleotide primer 5'-GCTGAGACATGAC-GAGTC-3' (SEQ ID NO:6), at a concentration of 0.2 µM.

The φ29 DNA polymerase (160 ng per 50 µl) is added and the reaction mixture is incubated for 30 minutes at 30° C. to perform rolling circle amplification catalyzed by φ29 DNA polymerase. The *Thermus flavus* DNA polymerase does not significantly interfere with rolling circle replication because it has little activity at 30° C. If desired, the *Thermus flavus* DNA polymerase can be inactivated, prior to rolling circle replication, by adding a neutralizing antibody analogous to antibodies for blocking Taq DNA polymerase prior to PCR (Kellogg et al., *Biotechniques* 16(6):1134-1137 (1994)).

3. To each of the above solutions are added compensating buffer to achieve the following concentrations of reagents: 35 mM Tris-HCl (pH 8.2), 2 mM spermidine, 18 mM MgCl$_2$, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reactions are incubated for 90 minutes at 37° C.

4. One-tenth volume of 5 M NaCl is added to the each solution containing the biotinylated RNA generated by T7 RNA polymerase, and the resulting solution is mixed with an equal volume of ExpressHyb reagent (Clontech laboratories, Palo Alto, Calif.). Hybridization is performed by contacting the amplified RNA solution, under a cover slip, with the surface of a glass slide (Guo et al. (1994)) containing a 2.5 mm dot with 2×10$^{11}$ molecules of a covalently bound 29-mer address probe with the sequence 5'-TTTTTTTTTTTCCAAATTCTCCTCCATCA-3' (SEQ ID NO:13). The last 14 nucleotides of this sequence are complementary to the amplified mutant gene RNA, and hence the mutant RNA binds specifically. Another 2.5 mm dot on the slide surface contains 2×10$^{11}$ molecules of a covalently bound 29-mer address probe with the sequence 5'-TTTTTTTTTTTCCAAATTCTCCTCGATCA-3' (SEQ ID NO:14). The last 14 nucleotides of this sequence are complementary to the amplified wild type gene RNA, and hence the wild type RNA binds specifically. The glass slide is washed once with 2×SSPE as described (Guo et al. (1994)), then washed twice with 2×SSC (0.36 M sodium saline citrate), and then incubated with fluoresceinated avidin (5 µg/ml) in 2×SSC for 20 minutes at 30° C. The slide is washed 3 times with 2×SSC and the slide-bound fluorescence is imaged at 530 nm using a Molecular Dynamics Fluorimager.

Example 4

Reverse Transcription of Ornithine Transcarbamylase (OTC) mRNA Followed by Mutant cDNA Detection Using Gap-filling LM-RCT This example describes detection of human MRNA containing a mutant form (G to C) at position 114 of exon 9 of the ornithine transcarbamylase gene (Hata et al. (1988)) using cDNA generated by reverse transcription. RNA for the assay is prepared by TRIzol (Life Technologies, Inc., Gaithersburg, Md.) extraction from liver biopsy.

1. OTC exon 9 cDNA is generated as follows:
A liver biopsy sample is stored at −80° C. in a 0.5 ml. reaction tube containing 40 Units of RNase inhibitor (Boehringher Mannheim). Total RNA is extracted from the frozen sample using TRIzol reagent (Life Technologies, Inc., Gaithersburg, Md.), and dissolved in 10 µl water. A 19 µl reaction mixture is prepared containing 4 µl of 25 mM MgCl$_2$, 2 µl of 400 mM KCl, 100 mM Tris-HCl (pH 8.3), 8 µl of a 2.5 mM mixture of dNTP's (dATP, dGTP, dTTP, dCTP), 1 µl of MuLV reverse transcriptase (50 U, Life Technologies, Inc., Gaithersburg, Md.), 1 µl of MuLV reverse transcriptase primer (5'-TGTCCACTTTCT-GTTTTCTGCCTC-3'; SEQ ID NO:15), 2 µl of water, and 1 µl of RNase inhibitor (20 U). The reaction mixture is added to 1 µl of the Trizol-purified RNA solution, and incubated at 42° C. for 20 minutes to generate cDNA.

2. Two 20 µl cDNA samples from step 1 are heat-denatured for 4 minutes at 98° C., and incubated under ligation conditions in the presence of two 5'-phosphorylated probes:
Open circle probe (95 nucleotides):

```
5'-ATCACTAGTGTTCCTTCTCATAAGACTCGTCATGTCTCAGCAGCTTCTAAC (SEQ ID NO: 16)

GGTCACTAATACGACTCACTATAGGGGATGATGAAGTCTTTTAT-3'
```

Gap probe for mutant gene (8 nucleotides):

```
5'-TAGTGATG-3'
```

Gap probe for wild type gene (8 nucleotides):

```
5'-TAGTGATC-3'
```

T4 DNA ligase (New England Biolabs) is added at a concentration of 5 units per µl, in a buffer consisting of 10 mM Tris-HCl (pH 7.5), 0.20 M NaCl, 10 mM MgCl$_2$, 2 mM ATP. The concentration of open circle probe is 80 nM, and the concentration of gap oligonucleotide is 100 nM. The total volume is 40 µliters. Ligation is carried out for 25 minutes at 37° C.

3. 25 µl are taken from each of the above reactions and mixed with an equal volume of a buffer consisting of 50 mM Tris-HCl (pH 7.5), 10 mM MgCl$_2$, 1 mM DTT, 200 µM each of dTTP, dATP, dGTP, dCTP; and containing the 18-base rolling circle replication primer 5'-GCTGAGA-CATGACGAGTC-3' (SEQ ID NO:6), at a concentration of 0.2 µM. The φ29 DNA polymerase (160 ng per 50 µl) is added and the reaction mixtures are incubated for 30 minutes at 30° C.

4. To the above solutions are added compensating buffer to achieve the following concentrations of reagents: 35 mM Tris-HCl (pH 8.2), 2 mM spermidine, 18 mM MgCl$_2$, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reaction is incubated for 90 minutes at 37° C.

5. One-tenth volume of 5 M NaCl is added to the each solution containing the biotinylated RNA generated by T7 RNA polymerase, and the resulting solution is mixed with an equal volume of ExpressHyb reagent (Clontech laboratories, Palo Alto, Calif.). Hybridization is performed by contacting the amplified RNA solution, under a cover slip, with the surface of a glass slide (Guo et al. (1994)) containing a 2.5 mm dot with 2×10$^{11}$ molecules of a covalently bound 29-mer address probe with the sequence 5'-TTTTTTTTTTTTTTTGATGGAGGAGAAT-3' (SEQ ID NO:17). The last 14 nucleotides of this sequence are complementary to the amplified mutant gene RNA, and hence the mutant RNA binds specifically. Another 2.5 mm dot on the slide surface contains $2\times10^{11}$ molecules of a covalently bound 29-mer address probe with the sequence 5'-TTTTTTTTTTTTTTTGATCGAGGAGAAT-3' (SEQ ID NO:9). The last 14 nucleotides of this sequence are complementary to the amplified wild type gene RNA, and hence the wild type RNA binds specifically. The glass slide is washed once with 2×SSPE as described (Guo et al. (1994)), then washed twice with 2×SSC (0.36 M sodium saline citrate), and then incubated with fluoresceinated avidin (5 µg/ml) in 2×SSC for 20 minutes at 30° C. The slide is washed 3 times with 2×SSC and the slide-bound fluorescence is imaged at 530 nm using a Molecular Dynamics Fluorimager.

Example 5

Multiplex Immunoassay Coupled to Rolling Circle Amplification

This example describes an example of multiplex detection of different target molecules using reporter antibodies. The signal that is detected is produced by rolling circle amplification of the target sequence portion of the reporter antibodies.

1. Three different monoclonal antibodies, each specific for a different target molecule, are coupled to three different arbitrary DNA sequences (A, B, C) that serve as unique identification tags (target sequences). In this example, the three antibodies are maleimide-modified and are specific for β-galactosidase, hTSH, and human chorionic gonadotropin (hCG). The antibodies are coupled to aminated DNA oligonucleotides, each oligonucleotide being 50 nucleotides long, using SATA chemistry as described by Hendrickson et al. (1995). The resulting reporter antibodies are called reporter antibody A, B, and C, respectively.

2. Antibodies specific for the target molecules (not the reporter antibodies) are immobilized on microtiter dishes as follows: A 50 µl mixture containing 6 µg/ml of each of the three antibodies in sodium bicarbonate (pH 9) is applied to the wells of a microtiter dish, incubated overnight, and washed with PBS-BLA (10 mM sodium phosphate (pH 7.4), 150 mM sodium chloride, 2% BSA, 10% β-lactose, 0.02% sodium azide) to block non-adsorbed sites.

3. Serial dilutions of solutions containing one or a combination of the three target molecules (hTSH, hCG, and β-galactosidase) are added to the wells. Some wells are exposed to one target molecule, a mixture of two target molecules, or a mixture of all three target molecules. After 1 hour of incubation, the wells are washed three times with TBS/Tween wash buffer as described by Hendrickson et al. (1995).

4. Fifty microliters of an appropriately diluted mixture of the three reporter antibodies (A+B+C) are added to each well of the microtiter dish. The plate is incubated at 37° C. for 1 hour, and then washed four times with TBS/Tween buffer.

5. To each well is added a mixture of three pairs of open circle probes and gap oligonucleotides, each pair specific for one of the three target sequence portions of the reporter antibodies. In this example, the open circle probes have the same spacer region of 49 bases including a universal primer complement portion, and different 18 nucleotide target probe portions at each end. Each cognate pair of open circle probe and gap oligonucleotide is designed to hybridize to a specific target sequence (A, B, or C) in the target sequence portion of the reporter antibodies. Specifically, Open circle probe A' has left and right target probe portions complementary to two 18-base sequences in tag sequence A separated by 8 bases that are complementary to the 8-nucleotide gap oligonucleotide A'. The same is the case for open circle probe and gap oligonucleotide pairs B' and C'. The concentration of each open circle probe is 80 nM, and the concentration of each gap oligonucleotide is 120 nM.

6. T4 DNA ligase (New England Biolabs) is added to each microtiter well at a concentration of 5 units per µl, in a reaction buffer consisting (10 mM Tris-HCl (pH 7.5), 40 mM potassium acetate, 10 mM $MgCl_2$, 2 mM ATP). The total volume in each well is 40 µliters. Ligation is carried out for 45 minutes at 37° C.

7. To each microtiter well is added 20 µl of a compensating solution containing dTTP, dATP, dGTP, dCTP (400 µM each), the universal 18-base oligonucleotide primer 5'-GCTGAGACATGACGAGTC-3' (SEQ ID NO:6) (at a final concentration of 0.2 µM), and φ29 DNA polymerase (at 160 ng per 50 µl). The reaction for 30 minutes at 30° C.

8. After incubation, a compensating buffer is added to each well to achieve the following concentrations of reagents: 35 mM Tris-HCl (pH 8.2), 2 mM spermidine, 18 mM $MgCl_2$, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reaction is incubated for 90 minutes at 37° C., generating biotinylated RNA.

9. One-tenth volume of 5 M NaCl is added to each well, and the resulting solution is mixed with and equal volume of ExpressHyb reagent (Clontech laboratories, Palo Alto, Calif.). Hybridization is performed by contacting the mixture of amplified RNAs, under a cover slip, with the surface of a glass slide containing three separate dots of $2\times10^{11}$ molecules of three different covalently bound 31-mer oligonucleotides (A, B, C) (Guo et al. (1994)). The last 16 bases of each oligonucleotide are complementary to a specific segment (4 bases+8 bases+4 bases), centered on the 8-base gap sequence, of each of the possible amplified RNAs generated from tag sequences A, B, or C. Hybridization is carried out for 90 minutes at 37° C. The glass slide is washed once with 2×SSPE as described (Guo et al. (1994)), then washed twice with 2×SSC (0.36 M sodium saline citrate), and then incubated with fluoresceinated avidin (5 µg/ml) in 2×SSC for 20 minutes at 30° C. The slide is washed 3 times with 2×SSC and the surface-bound fluorescence is imaged at 530 nm using a Molecular Dynamics Fluorimager to determine if any of tag sequences A or B or C was amplified.

All publications cited herein are hereby incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method comprising
a DNA ligation operation and an amplification operation,
wherein the DNA ligation operation comprises circularization of an open circle probe, wherein circularization of the open circle probe is dependent on hybridization of the open circle probe to a target sequence,
wherein the amplification operation comprises a) rolling circle replication of the circularized open circle probe to produce tandem sequence DNA and b) secondary DNA strand displacement,
wherein secondary DNA strand displacement is accomplished by hybridizing secondary DNA strand displacement primers to the tandem sequence DNA produced by the rolling circle replication of the circularized open circle probe to produce secondary tandem sequence DNA, and
wherein the tandem sequence DNA as well as the secondary tandem sequence DNA is detected.

2. The method of claim 1 wherein the tandem sequence DNA is detected using molecular beacon detection probes.

3. The method of claim 1 wherein the tandem sequence DNA is detected using detection probes labeled with fluorescent moieties where the fluorescent moieties fluoresce only when the detection probe is hybridized, wherein the detection probes hybridize to the tandem sequence DNA.

4. The method of claim 1 wherein the target sequence is coupled to a specific binding molecule, wherein the specific binding molecule can interact with a target molecule.

5. The method of claim 4 wherein the target molecule is a protein.

6. The method of claim 4 wherein the target molecule is a nucleic acid molecule.

7. A method comprising
a) tethering an oligonucleotide portion of a reporter binding agent to a specific binding molecule portion of the reporter binding agent, wherein the oligonucleotide portion of the reporter binding agent is an amplification target circle; and b) performing an amplification operation,
wherein the specific binding molecule portion of the reporter binding agent binds to a target molecule,
wherein the oligonucleotide portion of the reporter binding agent is not the target molecule, and
wherein the amplification operation comprises amplification of the amplification target circle via rolling circle replication to produce tandem sequence DNA.

8. The method of claim 7 wherein the tandem sequence DNA is detected using molecular beacon detection probes.

9. The method of claim 7 wherein the tandem sequence DNA is detected using detection probes labeled with fluorescent moieties where the fluorescent moieties fluoresce only when the detection probe is hybridized, wherein the detection probes hybridize to the tandem sequence DNA.

10. The method of claim 7 wherein the target molecule is a protein.

11. The method of claim 7 wherein the target molecule is a nucleic acid molecule.

12. The method of claim 7 wherein the specific binding molecule is an antibody.

13. A method comprising
a DNA ligation operation and an amplification operation,
wherein the DNA ligation operation comprises circularization of an open circle probe, wherein circularization of the open circle probe is dependent on hybridization of the open circle probe to a target sequence,
wherein the amplification operation comprises rolling circle amplification of the circularized open circle probe to produce tandem sequence DNA, wherein the tandem sequence DNA is detected, wherein rolling circle amplification is primed by a rolling circle replication primer, a secondary DNA strand displacement primer, and a tertiary DNA strand displacement primer,
wherein the rolling circle replication primer and tertiary DNA strand displacement primer are complementary to the circularized open circle probe, wherein the secondary DNA strand displacement primer is complementary to sequences in the tandem sequence DNA, wherein the secondary DNA strand displacement primer is not complementary to the complement of either the rolling circle replication primer or the tertiary DNA strand displacement primer.

14. The method of claim 13 wherein the tandem sequence DNA is detected using molecular beacon detection probes.

15. The method of claim 13 wherein the tandem sequence DNA is detected using detection probes labeled with fluorescent moieties where the fluorescent moieties fluoresce only when the detection probe is hybridized, wherein the detection probes hybridize to the tandem sequence DNA.

16. The method of claim 13 wherein the target sequence is coupled to a specific binding molecule, wherein the specific binding molecule can interact with a target molecule.

17. The method of claim 16 wherein the target molecule is a protein.

18. The method of claim 16 wherein the target molecule is a nucleic acid molecule.

19. A method comprising
an amplification operation,
wherein a reporter binding agent and a target molecule are brought into contact, wherein the reporter binding agent comprises a specific binding molecule and an oligonucleotide, wherein the specific binding molecule interacts with the target molecule, wherein an amplification target circle and the reporter binding agent are brought into contact,
wherein the amplification operation comprises rolling circle amplification of the amplification target circle to produce tandem sequence DNA, wherein the tandem sequence DNA is detected, wherein rolling circle amplification is primed by the oligonucleotide of the reporter binding agent, a secondary DNA strand displacement primer, and a tertiary DNA strand displacement primer.

20. The method of claim 19 wherein the tandem sequence DNA is detected using molecular beacon detection probes.

21. The method of claim 19 wherein the tandem sequence DNA is detected using detection probes labeled with fluorescent moieties where the fluorescent moieties fluoresce only when the detection probe is hybridized, wherein the detection probes hybridize to the tandem sequence DNA.

22. The method of claim 19 wherein the target molecule is a protein.

23. The method of claim 19 wherein the target molecule is a nucleic acid molecule.

24. A method comprising
an amplification operation,
wherein a reporter binding agent and a target molecule are brought into contact, wherein the reporter binding agent comprises a specific binding molecule and an oligonucleotide, wherein the oligonucleotide comprises an amplification target circle, wherein the specific binding molecule interacts with the target molecule,
wherein the amplification operation comprises rolling circle amplification of the amplification target circle to produce tandem sequence DNA, wherein the tandem sequence DNA is detected, wherein rolling circle amplification is primed by a rolling circle replication primer, a secondary DNA strand displacement primer, and a tertiary DNA strand displacement primer,
wherein the rolling circle replication primer and tertiary DNA strand displacement primer, are complementary to the amplification target circle, wherein the rolling circle replication primer and tertiary DNA strand displacement primer are not complementary to the same sequence on the amplification target circle, wherein the secondary DNA strand displacement primer is complementary to sequences in the tandem sequence DNA, wherein the secondary DNA strand displacement primer is not complementary to the complement of either the rolling circle replication primer or the tertiary DNA strand displacement primer.

25. The method of claim 24 wherein the tandem sequence DNA is detected using molecular beacon detection probes.

26. The method of claim 24 wherein the tandem sequence DNA is detected using detection probes labeled with fluorescent moieties where the fluorescent moieties fluoresce only when the detection probe is hybridized, wherein the detection probes hybridize to the tandem sequence DNA.

27. The method of claim 24 wherein the target molecule is a protein.

28. The method of claim 24 wherein the target molecule is a nucleic acid molecule.

* * * * *

UNITED STATES PATENT AND TRADEMARK OFFICE
CERTIFICATE OF CORRECTION

PATENT NO. : 7,618,776 B2  
APPLICATION NO. : 10/896513  
DATED : November 17, 2009  
INVENTOR(S) : Paul M. Lizardi Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this

Twenty-sixth Day of October, 2010

David J. Kappos  
*Director of the United States Patent and Trademark Office*

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
       (A) LENGTH: 111 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 1:

GCCTGTCCAG GGATCTGCTC AAGACTCGTC ATGTCTCAGT AGCTTCTAAC GGTCACAAGC      60

TTCTAACGGT CACAAGCTTC TAACGGTCAC ATGTCTGCTG CCCTCTGTAT T             111

(2) INFORMATION FOR SEQ ID NO: 2:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 2:

GAGCAGATCC CTGGACAGGC AAGGAATACA GAGGGCAGCA GACA                      44

(2) INFORMATION FOR SEQ ID NO: 3:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 3:

GTATTCCTTG CCTGGTATTC CTTGCCTG                                        28

(2) INFORMATION FOR SEQ ID NO: 4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 4:

ATCAGTCTAG TCTATNNNNN                                               20

(2) INFORMATION FOR SEQ ID NO: 5:

(i) SEQUENCE CHARACTERISTICS:
            (A) LENGTH: 95 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 5:

GAGGAGAATA AAAGTTTCTC ATAAGACTCG TCATGTCTCA GCAGCTTCTA ACGGTCACTA    60

ATACGACTCA CTATAGGTTC TGCCTCTGGG AACAC                              95

(2) INFORMATION FOR SEQ ID NO: 6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 6:

GCTGAGACAT GACGAGTC                                                 18

(2) INFORMATION FOR SEQ ID NO: 7:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 7:

TTTTTTTTTT TCCAACCTCC ATCACTAGT                                     29

(2) INFORMATION FOR SEQ ID NO: 8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 8:

TTTTTTTTTT TCCAACCTCG ATCACTAGT                                          29

(2) INFORMATION FOR SEQ ID NO: 9:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 9:

TTTTTTTTTT TTTTTTGATC GAGGAGAAT                                          29

(2) INFORMATION FOR SEQ ID NO: 10:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 10:

NNNNNATAGA CTAGACTGAT NNN                                                23

(2) INFORMATION FOR SEQ ID NO: 11:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 11:

TAAAAGACTT CATCATCCAT CTCATAAGAC TCGTCATGTC TCAGCAGCTT CTAACGGTCA        60

CTAATACGAC TCACTATAGG GGAACACTAG TGATGG                                  96

(2) INFORMATION FOR SEQ ID NO: 12:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 12:

TAAAAGACTT CATCATCCAT CTCATAAGAC TCGTCATGTC TCAGCAGCTT CTAACGGTCA      60

CTAATACGAC TCACTATAGG GGAACACTAG TGATCG      96

(2) INFORMATION FOR SEQ ID NO: 13:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 13:

TTTTTTTTTT TCCAAATTCT CCTCCATCA      29

(2) INFORMATION FOR SEQ ID NO: 14:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 14:

TTTTTTTTTT TCCAAATTCT CCTCGATCA      29

(2) INFORMATION FOR SEQ ID NO: 15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 15:

TGTCCACTTT CTGTTTTCTG CCTC      24

(2) INFORMATION FOR SEQ ID NO: 16:

(i) SEQUENCE CHARACTERISTICS:
            (A) LENGTH: 95 base pairs
            (B) TYPE: nucleic acid
            (C) STRANDEDNESS: single
            (D) TOPOLOGY: linear (ii) MOLECULE TYPE: DNA -continued (iii) HYPOTHETICAL: NO (iv) ANTI-SENSE: NO (xi) SEQUENCE DESCRIPTION: SEQ ID NO: 16:

ATCACTAGTG TTCCTTCTCA TAAGACTCGT CATGTCTCAG CAGCTTCTAA CGGTCACTAA        60

TACGACTCAC TATAGGGGAT GATGAAGTCT TTTAT                                  95

(2) INFORMATION FOR SEQ ID NO: 17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 17:

TTTTTTTTTT TTTTTTGATG GAGGAGAAT                                         29